(12) United States Patent
Ackermann et al.

(10) Patent No.: US 8,030,308 B2
(45) Date of Patent: Oct. 4, 2011

(54) BICYCLIC SULFONAMIDE DERIVATIVES WHICH ARE L-CPT 1 INHIBITORS

(75) Inventors: Jean Ackermann, Riehen (CH); Konrad Bleicher, Freiburg (DE); Simona M. Ceccarelli, Basel (CH); Odile Chomienne, Altkirch (FR); Patrizio Mattei, Riehen (CH); Ulrike Obst Sander, Reinach (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/941,374

(22) Filed: Nov. 8, 2010

(65) Prior Publication Data

US 2011/0046112 A1 Feb. 24, 2011

Related U.S. Application Data

(60) Division of application No. 12/696,145, filed on Jan. 29, 2010, now Pat. No. 7,879,845, which is a continuation of application No. 11/703,319, filed on Feb. 7, 2007, now Pat. No. 7,696,200.

(30) Foreign Application Priority Data

Feb. 13, 2006 (EP) .................................. 06101580

(51) Int. Cl.
C07D 241/50 (2006.01)
C07D 265/36 (2006.01)
C07D 413/12 (2006.01)
A61K 31/553 (2006.01)

(52) U.S. Cl. ........................ 514/249; 544/355

(58) Field of Classification Search .................. 544/355; 514/249

See application file for complete search history.

(56) References Cited

FOREIGN PATENT DOCUMENTS

| EP | 122109 | * | 10/1984 |
| EP | 1 243 583 | * | 9/2002 |
| WO | 2006/131452 A1 | * | 12/2006 |

OTHER PUBLICATIONS

Jackson et al., 1999, Biochem. J. 341, 483-489.
Jackson et al., 2000, J. Biol. Chem. 275, 19560-19566.
J. Am. Chem. Soc. 1983, 105, 5015.
Broadway, N.M., et al., FEBS Letters, vol. 371, pp. 137-139 (1995), XP-002398463.

* cited by examiner

*Primary Examiner* — Kahsay T Habte
(74) *Attorney, Agent, or Firm* — George W. Johnston; Dennis P. Tramaloni; Samuel H. Megerditchian

(57) ABSTRACT

The invention is concerned with novel heterobicyclic derivatives of formula (I)

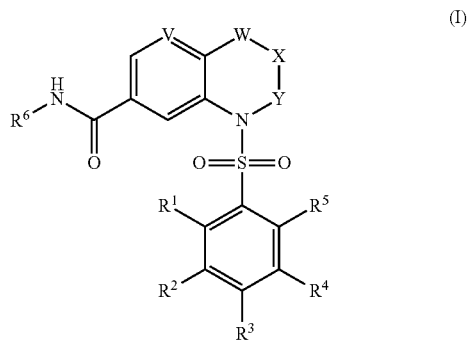

wherein $R^1$, $R^2$, $R^3$, $R^4$, $R^5$, $R^6$, V, W, X and Y are as defined in the description and in the claims, as well as physiologically acceptable salts and esters thereof. These compounds inhibit L-CPT1 and can be used as medicaments.

24 Claims, No Drawings

BICYCLIC SULFONAMIDE DERIVATIVES WHICH ARE L-CPT 1 INHIBITORS

PRIORITY TO RELATED APPLICATIONS

This application is a division of U.S. application Ser. No. 12/696,145, filed Jan. 29, 2010, now U.S. Pat. No. 7,879,845, which is a continuation of U.S. application Ser. No. 11/703,319, filed Feb. 7, 2007, now U.S. Pat. No. 7,696,200, Apr. 13, 2010, which claims the benefit of European Application No. 06101580.6, filed Feb. 13, 2006, which is hereby incorporated by reference in its entirety.

FIELD OF THE INVENTION

The invention is concerned with novel heterobicyclic derivatives of the formula (I)

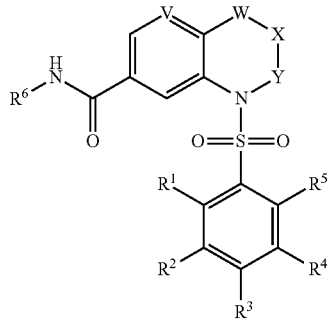

and pharmaceutically acceptable salts and esters thereof.

Further, the invention is concerned with a process for the manufacture of the above compounds, pharmaceutical preparations which contain such compounds as well as the use of these compounds for the production of pharmaceutical preparations.

All documents cited or relied upon below are expressly incorporated herein by reference.

BACKGROUND

High levels of free fatty acids (FFA) lead to an increase of liver mitochondrial β-oxidation, which is crucial to drive efficient gluconeogenesis. The mitochondrial oxidation of long-chain FFA requires the intervention of two membrane-bound carnitine-dependent palmitoyltransferases (CPTs). CPT1, the outer mitochondrial membrane enzyme, catalyzes the formation of long-chain acylcarnitines. Liver (L-CPT1) and muscle (M-CPT1) CPT1 isoforms are encoded by two different genes and inhibited by malonyl-CoA. The N-ter domain of L-CPT1 confers its lower sensitivity to malonyl CoA. CPT2, the inner mitochondrial membrane enzyme, reconverts long-chain acylcarnitines into long-chain acyl CoA esters. Long-chain acyl-CoAs are then β-oxidized to acetyl-CoA, which activates the pyruvate carboxylase and gluconeogenesis. According to the mechanism of action described above, pharmaceutically active substances which inhibit L-CPT1 reduce liver β-oxidation, consequently inhibit gluconeogenesis and therefore counteract hyperglycemia.

SUMMARY OF THE INVENTION

In an embodiment of the present invention, provided is a compound of formula (I):

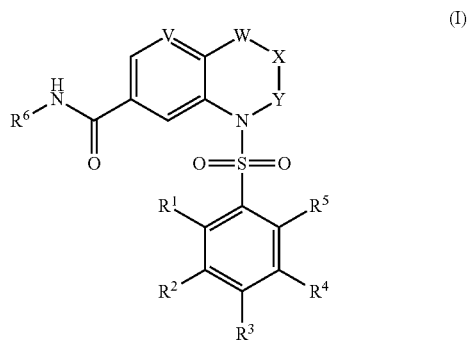

wherein:
V is N or —C(R$^7$)—;
W is a single bond or —C(R$^8$R$^9$)—;
X is O, S, SO, SO$_2$ or N(R$^{10}$);
Y is —C(R$^{11}$R$^{12}$)—, —C(R$^{11}$R$^{12}$)C(R$^{13}$R$^{14}$)—, —C(R$^{11}$R$^{12}$)C(R$^{13}$R$^{14}$)C(R$^{15}$R$^{16}$)—, —C(R$^{11}$R$^{12}$)C(R$^{13}$R$^{14}$)C(R$^{15}$R$^{16}$)C(R$^{17}$R$^{18}$)— or —C(R$^{11}$)=C(R$^{12}$)—;
R$^1$, R$^2$, R$^3$, R$^4$ and R$^5$ independently from each other are hydrogen, halogen, cyano, hydroxy, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H, lower-alkyl)-S(O)$_2$ or N(lower-alkyl)$_2$-S(O)$_2$, NH$_2$—C(O), N(H,lower-alkyl)-C(O), N(lower-alkyl)$_2$-C(O), COOH or lower-alkoxy-C(O), wherein lower-alkyl is optionally substituted with hydroxy, NH$_2$, N(H,lower-alkyl) or N(lower-alkyl)$_2$;
R$^6$ is an aryl or heteroaryl group, which aryl or heteroaryl group is optionally substituted by 1 to 4 substituents selected from the group consisting of halogen, hydroxy, cyano, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H,lower-alkyl)-S(O)$_2$, N(lower-alkyl)$_2$-S(O)$_2$, NH$_2$—C(O), N(H,lower-alkyl)-C(O), N(lower-alkyl)$_2$-C(O), lower-alkoxy-C(O), COOH, 1H-tetrazol-5-yl, 5-oxo-4H-[1,2,4]oxadiazol-3-yl, 5-oxo-4H-[1,2,4]thiadiazol-3-yl, 5-thioxo-4H-[1,2,4]oxadiazol-3-yl, 2-oxo-3H-[1,2,3,5]oxathiadiazol-4-yl, SO$_3$H, 3-hydroxy-isooxazol-5-yl, 6-oxo-6H-pyran-3-yl, 6-oxo-6H-pyran-2-yl, 2-oxo-2H-pyran-3-yl, 2-oxo-2H-pyran-4-yl and P(O)(OCH$_2$CH$_3$)OH, wherein lower-alkyl is optionally substituted with COOH, hydroxy, NH$_2$, N(H,lower-alkyl) or N(lower-alkyl)$_2$, and wherein fluoro-lower-alkyl is optionally substituted with hydroxy;
R$^7$ is hydrogen, halogen, lower-alkyl, lower-alkoxy, fluoro-lower-alkyl, fluoro-lower-alkoxy, hydroxy or hydroxy-lower-alkyl;
R$^8$ and R$^9$ independently from each other are hydrogen or lower-alkyl;
R$^{10}$ is hydrogen, lower-alkyl, cycloalkyl, lower-alkyl-C(O), lower-alkyl-S(O)$_2$, lower-alkoxy-C(O), (lower-alkyl) NH—C(O), or (lower-alkyl)$_2$N—C(O);
R$^{11}$, R$^{12}$, R$^{13}$, R$^{14}$, R$^{15}$, R$^{16}$, R$^{17}$ and R$^{18}$ independently from each other are hydrogen, halogen, hydroxy, lower alkyl, lower-alkoxy, fluoro-lower-alkyl, fluoro-lower-alkoxy, hydroxy-lower-alkyl, aryl, COOH, C(O)O-lower-alkyl or cyano;

and pharmaceutically acceptable salts and esters thereof.

In another embodiment of the present invention, provided is a process for the manufacture of compounds of formula (I), comprising the step of:

reacting a compound of formula (XIV)

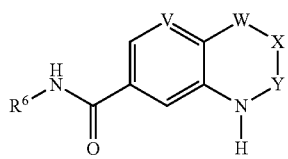

(XIV)

with a compound of formula (XV)

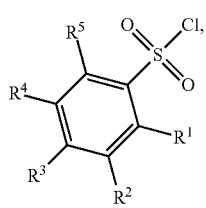

(XV)

or reacting a compound of formula (XVI)

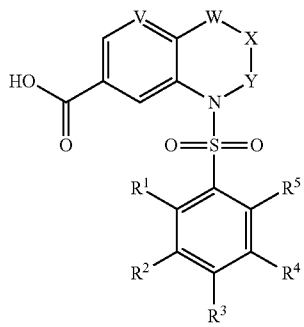

(XVI)

with a compound $R^6$—$NH_2$, wherein $R^1$, $R^2$, $R^3$, $R^4$, $R^5$, $R^6$, V, W, X and Y are as defined above.

In a further embodiment of the present invention, provided is a pharmaceutical composition, comprising a therapeutically effective amount of a compound according to formula I and a pharmaceutically acceptable carrier and/or adjuvant.

In a still another embodiment of the present invention, provided is a method for the therapeutic and/or prophylactic treatment of diseases which are modulated by L-CPT1 inhibitors, comprising the step of administering a therapeutically effective amount of a compound according to formula I to a human being or animal in need thereof.

DETAILED DESCRIPTION

The present invention relates to novel compounds which inhibit liver carnitine palmitoyl transferase 1 (L-CPT1) activity. The compounds of the present invention can be used as pharmaceutically active agents which are useful in the prevention and/or treatment of diseases which are modulated by L-CPT1 inhibitors, particularly diseases which are related to hyperglycemia and/or glucose tolerance disorders. Such diseases include e.g. diabetes and associated pathologies, non insulin dependent diabetes mellitus (also referred to as diabetes type II), obesity, hypertension, insulin resistance syndrome, metabolic syndrome, hyperlipidemia, hypercholesterolemia, fatty liver disease, atherosclerosis, congestive heart failure and renal failure.

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups. Alkyl groups can optionally be substituted with hydroxy, $NH_2$, N(H,lower-alkyl) or N(lower-alkyl)$_2$ or COOH. Unless specifically mentioned, unsubstituted alkyl groups are preferred.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. Lower-alkyl groups can optionally be substituted with hydroxy, $NH_2$, N(H,lower-alkyl), N(lower-alkyl)$_2$. or COOH. Unless specifically mentioned, unsubstituted lower-alkyl groups are preferred. The term "carboxy-lower-alkyl" refers to a lower-alkyl group which is substituted with COOH. The term "hydroxy-lower-alkyl" refers to a lower-alkyl group which is substituted with hydroxy.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H$—$CF_2$.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "acid isostere" refers to groups which have similar steric and electronic features of a carboxylic acid, or that are known in the art to mimic the spatial arrangement and electronic properties of a carboxylic acid. Examples of acid isosteres are 1H-tetrazol-5-yl, 4H-[1,2,4]oxadiazol-3-yl-5-one, 4H-[1,2,4]thiadiazol-3-yl-5-one, 4H-[1,2,4]oxadiazol-3-yl-5-thione, 3H-[1,2,3,5]oxathiadiazol-4-yl-2-oxide, $SO_3H$, 3-hydroxy-isooxazol, 3-hydroxy-pyran-4-one or $P(O)(OCH_2CH_3)OH$.

The term "aryl", alone or in combination, relates to the phenyl or naphthyl group, preferably the phenyl group, which can optionally be substituted, unless specifically stated otherwise, by 1 to 5, preferably 1 to 3, substituents, independently selected from the group consisting of halogen, hydroxy, amino, $NO_2$, lower-alkyl, hydroxy-lower-alkyl, lower-alkoxy, carboxy, carboxy-lower-alkyl, $H_2NC(O)$, (H,lower-alkyl)NC(O), (lower-alkyl)$_2$NC(O), fluoro-lower-alkyl, lower-alkyl-$SO_2$, lower-alkyl-$SO_2O$, lower-alkyl-$SO_2$—NH, lower-alkyl-$SO_2$—N(lower-alkyl), $H_2NSO_2$, (H,lower-alkyl)$NSO_2$, (lower-alkyl)$_2NSO_2$, cyano, heteroaryl, cycloalkyl, phenyl and phenyloxy. Preferred substituents are halogen, lower-alkyl, fluoro-lower-alkyl, lower-alkoxy and fluoro-lower-alkoxy. Furthermore, aryl groups can be substituted as described in the description below.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl, benzoisoxazolyl and quinolinyl. Preferred heteroaryl groups are pyridinyl, pyrazolyl and thiazolyl, more preferably pyridinyl and thiazolyl. Unless specifically stated otherwise, a heteroaryl group may optionally have a substitution pattern as described earlier in connection with the term "aryl". Furthermore, heteroaryl groups can be substituted as described in the description below.

Compounds of formula (I) can form pharmaceutically acceptable salts with bases. Examples of such salts are alkaline, earth-alkaline and ammonium salts such as e.g. sodium, potassium, calcium and trimethylammonium salt. The term "pharmaceutically acceptable salts" refers to such salts.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

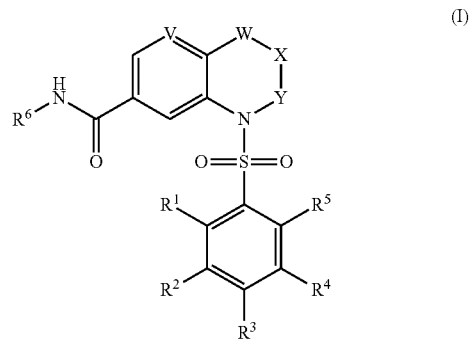

(I)

wherein
V is N or —C($R^7$)—;
W is a single bond or —C($R^8R^9$)—;
X is O, S, SO, $SO_2$ or N($R^{10}$);
Y is —C($R^{11}R^{12}$)—, —C($R^{11}R^{12}$)C($R^{13}R^{14}$)—, —C($R^{11}R^{12}$)C($R^{13}R^{14}$)C($R^{15}R^{16}$)—, —C($R^{11}R^{12}$)C($R^{13}R^{14}$)C($R^{15}R^{16}$)C($R^{17}R^{18}$)— or —C($R^{11}$)═C($R^{12}$)—;
$R^1$, $R^2$, $R^3$, $R^4$ and $R^5$ independently from each other are hydrogen, halogen, cyano, hydroxy, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, $NH_2$—S(O)$_2$, N(H, lower-alkyl)-S(O)$_2$ or N(lower-alkyl)$_2$-S(O)$_2$, $NH_2$—C(O), N(H,lower-alkyl)-C(O), N(lower-alkyl)$_2$-C(O), COOH or lower-alkoxy-C(O), wherein lower-alkyl is optionally substituted with hydroxy, $NH_2$, N(H,lower-alkyl) or N(lower-alkyl)$_2$;
$R^6$ is an aryl or heteroaryl group, which aryl or heteroaryl group is optionally substituted by 1 to 4 substituents selected from the group consisting of halogen, hydroxy, cyano, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, $NH_2$—S(O)$_2$, N(H,lower-alkyl)-S(O)$_2$, N(lower-alkyl)$_2$-S(O)$_2$, $NH_2$—C(O), N(H,lower-alkyl)-C(O), N(lower-alkyl)$_2$-C(O), lower-alkoxy-C(O), COOH, 1H-tetrazol-5-yl, 5-oxo-4H-[1,2,4]oxadiazol-3-yl, 5-oxo-4H-[1,2,4]thiadiazol-3-yl, 5-thioxo-4H-[1,2,4]oxadiazol-3-yl, 2-oxo-3H-[1,2,3,5]oxathiadiazol-4-yl, $SO_3H$, 3-hydroxy-isooxazol-5-yl, 6-oxo-6H-pyran-3-yl, 6-oxo-6H-pyran-2-yl, 2-oxo-2H-pyran-3-yl, 2-oxo-2H-pyran-4-yl and $P(O)(OCH_2CH_3)OH$, wherein lower-alkyl is optionally substituted with COOH, hydroxy, $NH_2$, N(H,lower-alkyl) or N(lower-alkyl)$_2$, and wherein fluoro-lower-alkyl is optionally substituted with hydroxy;
$R^7$ is hydrogen, halogen, lower-alkyl, lower-alkoxy, fluoro-lower-alkyl, fluoro-lower-alkoxy, hydroxy or hydroxy-lower-alkyl;
$R^8$ and $R^9$ independently from each other are hydrogen or lower-alkyl;
$R^{10}$ is hydrogen, lower-alkyl, cycloalkyl, lower-alkyl-C(O), lower-alkyl-S(O)$_2$, lower-alkoxy-C(O), (lower-alkyl)NH—C(O), or (lower-alkyl)$_2$N—C(O);
$R^{11}$, $R^{12}$, $R^{13}$, $R^{14}$, $R^{15}$, $R^{16}$, $R^{17}$ and $R^{18}$ independently from each other are hydrogen, halogen, hydroxy, lower alkyl, lower-alkoxy, fluoro-lower-alkyl, fluoro-lower-alkoxy, hydroxy-lower-alkyl, aryl, COOH, C(O)O-lower-alkyl or cyano;
and pharmaceutically acceptable salts and esters thereof.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C or S atoms and can therefore exist as an enantiomeric mixture, mixture of stereoisomers or as optically pure compounds.

Preferred compounds of formula (I) as defined above are those, wherein $R^{11}$, $R^{12}$, $R^{13}$, $R^{14}$, $R^{15}$, $R^{16}$, $R^{17}$ and $R^{18}$ independently from each other are hydrogen, halogen, hydroxy, lower alkyl, lower-alkoxy, fluoro-lower-alkyl, fluoro-lower-alkoxy, hydroxy-lower-alkyl, aryl or cyano.

In the compounds as described above, such in which V is N are individually preferred and such wherein V is —C($R^7$)— are individually preferred. Compounds wherein V is —C($R^7$)— and $R^7$ is as defined above are particularly preferred. Preferably, W is a single bond.

A preferred embodiment of the present invention relates to compounds as described above, wherein X is O, S, $SO_2$ or N($R^{10}$) and $R^{10}$ is as defined above. Compounds wherein X is O are individually preferred, compounds wherein X is S are individually preferred, compounds wherein X is SO are individually preferred, compounds wherein X is $SO_2$ are individually preferred and compounds wherein X is N($R^{10}$) and $R^{10}$ is as defined above are individually preferred.

Other preferred compounds according to the present invention are those, wherein Y is —C($R^{11}R^{12}$)— or —C($R^{11}R^{12}$)C($R^{13}R^{14}$)—, and $R^{11}$, $R^{12}$, $R^{13}$ and $R^{14}$ are as defined above.

Furthermore, those compounds are preferred, wherein $R^1$, $R^2$, $R^3$, $R^4$ and $R^5$ independently from each other are hydrogen, halogen, lower-alkyl, fluoro-lower-alkyl, lower-alkoxy, fluoro-lower-alkoxy or $NH_2$—C(O). Preferably at least 2 of $R^1$, $R^2$, $R^3$, $R^4$ and $R^5$ are hydrogen, more preferably at least 3, even more preferably at least 4. Preferably, $R^1$, $R^2$, $R^3$, $R^4$ and $R^5$ independently from each other are hydrogen, halogen or lower-alkoxy. Preferably, $R^1$ is lower-alkoxy, more preferably $R^1$ is methoxy. It is preferred, that $R^2$, $R^3$ and $R^5$ are hydrogen. It is also preferred that $R^4$ is halogen, more preferably $R^4$ is chloro.

Another preferred embodiment of the present invention is related to compounds of formula (I) as defined above, wherein $R^6$ is an aryl or heteroaryl group, which aryl or heteroaryl group is optionally substituted by 1 to 4 substituents selected from the group consisting of halogen, cyano, lower-alkyl, carboxy-lower-alkyl, lower-alkoxy, COOH, 1H-tetrazol-5-yl and 5-oxo-4H-[1,2,4]oxadiazol-3-yl. Preferably, $R^6$ is an aryl or heteroaryl group, which aryl or heteroaryl group is optionally substituted by 1 to 4 substituents selected from the group consisting of halogen, lower-alkyl, carboxy-lower-alkyl, lower-alkoxy, COOH, 1H-tetrazol-5-yl and 5-oxo-4H-[1,2,4]oxadiazol-3-yl. More preferably, $R^6$ is a phenyl, pyridinyl, pyrazolyl or thiazolyl group, which group is optionally substituted by 1 to 2 substituents selected from the group consisting of halogen, cyano, lower-alkyl, carboxy-lower-alkyl, lower-alkoxy, COOH, 1H-tetrazol-5-yl and 5-oxo-4H-[1,2,4]oxadiazol-3-yl. More preferably, $R^6$ is a phenyl, pyridinyl or thiazolyl group, which group is optionally substituted by 1 to 2 substituents selected from the group consisting of halogen, lower-alkyl, carboxy-lower-alkyl, lower-alkoxy, COOH, 1H-tetrazol-5-yl and 5-oxo-4H-[1,2,4]oxadiazol-3-yl. More preferably, $R^6$ is a phenyl, pyridinyl or thiazolyl group, which group is optionally substituted by 1 to 2 substituents selected from the group consisting of halogen, carboxy-lower-alkyl and COOH, more preferably halogen and COOH. Most preferably, $R^6$ is 4-carboxy-phenyl, 3-fluoro-4-carboxy-phenyl, 3-chloro-4-carboxy-phenyl, 2-carboxy-pyridin-5-yl, 4-carboxy-methylphenyl, 4-carboxy-methyl-thiazol-2-yl or 2-carboxy-methyl-thiazol-4-yl.

Other preferred compounds of the present invention are those, wherein $R^7$ is hydrogen, halogen, lower-alkyl, lower-alkoxy or fluoro-lower-alkoxy. Preferably, $R^7$ is hydrogen or halogen. More preferably, $R^7$ is hydrogen or fluoro. Furthermore, it is preferred that $R^8$ and $R^9$ are hydrogen. It is also preferred that $R^{10}$ is hydrogen.

Other preferred compounds according to the present invention are those, wherein $R^{11}$, $R^{12}$, $R^{13}$, $R^{14}$, $R^{15}$, $R^{16}$, $R^{17}$ and $R^{18}$ independently from each other are hydrogen or phenyl. More preferably, $R^{11}$, $R^{12}$, $R^{13}$, $R^{14}$, $R^{15}$, $R^{16}$, $R^{17}$ and $R^{18}$ are hydrogen. Furthermore, it is preferred that $R^{11}$, $R^{12}$, $R^{13}$, $R^{14}$, $R^{15}$, $R^{16}$, $R^{17}$ and $R^{18}$ are hydrogen, COOH or C(O)O-lower-alkyl. Preferably, not more than one of $R^{11}$, $R^{12}$, $R^{13}$, $R^{14}$, $R^{15}$, $R^{16}$, $R^{17}$ and $R^{18}$ is phenyl, COOH or C(O)O-lower-alkyl.

In particular, preferred compounds are the compounds of formula (I) described in the examples as individual compounds as well as pharmaceutically acceptable salts as well as pharmaceutically acceptable esters thereof.

Preferred compounds of formula (I) are those selected from the group consisting of:
4-{[4-(5-Chloro-2-methoxy-benzenesulfonyl)-3,4-dihydro-2H-benzo[1,4]oxazine-6-carbonyl]-amino}-benzoic acid,
4-{[4-(5-Chloro-2-methoxy-benzenesulfonyl)-3,4-dihydro-2H-benzo[1,4]oxazine-6-carbonyl]-amino}-2-fluoro-benzoic acid,
2-Chloro-4-{[4-(5-chloro-2-methoxy-benzenesulfonyl)-3,4-dihydro-2H-benzo[1,4]oxazine-6-carbonyl]-amino}-benzoic acid,
5-{[4-(5-Chloro-2-methoxy-benzenesulfonyl)-3,4-dihydro-2H-benzo[1,4]oxazine-6-carbonyl]-amino}-pyridine-2-carboxylic acid,
4-{[4-(5-Chloro-2-methoxy-benzenesulfonyl)-3,4-dihydro-2H-benzo[1,4]oxazine-6-carbonyl]-amino}-2-methoxy-benzoic acid,
4-{[4-(5-Chloro-2-methoxy-benzenesulfonyl)-3,4-dihydro-2H-benzo[1,4]oxazine-6-carbonyl]-amino}-2-methyl-benzoic acid,
4-{[4-(5-Chloro-2-methoxy-benzenesulfonyl)-3,4-dihydro-2H-benzo[1,4]oxazine-6-carbonyl]-amino}-3-methyl-benzoic acid,
2-{[4-(5-Chloro-2-methoxy-benzenesulfonyl)-3,4-dihydro-2H-benzo[1,4]oxazine-6-carbonyl]-amino}-thiazole-4-carboxylic acid,
4-(5-Chloro-2-methoxy-benzenesulfonyl)-3,4-dihydro-2H-benzo[1,4]oxazine-6-carboxylic acid [4-(1H-tetrazol-5-yl)-phenyl]-amide,
4-(5-Chloro-2-methoxy-benzenesulfonyl)-3,4-dihydro-2H-benzo[1,4]oxazine-6-carboxylic acid [4-(5-oxo-4,5-dihydro-[1,2,4]oxadiazol-3-yl)-phenyl]-amide,
4-{[4-(5-Chloro-2-methoxy-benzenesulfonyl)-1,2,3,4-tetrahydro-quinoxaline-6-carbonyl]-amino}-benzoic acid,
5-{[4-(5-Chloro-2-methoxy-benzenesulfonyl)-1,2,3,4-tetrahydro-quinoxaline-6-carbonyl]-amino}-pyridine-2-carboxylic acid,
4-{[4-(5-Chloro-2-methoxy-benzenesulfonyl)-1,2,3,4-tetrahydro-quinoxaline-6-carbonyl]-amino}-2-fluoro-benzoic acid,
4-{[4-(3-Fluoro-benzenesulfonyl)-3,4-dihydro-2H-benzo[1,4]oxazine-6-carbonyl]-amino}-benzoic acid,
4-{[4-(2,5-Difluoro-benzenesulfonyl)-3,4-dihydro-2H-benzo[1,4]oxazine-6-carbonyl]-amino}-benzoic acid,
4-{[4-(5-Fluoro-2-methyl-benzenesulfonyl)-3,4-dihydro-2H-benzo[1,4]oxazine-6-carbonyl]-amino}-benzoic acid, 4-{[4-(3-Difluoromethoxy-benzenesulfonyl)-3,4-dihydro-2H-benzo[1,4]oxazine-6-carbonyl]-amino}-benzoic acid, 4-{[4-(3,5-Dimethyl-benzenesulfonyl)-3,4-dihydro-2H-benzo[1,4]oxazine-6-carbonyl]-amino}-benzoic acid, 4-{[4-(3-Trifluoromethyl-benzenesulfonyl)-3,4-dihydro-2H-benzo[1,4]oxazine-6-carbonyl]-amino}-benzoic acid, 4-{[4-(3-Chloro-benzenesulfonyl)-3,4-dihydro-2H-benzo[1,4]oxazine-6-carbonyl]-amino}-benzoic acid, 2-Fluoro-4-{[4-(3-trifluoromethyl-benzenesulfonyl)-3,4-dihydro-2H-benzo[1,4]oxazine-6-carbonyl]-amino}-benzoic acid, 4-{[4-(3-Chloro-benzenesulfonyl)-3,4-dihydro-2H-benzo[1,4]oxazine-6-carbonyl]-amino}-2-fluoro-benzoic acid, 2-Fluoro-4-{[4-(3-fluoro-benzenesulfonyl)-3,4-dihydro-2H-benzo[1,4]oxazine-6-carbonyl]-amino}-benzoic acid, 4-{[4-(2,5-Difluoro-benzenesulfonyl)-3,4-dihydro-2H-benzo[1,4]oxazine-6-carbonyl]-amino}-2-fluoro-benzoic acid, 2-Fluoro-4-{[4-(5-fluoro-2-methyl-benzenesulfonyl)-3,4-dihydro-2H-benzo[1,4]oxazine-6-carbonyl]-amino}-benzoic acid, 4-{[4-(3-Difluoromethoxy-benzenesulfonyl)-3,4-dihydro-2H-benzo[1,4]oxazine-6-carbonyl]-amino}-2-fluoro-benzoic acid, 4-{[4-(3,5-Dimethyl-benzenesulfonyl)-3,4-dihydro-2H-benzo[1,4]oxazine-6-carbonyl]-amino}-2-fluoro-benzoic acid, 4-{[4-(3-Carbamoyl-benzenesulfonyl)-3,4-dihydro-2H-benzo[1,4]oxazine-6-carbonyl]-amino}-2-fluoro-benzoic acid, 6-{[4-(5-Chloro-2-methoxy-benzenesulfonyl)-3,4-dihydro-2H-benzo[1,4]oxazine-6-carbonyl]-amino}-nicotinic acid, 2-Chloro-4-{[3-(5-chloro-2-methoxy-benzenesulfonyl)-2,3-dihydro-benzooxazole-5-carbonyl]-amino}-benzoic acid, 4-{[3-(5-Chloro-2-methoxy-benzenesulfonyl)-2,3-dihydro-benzooxazole-5-carbonyl]-amino}-benzoic acid, 4-{[3-(5-Chloro-2-methoxy-benzenesulfonyl)-2,3-dihydro-benzooxazole-5-carbonyl]-amino}-2-fluoro-benzoic acid, 3-(5-Chloro-2-methoxy-benzenesulfonyl)-2,3-dihydro-benzooxazole-5-carboxylic acid phenylamide, 3-(5-Chloro-2-methoxy-benzenesulfonyl)-2,3-dihydro-benzooxazole-5-carboxylic acid pyridin-3-ylamide, 4-{[3-(5-Chloro-2-methoxy-benzenesulfonyl)-2-phenyl-2,3-dihydro-benzooxazole-5-carbonyl]-amino}-benzoic acid, 4-{[9-(5-Chloro-2-methoxy-benzenesulfonyl)-6,7,8,9-tetrahydro-5-oxa-9-aza-benzocycloheptene-2-carbonyl]-amino}-benzoic acid, 2-Chloro-4-{[9-(5-chloro-2-methoxy-benzenesulfonyl)-6,7,8,9-tetrahydro-5-oxa-9-aza-benzocycloheptene-2-carbonyl]-amino}-benzoic acid, 4-{[6-(5-Chloro-2-methoxy-benzenesulfonyl)-3,4,5,6-tetrahydro-2H-benzo[b][1,4]oxazocine-8-carbonyl]-amino}-benzoic acid, 2-Chloro-4-{[6-(5-chloro-2-methoxy-benzenesulfonyl)-3,4,5,6-tetrahydro-2H-benzo[b][1,4]oxazocine-8-carbonyl]-amino}-benzoic acid, 4-{[3-(5-Chloro-2-methoxy-benzenesulfonyl)-7-trifluoromethyl-2,3-dihydro-benzooxazole-5-carbonyl]-amino}-benzoic acid, 4-{[4-(5-Chloro-2-methoxy-benzenesulfonyl)-8-trifluoromethyl-3,4-dihydro-2H-benzo[1,4]oxazine-6-carbonyl]-amino}-benzoic acid, 4-{[3-(5-Chloro-2-methoxy-benzenesulfonyl)-7-methoxy-2,3-dihydro-benzooxazole-5-carbonyl]-amino}-benzoic acid, 4-{[4-(5-Chloro-2-methoxy-benzenesulfonyl)-8-methoxy-3,4-dihydro-2H-benzo[1,4]oxazine-6-carbonyl]-amino}-benzoic acid, 4-{[3-(5-Chloro-2-methoxy-benzenesulfonyl)-7-fluoro-2,3-dihydro-benzooxazole-5-carbonyl]-amino}-benzoic acid, 2-Chloro-4-{[3-(5-chloro-2-methoxy-benzenesulfonyl)-7-fluoro-2,3-dihydro-benzooxazole-5-carbonyl]-amino}-benzoic acid, 4-{[3-(5-Chloro-2-methoxy-benzenesulfonyl)-7-fluoro-2,3-dihydro-benzooxazole-5-carbonyl]-amino}-2-fluoro-benzoic acid, 4-{[4-(5-Chloro-2-methoxy-benzenesulfonyl)-8-fluoro-3,4-dihydro-2H-benzo[1,4]oxazine-6-carbonyl]-amino}-benzoic acid, 2-Chloro-4-{[4-(5-chloro-2-methoxy-benzenesulfonyl)-8-fluoro-3,4-dihydro-2H-benzo[1,4]oxazine-6-carbonyl]-amino}-benzoic acid, 4-{[4-(5-Chloro-2-methoxy-benzenesulfonyl)-8-fluoro-3,4-dihydro-2H-benzo[1,4]oxazine-6-carbonyl]-amino}-2-fluoro-benzoic acid, 4-{[7-Chloro-3-(5-chloro-2-methoxy-benzenesulfonyl)-2,3-dihydro-benzooxazole-5-carbonyl]-amino}-benzoic acid, 4-{[8-Chloro-4-(5-chloro-2-methoxy-benzenesulfonyl)-3,4-dihydro-2H-benzo[1,4]oxazine-6-carbonyl]-amino}-benzoic acid, 4-{[3-(5-Chloro-2-methoxy-benzenesulfonyl)-7-methyl-2,3-dihydro-benzooxazole-5-carbonyl]-amino}-benzoic acid, 4-{[4-(5-Chloro-2-methoxy-benzenesulfonyl)-8-methyl-3,4-dihydro-2H-benzo[1,4]oxazine-6-carbonyl]-amino}-benzoic acid, 3-(5-Chloro-2-methoxy-benzenesulfonyl)-2,3-dihydro-benzooxazole-5-carboxylic acid (4-fluorophenyl)-amide, 4-{[4-(5-Chloro-2-methoxy-benzenesulfonyl)-3,4-dihydro-2H-benzo[1,4]thiazine-6-carbonyl]-amino}-benzoic acid, 4-{[1-(5-Chloro-2-methoxy-benzenesulfonyl)-2,3-dihydro-1H-4-oxa-1,5-diaza-naphthalene-7-carbonyl]-amino}-benzoic acid, 1-(5-chloro-2-methoxy-benzenesulfonyl)-2,3-dihydro-1H-4-oxa-1,5-diaza-naphthalene-7-carboxylic acid phenylamide, 4-(5-Chloro-2-methoxy-benzenesulfonyl)-4H-benzo[1,4]oxazine-6-carboxylic acid phenylamide, (2-{[3-(5-Chloro-2-methoxy-benzenesulfonyl)-2,3-dihydro-benzooxazole-5-carbonyl]-amino}-thiazol-4-yl)-acetic acid, (3-{[3-(5-Chloro-2-methoxy-benzenesulfonyl)-2,3-dihydro-benzooxazole-5-carbonyl]-amino}-phenyl)-acetic acid, (4-{[3-(5-Chloro-2-methoxy-benzenesulfonyl)-2,3-dihydro-benzooxazole-5-carbonyl]-amino}-phenyl)-acetic acid, (2-{[4-(5-Chloro-2-methoxy-benzenesulfonyl)-8-fluoro-3,4-dihydro-2H-benzo[1,4]oxazine-6-carbonyl]-amino}-thiazol-4-yl)-acetic acid, (4-{[4-(5-Chloro-2-methoxy-benzenesulfonyl)-8-fluoro-3,4-dihydro-2H-benzo[1,4]oxazine-6-carbonyl]-amino}-phenyl)-acetic acid, (2-{[3-(5-Chloro-2-methoxy-benzenesulfonyl)-7-fluoro-2,3-dihydro-benzooxazole-5-carbonyl]-amino}-thiazol-4-yl)-acetic acid, (4-{[3-(5-Chloro-2-methoxy-benzenesulfonyl)-7-fluoro-2,3-dihydro-benzooxazole-5-carbonyl]-amino}-phenyl)-acetic acid, (2-{[4-(5-Chloro-2-methoxy-benzenesulfonyl)-3,4-dihydro-2H-benzo[1,4]oxazine-6-carbonyl]-amino}-thiazol-4-yl)-acetic acid, (4-{[4-(5-Chloro-2-methoxy-benzenesulfonyl)-3,4-dihydro-2H-benzo[1,4]oxazine-6-carbonyl]-amino}-phenyl)-acetic acid,
(2-{[4-(5-Chloro-2-methoxy-benzenesulfonyl)-3,4-dihydro-2H-benzo[1,4]thiazine-6-carbonyl]-amino}-thiazol-4-yl)-acetic acid,
(4-{[4-(5-Chloro-2-methoxy-benzenesulfonyl)-3,4-dihydro-2H-benzo[1,4]thiazine-6-carbonyl]-amino}-phenyl)-acetic acid,
4-{[4-(5-Chloro-2-methoxy-benzenesulfonyl)-1,1-dioxo-1,2,3,4-tetrahydro-benzo[1,4]thiazine-6-carbonyl]-amino}-benzoic acid,
4-(5-Chloro-2-methoxy-benzenesulfonyl)-3,4-dihydro-2H-benzo[1,4]oxazine-6-carboxylic acid phenylamide,
3-{[4-(5-Chloro-2-methoxy-benzenesulfonyl)-3,4-dihydro-2H-benzo[1,4]oxazine-6-carbonyl]-amino}-benzoic acid,
4-{[1-(5-Chloro-2-methoxy-benzenesulfonyl)-1,4-dihydro-2H-benzo[d][1,3]oxazine-7-carbonyl]-amino}-benzoic acid,
(2-{[1-(5-Chloro-2-methoxy-benzenesulfonyl)-1,4-dihydro-2H-benzo[d][1,3]oxazine-7-carbonyl]-amino}-thiazol-4-yl)-acetic acid, and
(4-{[1-(5-Chloro-2-methoxy-benzenesulfonyl)-1,4-dihydro-2H-benzo[d][1,3]oxazine-7-carbonyl]-amino}-phenyl)-acetic acid,
and pharmaceutically acceptable salts and esters thereof.

Particularly preferred compounds of formula (I) are those selected from the group consisting of:
4-{[4-(5-Chloro-2-methoxy-benzenesulfonyl)-3,4-dihydro-2H-benzo[1,4]oxazine-6-carbonyl]-amino}-benzoic acid,
4-{[4-(5-Chloro-2-methoxy-benzenesulfonyl)-3,4-dihydro-2H-benzo[1,4]oxazine-6-carbonyl]-amino}-2-fluoro-benzoic acid,
2-Chloro-4-{[4-(5-chloro-2-methoxy-benzenesulfonyl)-3,4-dihydro-2H-benzo[1,4]oxazine-6-carbonyl]-amino}-benzoic acid,
5-{[4-(5-Chloro-2-methoxy-benzenesulfonyl)-3,4-dihydro-2H-benzo[1,4]oxazine-6-carbonyl]-amino}-pyridine-2-carboxylic acid,
4-{[4-(5-Chloro-2-methoxy-benzenesulfonyl)-1,2,3,4-tetrahydro-quinoxaline-6-carbonyl]-amino}-benzoic acid,
2-Chloro-4-{[3-(5-chloro-2-methoxy-benzenesulfonyl)-2,3-dihydro-benzooxazole-5-carbonyl]-amino}-benzoic acid,
4-{[3-(5-Chloro-2-methoxy-benzenesulfonyl)-2,3-dihydro-benzooxazole-5-carbonyl]-amino}-2-fluoro-benzoic acid,
4-{[4-(5-Chloro-2-methoxy-benzenesulfonyl)-8-fluoro-3,4-dihydro-2H-benzo[1,4]oxazine-6-carbonyl]-amino}-benzoic acid,
(2-{[3-(5-Chloro-2-methoxy-benzenesulfonyl)-2,3-dihydro-benzooxazole-5-carbonyl]-amino}-thiazol-4-yl)-acetic acid,
(4-{[4-(5-Chloro-2-methoxy-benzenesulfonyl)-8-fluoro-3,4-dihydro-2H-benzo[1,4]oxazine-6-carbonyl]-amino}-phenyl)-acetic acid,
(2-{[4-(5-Chloro-2-methoxy-benzenesulfonyl)-3,4-dihydro-2H-benzo[1,4]thiazine-6-carbonyl]-amino}-thiazol-4-yl)-acetic acid, and
4-{[4-(5-Chloro-2-methoxy-benzenesulfonyl)-1,1-dioxo-1,2,3,4-tetrahydro-benzo[1,4]thiazine-6-carbonyl]-amino}-benzoic acid,
and pharmaceutically acceptable salts and esters thereof.

Other preferred compounds of formula (I) are those selected from the group consisting of:
2-Chloro-5-{[4-(5-chloro-2-methoxy-benzenesulfonyl)-3,4-dihydro-2H-benzo[1,4]oxazine-6-carbonyl]-amino}-benzoic acid,
(2-{[4-(5-Chloro-2-methoxy-benzenesulfonyl)-8-trifluoromethyl-3,4-dihydro-2H-benzo[1,4]oxazine-6-carbonyl]-amino}-thiazol-4-yl)-acetic acid,
(4-{[4-(5-Chloro-2-methoxy-benzenesulfonyl)-8-trifluoromethyl-3,4-dihydro-2H-benzo[1,4]oxazine-6-carbonyl]-amino}-phenyl)-acetic acid,
(2-{[4-(5-Chloro-2-methoxy-benzenesulfonyl)-8-methyl-3,4-dihydro-2H-benzo[1,4]oxazine-6-carbonyl]-amino}-thiazol-4-yl)-acetic acid,
(4-{[3-(5-Chloro-2-methoxy-benzenesulfonyl)-7-methyl-2,3-dihydro-benzooxazole-5-carbonyl]-amino}-phenyl)-acetic acid,
(2-{[3-(5-Chloro-2-methoxy-benzenesulfonyl)-7-methyl-2,3-dihydro-benzooxazole-5-carbonyl]-amino}-thiazol-4-yl)-acetic acid,
(4-{[4-(5-Chloro-2-methoxy-benzenesulfonyl)-8-methyl-3,4-dihydro-2H-benzo[1,4]oxazine-6-carbonyl]-amino}-phenyl)-acetic acid,
(2-{[4-(5-Chloro-2-methoxy-benzenesulfonyl)-3,4-dihydro-2H-benzo[1,4]oxazine-6-carbonyl]-amino}-thiazol-5-yl)-acetic acid,
2-{[4-(5-Chloro-2-methoxy-benzenesulfonyl)-3,4-dihydro-2H-benzo[1,4]oxazine-6-carbonyl]-amino}-thiazole-5-carboxylic acid,
(3-{[4-(5-Chloro-2-methoxy-benzenesulfonyl)-3,4-dihydro-2H-benzo[1,4]oxazine-6-carbonyl]-amino}-phenyl)-acetic acid,
3-(4-{[445-Chloro-2-methoxy-benzenesulfonyl)-3,4-dihydro-2H-benzo[1,4]oxazine-6-carbonyl]-amino}-phenyl)-propionic acid,
(2-{[4-(5-Chloro-2-methoxy-benzenesulfonyl)-3,4-dihydro-2H-benzo[1,4]oxazine-6-carbonyl]-amino}-5-methyl-thiazol-4-yl)-acetic acid,
(3-{[4-(5-Chloro-2-methoxy-benzenesulfonyl)-3,4-dihydro-2H-benzo[1,4]oxazine-6-carbonyl]-amino}-pyrazol-1-yl)-acetic acid,
4-{[4-(5-Chloro-2-methoxy-benzenesulfonyl)-3,4-dihydro-2H-benzo[1,4]oxazine-6-carbonyl]-amino}-2-cyano-benzoic acid,
2-Fluoro-4-{[4-(2-methoxy-5-methyl-benzenesulfonyl)-3,4-dihydro-2H-benzo[1,4]oxazine-6-carbonyl]-amino}-benzoic acid,
(2-{[4-(Toluene-3-sulfonyl)-3,4-dihydro-2H-benzo[1,4]oxazine-6-carbonyl]-amino}-thiazol-4-yl)acetic acid,
(2-{[4-(3-Chloro-benzenesulfonyl)-3,4-dihydro-2H-benzo[1,4]oxazine-6-carbonyl]-amino}-thiazol-4-yl)-acetic acid,
(2-{[4-(3,5-Dimethyl-benzenesulfonyl)-3,4-dihydro-2H-benzo[1,4]oxazine-6-carbonyl]-amino}-thiazol-4-yl)-acetic acid,
(3-{[3-(5-Chloro-2-methoxy-benzenesulfonyl)-2,3-dihydro-benzooxazole-5-carbonyl]-amino}-pyrazol-1-yl)-acetic acid,
4-{[4-(3-Chloro-benzenesulfonyl)-3,4-dihydro-2H-benzo[1,4]thiazine-6-carbonyl]-amino}-benzoic acid,
4-{[4-(3-Chloro-benzenesulfonyl)-1-oxo-1,2,3,4-tetrahydro-benzo[1,4]thiazine-6-carbonyl]-amino}-benzoic acid,
4-{[4-(3-Chloro-benzenesulfonyl)-1,1-dioxo-1,2,3,4-tetrahydro-benzo[1,4]thiazine-6-carbonyl]-amino}-benzoic acid,
4-{[4-(3,5-Dimethyl-benzenesulfonyl)-3,4-dihydro-2H-benzo[1,4]thiazine-6-carbonyl]-amino}-benzoic acid,
4-{[4-(3,5-Dimethyl-benzenesulfonyl)-1-oxo-1,2,3,4-tetrahydro-benzo[1,4]thiazine-6-carbonyl]-amino}-benzoic acid, 4-{[4-(3,5-Dimethyl-benzenesulfonyl)-1,1-dioxo-1,2,3,4-tetrahydro-benzo[1,4]thiazine-6-carbonyl]-amino}-benzoic acid, 4-{[4-(5-Chloro-2-methoxy-benzenesulfonyl)-1-oxo-1,2,3,4-tetrahydro-benzo[1,4]thiazine-6-carbonyl]-amino}-benzoic acid, (4-{[4-(5-Chloro-2-methoxy-benzenesulfonyl)-1-oxo-1,2,3,4-tetrahydro-benzo[1,4]thiazine-6-carbonyl]-amino}-phenyl)-acetic acid, (4-{[4-(5-Chloro-2-methoxy-benzenesulfonyl)-1,1-dioxo-1,2,3,4-tetrahydro-benzo[1,4]thiazine-6-carbonyl]-amino}-phenyl)-acetic acid, 4-{[4-(5-Chloro-2-methoxy-benzenesulfonyl)-3,4-dihydro-2H-benzo[1,4]thiazine-6-carbonyl]-amino}-2-fluoro-benzoic acid, 4-{[4-(5-Chloro-2-methoxy-benzenesulfonyl)-1,1-dioxo-1,2,3,4-tetrahydro-benzo[1,4]thiazine-6-carbonyl]-amino}-2-fluoro-benzoic acid, 2-Chloro-4-{[4-(5-chloro-2-methoxy-benzenesulfonyl)-3,4-dihydro-2H-benzo[1,4]thiazine-6-carbonyl]-amino}-benzoic acid, 2-Chloro-4-{[4-(5-chloro-2-methoxy-benzenesulfonyl)-1,1-dioxo-1,2,3,4-tetrahydro-benzo[1,4]thiazine-6-carbonyl]-amino}-benzoic acid, 4-(5-Chloro-2-methoxy-benzenesulfonyl)-6-phenylcarbamoyl-3,4-dihydro-2H-benzo[1,4]oxazine-2-carboxylic acid ethyl ester, 4-(5-Chloro-2-methoxy-benzenesulfonyl)-6-phenylcarbamoyl-3,4-dihydro-2H-benzo[1,4]oxazine-2-carboxylic acid, 4-(5-Chloro-2-methoxy-benzenesulfonyl)-6-(2-fluoro-phenylcarbamoyl)-3,4-dihydro-2H-benzo[1,4]oxazine-2-carboxylic acid ethyl ester, 4-(5-Chloro-2-methoxy-benzenesulfonyl)-6-(2-fluoro-phenylcarbamoyl)-3,4-dihydro-2H-benzo[1,4]oxazine-2-carboxylic acid, 4-(5-Chloro-2-methoxy-benzenesulfonyl)-6-(3-fluoro-phenylcarbamoyl)-3,4-dihydro-2H-benzo[1,4]oxazine-2-carboxylic acid ethyl ester, 4-(5-Chloro-2-methoxy-benzenesulfonyl)-6-(3-fluoro-phenylcarbamoyl)-3,4-dihydro-2H-benzo[1,4]oxazine-2-carboxylic acid, 4-(5-Chloro-2-methoxy-benzenesulfonyl)-6-(4-fluoro-phenylcarbamoyl)-3,4-dihydro-2H-benzo[1,4]oxazine-2-carboxylic acid ethyl ester, and 4-(5-Chloro-2-methoxy-benzenesulfonyl)-6-(4-fluoro-phenylcarbamoyl)-3,4-dihydro-2H-benzo[1,4]oxazine-2-carboxylic acid and pharmaceutically acceptable salts and esters thereof.

Other particularly preferred compounds of formula (I) are those selected from the group consisting of:

(2-{[4-(5-Chloro-2-methoxy-benzenesulfonyl)-8-methyl-3,4-dihydro-2H-benzo[1,4]oxazine-6-carbonyl]-amino}-thiazol-4-yl)-acetic acid, and (4-{[4-(5-Chloro-2-methoxy-benzenesulfonyl)-8-methyl-3,4-dihydro-2H-benzo[1,4]oxazine-6-carbonyl]-amino}-phenyl)-acetic acid and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises
reacting a compound of formula (XIV)

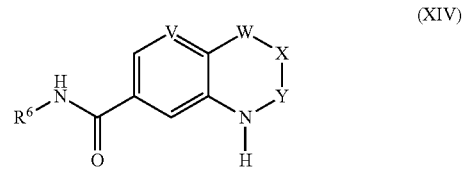

with a compound of formula (XV)

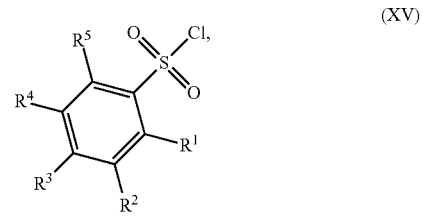

or
reacting a compound of formula (XVI)

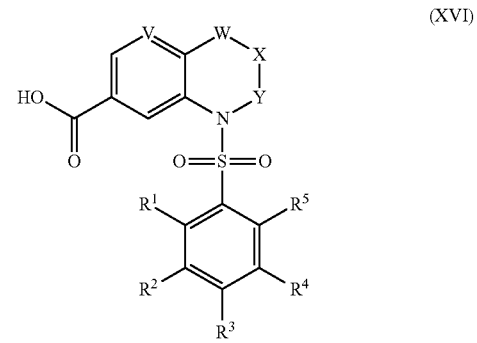

with a compound $R^6$—$NH_2$,
wherein $R^1$, $R^2$, $R^3$, $R^4$, $R^5$, $R^6$, V, W, X and Y are as defined above.

The reaction of a compound of formula (XIV) with a compound of formula (XV) can be carried out under conditions well known to the person skilled in the art. Such reactions of a compound of formula (XIV) can conveniently be carried out for example by mixing a compound of formula (XIV) with a compound of formula (XV) in anhydrous solvents such as e.g. dichloromethane, tetrahydrofuran, acetonitrile, toluene and mixtures thereof at appropriate temperatures between 0° C. and 110° C., optionally in the presence of a base, as for example triethylamine, diisopropylethylamine or pyridine.

The reaction of a compound of formula (XVI) with a compound $R^6$—$NH_2$ can be carried out under conditions well known to the person skilled in the art. Such reactions can conveniently be carried out for example by mixing a compound of formula (XVI) with a compound $R^6$—$NH_2$ in aprotic solvents such as dichloromethane, tetrahydrofuran, N,N-dimethylformamide, N-methylpyrrolidinone and mixtures thereof at temperatures between 0° C. and 60° C. in the presence or absence of a base such as triethylamine or N,N- diisopropylethylamine, and a condensing agent. Appropriate condensing agents can be for example O-(7-benzotriazol-1-yl)-N,N,N',N'-tetramethyluronium-tetrafluoroborate (TBTU), O-(7-azabenzotriazol-1-yl)-N,N,N',N'-tetramethyluronium-hexafluorophosphate (HATU), N,N'-dicyclohexyl-carbodiimide, 1-(3-dimethylaminopropyl)-3-ethyl-carbodiimide hydrochloride, O-(benzotriazol-1-yl)-N,N,N',N'-tetramethyluronium hexafluoro-phosphate, bromo-tris-pyrrolidino-phosphonium hexafluorophosphate or others well known to the person skilled in the art. Alternatively, such reactions can be performed in two steps involving first formation of the acyl halide derivative of the compound of formula (XVI) and subsequent coupling reaction with an amine $R^6$—$NH_2$ in the presence of a base. Typically employed reagents for the formation of the acyl chloride are thionyl chloride, phosphorous pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, diisopropyl ethyl amine or N-methyl morpholine. The obtained acyl chloride can be isolated or reacted as such with an appropriate amine $R^6$—$NH_2$ in an aprotic solvent, like dichloromethane, tetrahydrofuran or acetone, in the presence of a base. Typical bases are triethylamine, 4-methylmorpholine, pyridine, diisopropyl ethyl amine or dimethylaminopyridine or mixtures thereof.

The present invention also relates to compounds of formula (I) as defined above, when prepared by a process as described above.

The compounds of formula (I), (XIV), (XV), (XVI) and $R^6$—$NH_2$ can be prepared by methods known in the art or as described below or in analogy thereto. Unless otherwise indicated, $R^1$, $R^2$, $R^3$, $R^4$, $R^5$, $R^6$, V, W, X and Y are as described above.

Compounds of formula I, wherein V is C—$R^7$, W is a single bond, X is O and
Y is —C($R^{11}R^{12}$)C($R^{13}R^{14}$)— are part of the present invention and can be represented by formula II:

Compounds of general formula II can be accessed according to the following general scheme 1:

Scheme 1

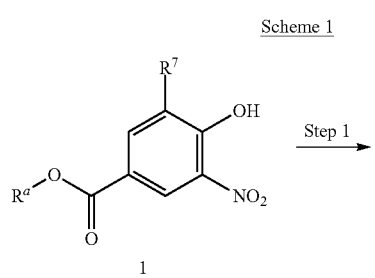

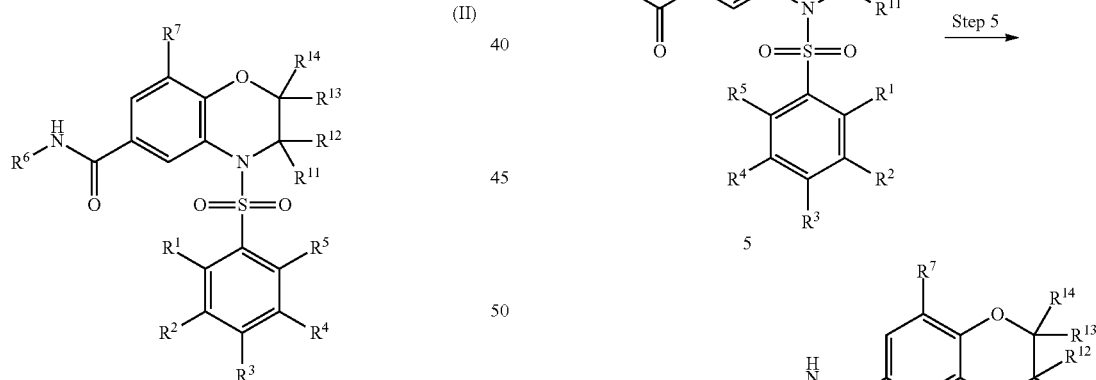

In step 1, scheme 1, a 4-hydroxy-3-nitro-benzoic acid alkyl ester 1 ($R^a$=lower alkyl, e.g., methyl or ethyl) is converted to the corresponding amine 2 using methods well known to those skilled in the art, e.g. nitro reduction. The reaction is typically carried out in solvents such as ethanol, methanol, water under an atmosphere of hydrogen at a pressure of 1 to 50 bar and temperatures between 0° C. and 100° C. with catalysts such as palladium, platinum or platinum oxide. Alternatively, the reaction can be carried out using reducing metals like for example tin or tin chloride in the presence of concentrated mineral acids like hydrochloric or sulfuric acid, or with Ni/Raney.

In step 2, scheme 1, aminophenol 2 is converted to the corresponding 3,4-dihydro-2H-benzo[1,4]oxazine 3 using methods well known to those skilled in the art, e.g. double nucleophilic substitution with an appropriately substituted 1,2-dibromoethane or 1,2-bis(alkyl-/arylsulfonyloxy)-ethane derivative. The reaction is typically carried out in an aprotic solvent like dimethylformamide, acetone, tetrahydrofuran in the presence of a base like for example potassium carbonate, sodium carbonate or cesium carbonate at temperatures between 0° C. and 100° C.

In step 3, scheme 1, the obtained compound of general formula 3 is converted into the sulfonamide analogue of general formula 4, using methods well known to someone skilled in the art, e.g. sulfonylation of amines with sulfonyl chlorides. The reaction is typically carried out in solvents such as dichloromethane, tetrahydrofuran, acetonitrile, toluene, pyridine, triethylamine, or mixtures thereof, at temperatures between 0° C. and 110° C.

In step 4, scheme 1, the 3,4-dihydro-2H-benzo[1,4]oxazine-6-carboxylic acid alkyl ester 4 is converted into the corresponding carboxylic acid of the formula 5, using methods well known to someone skilled in the art, e.g. base mediated ester hydrolysis. The reaction is typically carried out in solvents such as water, methanol, ethanol, tetrahydrofuran and mixtures thereof at temperatures between −20° C. and 120° C. Typical reagents are aqueous or anhydrous lithium hydroxide, lithium hydroxide monohydrate, sodium hydroxide, potassium hydroxide, sodium hydrogen carbonate, sodium carbonate, potassium hydrogen carbonate and potassium carbonate.

In step 5, scheme 1, the carboxylic acid derivative of the formula 5 is converted, with the appropriate amine $R^6$—$NH_2$, into the corresponding amide of general formula II, using methods well known to someone skilled in the art e.g. amide formation using a coupling reagent. The reaction is typically carried out in aprotic solvents such as dichloromethane, tetrahydrofuran, N,N-dimethylformamide, N-methylpyrrolidinone and mixtures thereof at temperatures between 0° C. and 80° C. in the presence or absence of a base such as triethylamine, diisopropylethylamine, 4-methylmorpholine, and/or 4-(dimethylamino)pyridine. Typically used coupling agents are N,N'-dicyclohexylcarbodiimide, 1-(3-dimethylaminopropyl)-3-ethyl-carbodiimide hydrochloride, O(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate and bromo-tris-pyrrolidino-phosphonium hexafluorophosphate. Alternatively, such reaction can be performed in two steps involving first formation of the acyl halide derivative of 4 and subsequent coupling reaction with an appropriate amine in the presence of a base. Typically employed reagents for the formation of the acyl chloride are thionyl chloride, phosphorous pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, diisopropylethylamine or 4-methylmorpholine. The obtained acyl chloride can be iso- lated or reacted as such with amine $R^6$—$NH_2$ in an aprotic solvent, like dichloromethane, tetrahydrofuran or acetone, in the presence of a base. Typical bases are triethylamine, 4-methylmorpholine, pyridine, diisopropylethylamine or 4-(dimethylamino)pyridine or mixtures thereof.

Alternatively, compounds of general formula II can be prepared as illustrated in the general scheme 2:

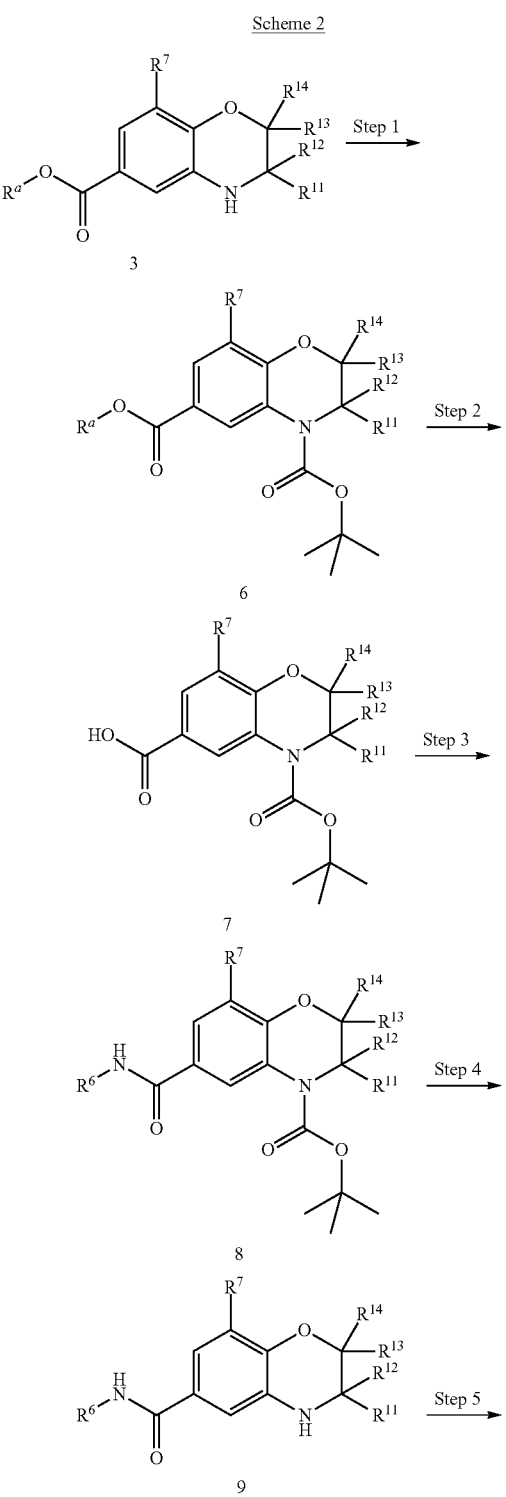

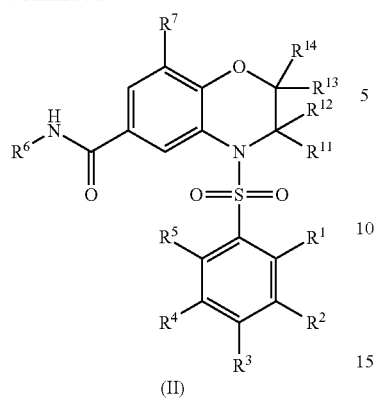

(II)

In step 1, scheme 2, the 3,4-dihydro-2H-benzo[1,4]oxazine-6-carboxylic acid alkyl ester 3 is converted into the corresponding tert-butylcarbamate of formula 6, using methods well known to someone skilled in the art, e.g. tert-butylcarbamate protection under basic conditions. The reaction is typically carried out in aprotic solvents such as acetone, acetonitrile, tetrahydrofuran, N,N-dimethylformamide, N-methylpyrrolidinone, dioxane and mixtures thereof at temperatures between 20° C. and 100° C. Typically used bases are sodium hydride, potassium hydride, sodium methoxide, potassium tert-butoxide, triethylamine, N,N-diisopropylethylamine, pyridine and potassium carbonate.

In step 2, scheme 2, the obtained compound of the formula 6 is converted into the corresponding carboxylic acid of the formula 7, in analogy with scheme 1, step 4.

In step 3, scheme 2, the carboxylic acid derivative of formula 7 is converted, with the appropriate amine $R^6$—$NH_2$, into the corresponding amide 8, in analogy with scheme 1, step 5.

In step 4, scheme 2, the tert-butylcarbamate group is removed to give a compound of formula 9, using methods well known to someone skilled in the art, e.g. acid mediated tert-butylcarbamate deprotection. This is typically carried out with or without solvents such as dichloromethane, dioxane and tetrahydrofuran and mixtures thereof at temperature between 0° C. and 60° C. Typically used acids are hydrogen chloride, concentrated hydrochloric acid and trifluoroacetic acid.

In step 5, scheme 2, the obtained compounds of general formula 9 are converted into their corresponding sulfonamides of general formula II, in analogy to scheme 1, step 3.

Intermediates of general formula 9 can also be prepared as illustrated in the general scheme 3:

Scheme 3

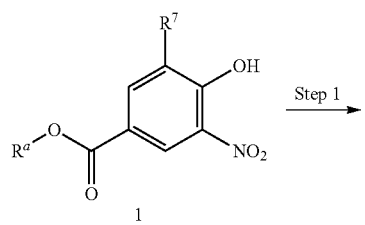

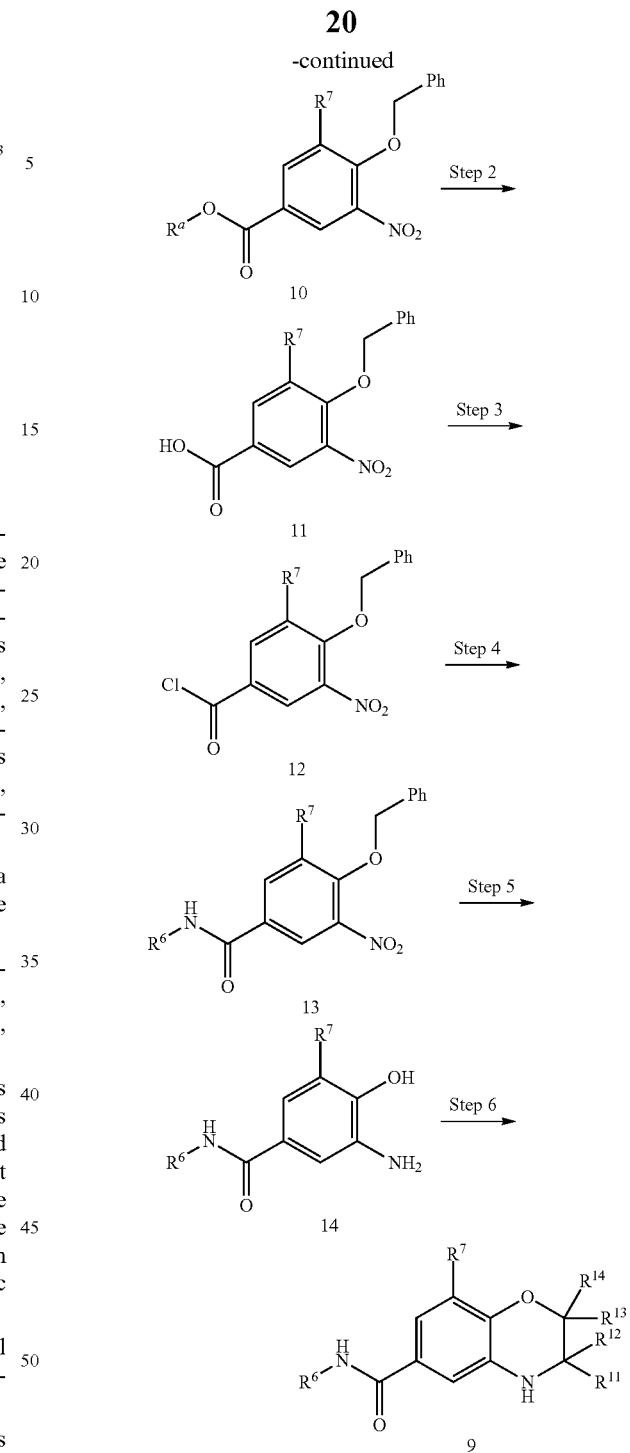

In step 1, scheme 3, nitrophenol of general formula 1 is protected with a benzylic group according to methods well known to somebody skilled in the art, i.e. phenol alkylation. The reaction is typically carried out in an aprotic solvent such as tetrahydrofuran, dimethylformamide, acetone at temperatures between −20° C. and 120° C. using benzyl bromide or benzyl chloride. Typically used bases are potassium tert-butoxide, potassium carbonate, sodium hydride and the like.

In step 2, scheme 3, ester 10 is converted to the corresponding carboxylic acid 11, in analogy with scheme 1, step 4.

In step 3, scheme 3, the obtained acid of general formula II is converted to the corresponding acyl chloride 12 using methods well known to someone skilled in the art. Typically employed reagents for the formation of the acyl chloride are thionyl chloride, phosphorous pentachloride, oxalyl chloride or cyanuric chloride, and the reaction is generally conducted in the absence of a solvent or in the presence of an aprotic solvent like dichloromethane, toluene, dimethylformamide, acetone or mixtures thereof. A base can optionally be added, like for example pyridine, triethylamine, diisopropylethylamine or N-methyl morpholine.

In step 4, scheme 3, acyl chloride 12 is coupled with an appropriate amine $R^6$—$NH_2$ to form the corresponding amide 13. The reaction is typically carried out in an aprotic solvent, like dichloromethane, tetrahydrofuran or acetone, in the presence of a base. Typical bases are triethylamine, 4-methylmorpholine, pyridine, diisopropylethylamine or dimethylaminopyridine or mixtures thereof.

In step 5, scheme 3, the benzyl group of the obtained compound 13 is cleaved and at the same time the nitro group is reduced to produce the corresponding aminophenol 14 using methods well known to someone skilled in the art, e.g. reductive debenzylation and nitro reduction. The reaction is typically carried out in a solvent like methanol, ethanol, dichloromethane, tetrahydrofuran, dimethylformamide, water or mixtures thereof at temperature between 20° C. and 60° C. under an atmosphere of hydrogen at pressure between 1 and 50 bar. Typically used catalysts are palladium, platinum, platinum oxide and the like.

In step 6, scheme 3, the obtained aminophenol of general formula 14 is converted to the corresponding 3,4-dihydro-2H-benzo[1,4]oxazine 9, in analogy with scheme 1, step 2.

Intermediates of general formula 4 can also be prepared as illustrated in the general scheme 4:

Scheme 4

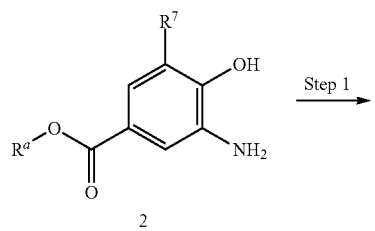

2

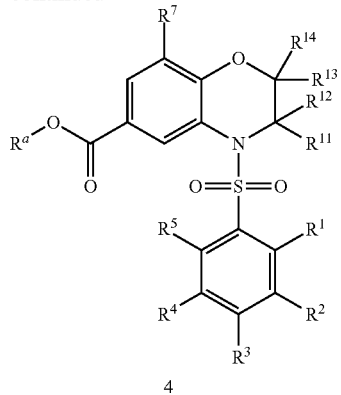

4

In step 1, scheme 4, 3-amino-4-hydroxybenzoate 2 is converted to the sulfonamide of general formula 15, in analogy with scheme 1, step 3.

In step 2, scheme 4, compound 15 is cyclized with an appropriately substituted 1,2-dibromoethane reagent to produce 4, in analogy with scheme 1, step 2.

Compounds of formula I wherein V is C—$R^7$, W is a single bond, X is O and Y=—C($R^{11}$)=C($R^{12}$)— are part of the present invention and can be represented by formula III:

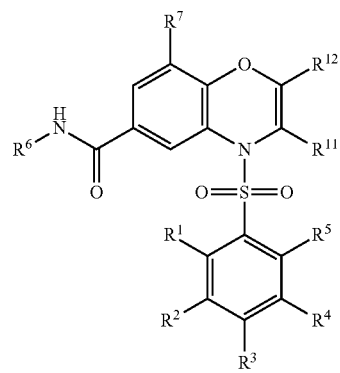

(III)

Compounds of general formula III can be accessed according to the following general scheme 5:

Scheme 5

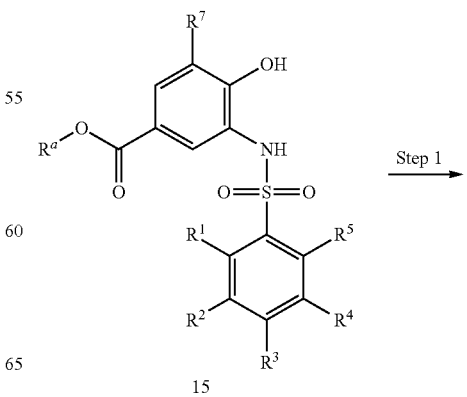

15

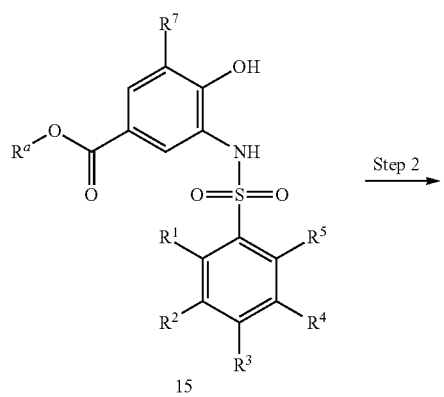

15

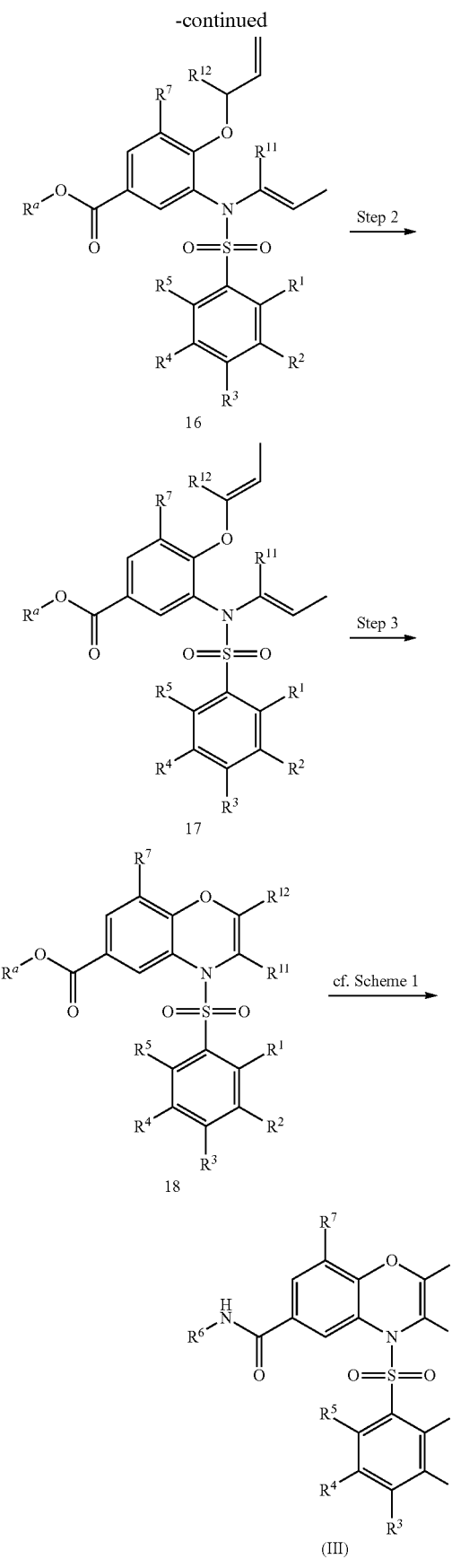

In step 1, scheme 5, compound 15 is transformed into diallyl derivative 16, using methods well known to somebody skilled in the art. For instance, the reaction is performed with an allyl halide derivative, in a solvent such as acetone, acetonitrile, or N,N-dimethylformamide, in the presence of a base, e.g., sodium carbonate, potassium carbonate, or sodium hydride, at temperatures between 20° C. and 100° C. Alternatively, 16 is prepared from 15 under Mitsunobu conditions using an allyl alcohol derivative, a phosphine, e.g., triphenylphosphine, an azodicarboxylate, e.g., diethyl azodicarboxylate or diisopropyl azodicarboxylate, in a solvent such as dichloromethane, toluene or tetrahydrofuran and at temperatures between 0° C. and 40° C.

In step 2, scheme 5, the bis-allyl compound 16 is converted into 17 in the presence a suitable alkene isomerization catalyst e.g., carbonylchlorohydrotris(triphenylphosphine)ruthenium. The reaction is carried out in an inert solvent such as toluene or xylene, at temperatures between 20° C. and the boiling point of the solvent.

In step 3, scheme 5, compound 17 is transformed into benzo[1,4]oxazine derivative 18 by a ring-closing metathesis reaction, in the presence of a suitable catalysts. Several catalysts capable of promoting this reaction are known in the literature, e.g., benzylidenedichlorobis(tricyclohexylphosphine)ruthenium; or dichloro(1,3-dimesityl-4,5-dihydroimidazol-2-ylidene)(phenylmethylene)(tricyclohexylphosphine)ruthenium. The reaction is carried out in an inert solvent such as toluene or dichloromethane, at temperatures between 20° C. and the boiling point of the solvent.

The preparation of the benzo[1,4]oxazines of general formula III from intermediate 18 follows the same synthetic route as that described in the preparation of 3,4-dihydro-2H-benzo[1,4]oxazines of general formula II from the intermediate 4 (scheme 1, steps 4 and 5).

Compounds of formula I wherein V is C—$R^7$, W is a single bond, X is O and Y=—C($R^{11}R^{12}$)C($R^{13}R^{14}$)C($R^{15}R^{16}$) are part of the present invention and can be represented by formula IV:

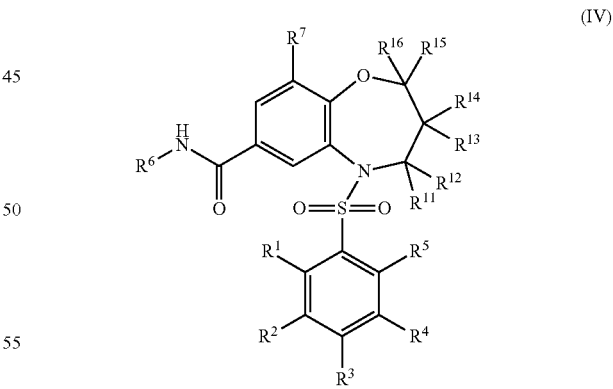

(IV)

Compounds of general formula IV can be prepared in analogy to compounds of general formula II (schemes 1-4), but by replacing the 1,2-dibromoethane derivative in the cyclisation step with an appropriately substituted 1,3-dibromopropane derivative.

Compounds of formula I wherein V is C—$R^7$, W is a single bond, X is O and Y=—C($R^{11}R^{12}$)C($R^{13}R^{14}$)C($R^{15}R^{16}$)C($R^{17}R^{18}$)— are part of the present invention and can be represented by formula V:

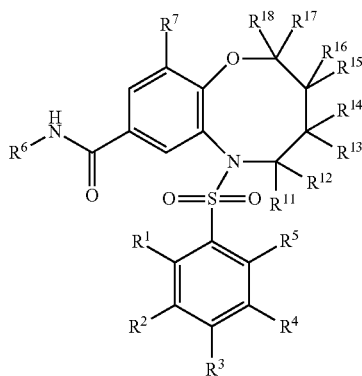

(V)

Compounds of general formula V can be produced in analogy to compounds of general formula II (schemes 1-4), but by replacing the 1,2-dibromoethane derivative in the cyclisation step with an appropriately substituted 1,4-dibromobutane derivative.

Compounds of formula I wherein V is C—$R^7$, W is a single bond, X is O and Y=—C($R^{11}R^{12}$)— are part of the present invention and can be represented by formula VI:

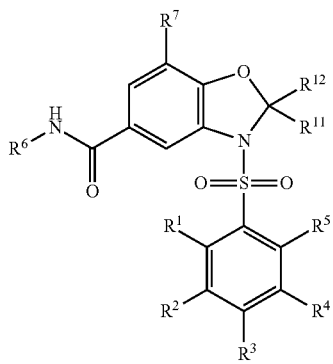

(VI)

Compounds of general formula VI can be synthesized according to scheme 6:

Scheme 6

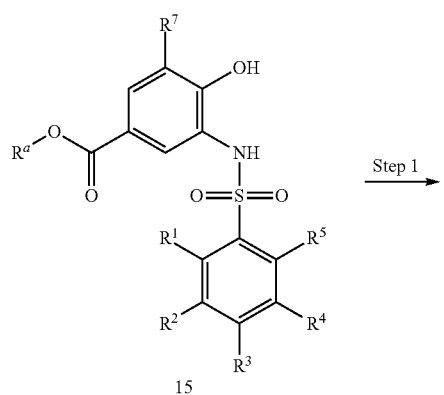

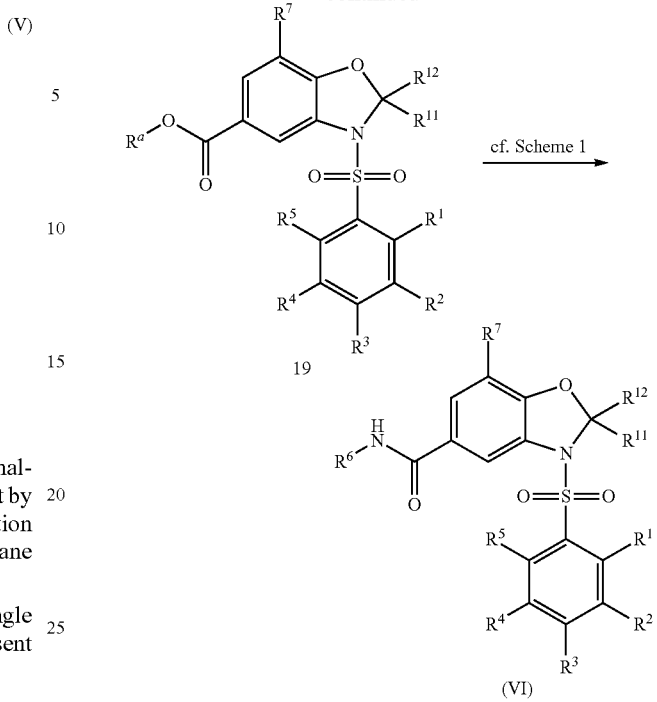

In step 1, scheme 6, N-(2-hydroxy-phenyl)-benzenesulfonamide derivative 15 is converted to N-phenylsulfonyl-2,3-dihydro-benzoxazole 19 according to methods well known to somebody skilled in the art, e.g., double nucleophilic substitution or acetalization. For instance, 15 is reacted with dibromomethane in the presence of a base, e.g., sodium carbonate, potassium carbonate, or sodium hydride, in a solvent such as acetonitrile or N,N-dimethylformamide at temperatures between 60° C. and 100° C. Alternatively, and especially preferred in the case where $R^{11}$ and/or $R^{12} \neq H$, 15 is reacted with an suitable free or masked carbonyl derivative such as aldehyde, ketone or acetal, in the presence of a catalyst, e.g., toluene-4-sulfonic acid, titanium(IV)chloride or zinc chloride, optionally in the presence of a solvent, such as toluene or dichloromethane, at temperatures between 0° C. and 150° C.

The preparation of the 2,3-dihydro-benzoxazoles of general formula VI from intermediate 19 follows the same synthetic route as that described in the preparation of 3,4-dihydro-2H-benzo[1,4]oxazines of general formula II from the intermediate 4 (scheme 1, steps 4 and 5).

Compounds of formula I wherein W is a single bond, X'=NH, N-alkyl, or N-cycloalkyl, or S, and Y=—$CH_2C(R^{13}R^{14})$—, are part of the present invention and can be represented by formula VII:

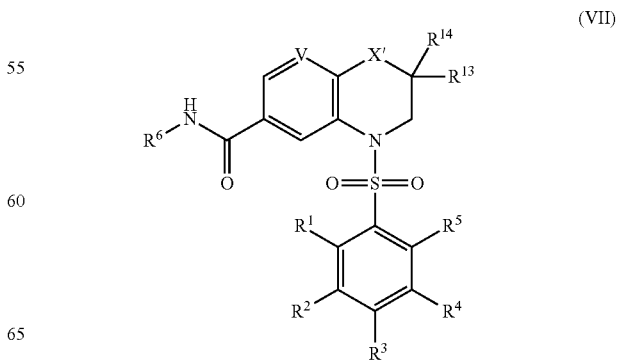

(VII)

Compounds of general formula VII can be accessed according to the general scheme 7:

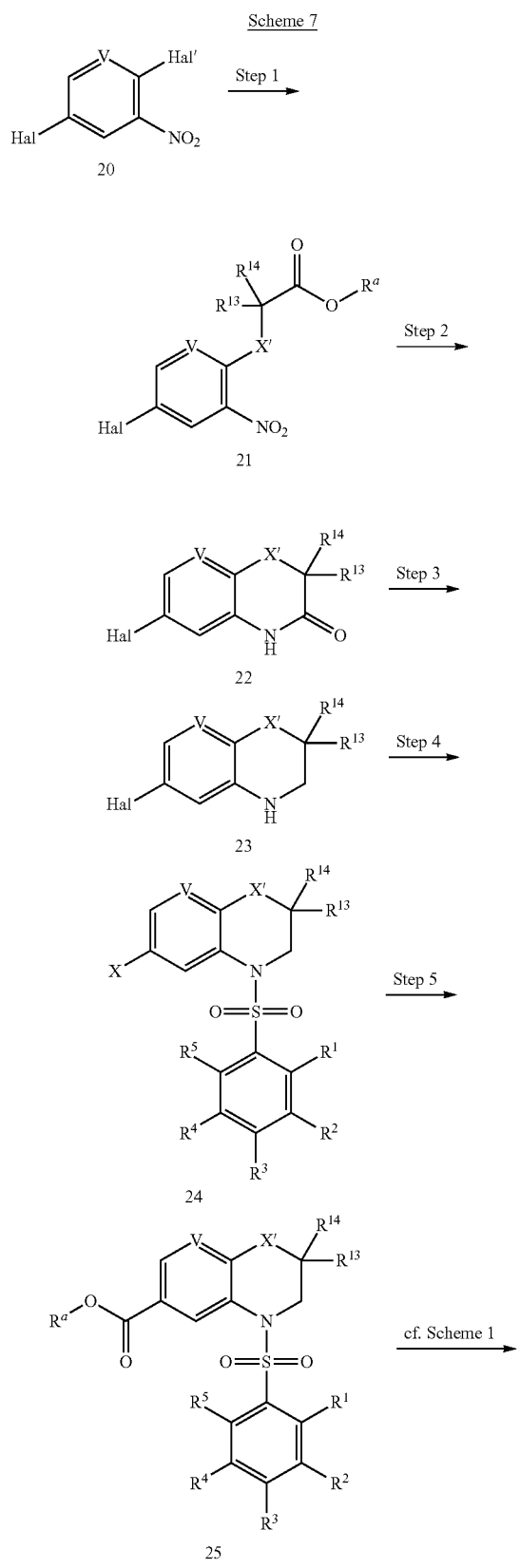

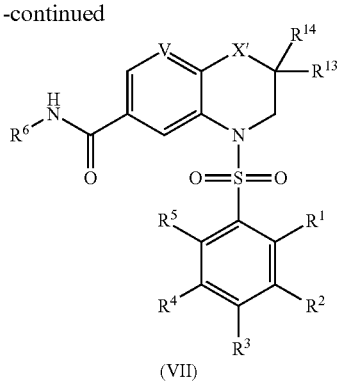

In step 1, scheme 7, 1-nitro-2,5-halo-arene 20 (Hal=Br, I; Hal'=F, Cl, Br, I) is transformed into compound 21, using methods well known in the art. The reaction is performed with an appropriate reagent (H—X'—C($R^{13}R^{14}$)C(O)—O—$R^a$, with $R^a$=methyl or ethyl), optionally in the presence of a base, e.g., sodium hydride, sodium hydroxide, potassium hydroxide, potassium carbonate, sodium carbonate, sodium hydrogencarbonate, in a solvent such as tetrahydrofuran, 1,4-dioxane, N,N-dimethylformamide, or dimethyl sulfoxide, at a temperature between 20° C. and 200° C., optionally under microwave irradiation.

In step 2, scheme 7, compound 21 is elaborated into lactam 22 through methods known in the art, i.e., reduction of the nitro group and simultaneous cyclisation. The reaction is performed using a reducing metal such as iron or tin, in a suitable solvent, e.g., methanol, ethanol, acetic acid, or water, optionally in the presence of an acid, e.g., hydrochloric acid or sulfuric acid, at temperatures between 20° C. and the boiling point of the solvent.

In step 3, scheme 7, the amide group of 22 is reduced to produce the corresponding amine 23. This reaction is accomplished using a suitable reagent, e.g., borane-tetrahydrofuran complex, borane-dimethylsulfide complex, diisobutylaluminum hydride, or lithium aluminum hydride, in a solvent such as tetrahydrofuran, at temperatures between 0° C. and 50° C.

In step 4, scheme 7, amine 23 is converted to the sulfonamide of general formula 24, in analogy with scheme 1, step 3.

In step 5, scheme 7, halide 24 is converted to the carboxylic acid alkyl ester 25 using methods well known to somebody skilled in the art, i.e. palladium-catalyzed alkoxycarbonylation. The reaction is typically carried out in an alcoholic solvent such as methanol or ethanol, or in a mixture of an alcoholic solvent with an aprotic solvent, like toluene or ethyl acetate, at temperatures between 25° C. and 150° C. under an atmosphere of carbon monoxide at pressures between 1 bar and 100 bar, and in the presence of a base, e.g., triethylamine or 4-methylmorpholine. Typically used palladium catalysts are palladium dichloride, palladium tetrakis(triphenylphosphine) or dichloro[1,1'-bis(diphenylphosphino)ferrocene] palladium.

The preparation of the compounds of general formula VII from intermediate 25 follows the same synthetic route as that described in the preparation of 3,4-dihydro-2H-benzo[1,4] oxazines of general formula II from the intermediate 4 (scheme 1, steps 4 and 5).

Intermediates of general formula 25 can be also prepared starting from compounds of general formula 26 ($R^a$=methyl or ethyl), according to scheme 8:

Scheme 8

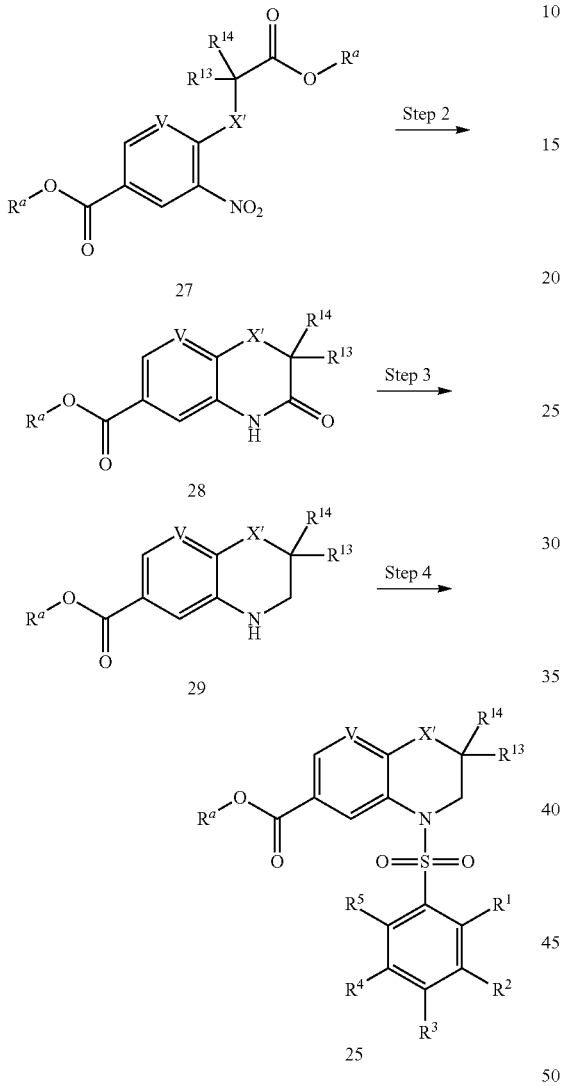

In step 1, scheme 8, 26 is reacted at the hydroxy, amino or thiol group to afford 27, applying methods well known in the art, e.g., Williamson alkylation. The reaction is performed with an appropriate reagent (Hal-C($R^{13}R^{14}$)—C(O)—O—$R^a$, with $R^a$=methyl or ethyl, and Hal=Cl, Br or I), in the presence of a base, e.g., sodium hydride, sodium hydroxide, potassium hydroxide, potassium carbonate, sodium carbonate, sodium hydrogencarbonate, in a solvent such as tetrahydrofuran, 1,4-dioxane, N,N-dimethylformamide, or dimethyl sulfoxide, at a temperature between 20° C. and 150° C.

In step 2, scheme 8, compound 27 is elaborated into lactam 28, in analogy to scheme 7, step 2.

In step 3, scheme 8, the amide group of 28 is reduced to the amine, using a suitable reagent, e.g., borane-tetrahydrofuran complex or borane-dimethylsulfide complex. The reaction is performed in a solvent such as tetrahydrofuran, at temperatures of 0-60° C.

In step 4, scheme 8, amine 29 is converted to sulfonamide 25 in analogy to scheme 7, step 4.

Compounds of formula I wherein V is N, W is a single bond, and X is O are part of the present invention and can be represented by formula VIII:

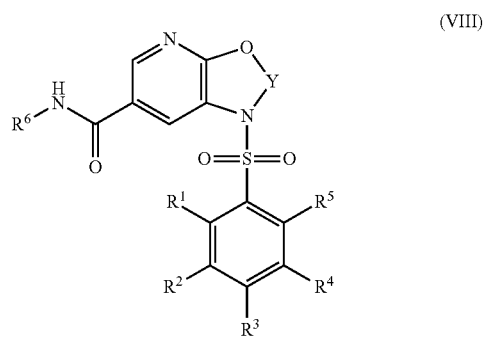

(VIII)

Scheme 9

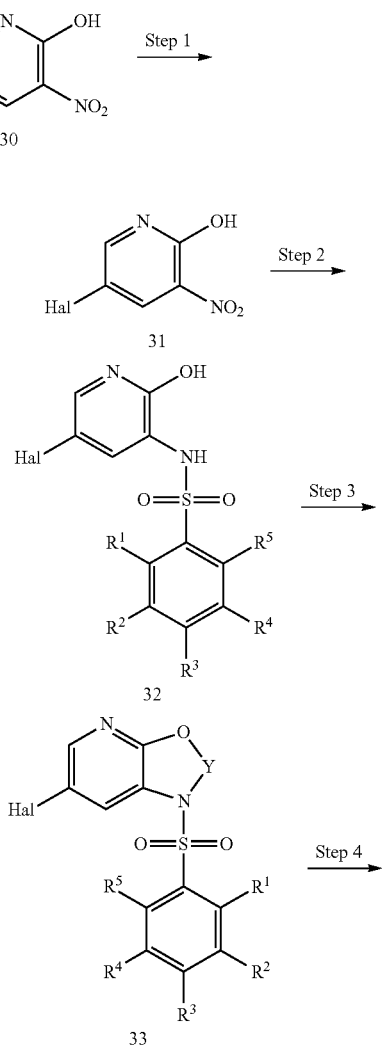

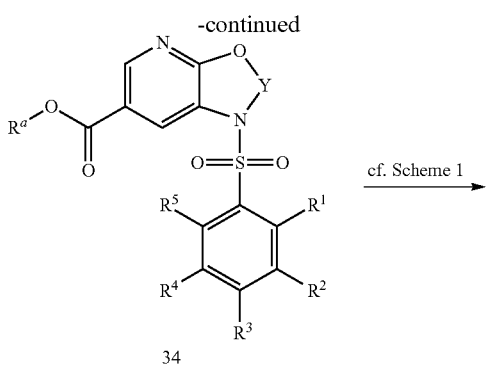

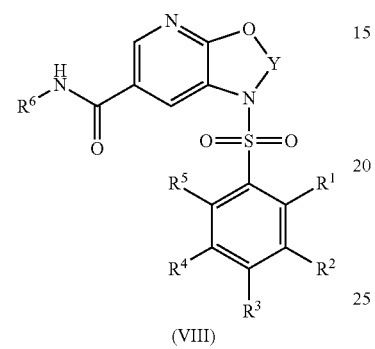

In step 1, scheme 9, the nitro group of 5-halo-2-hydroxy-3-nitropyridine 30 (Hal=Br, I) is reduced to the amino group, using methods well known to somebody skilled in the art. The reaction is typically carried out using reducing metals like iron or tin, in a solvent such as methanol, ethanol, acetic acid, water, or mixtures thereof, optionally in the presence of an acid such as ammonium chloride, hydrochloric acid, or sulfuric acid, at temperatures of 20-100° C.

In step 2, scheme 9, aminopyridine 31 is converted to sulfonamide 32, in analogy to scheme 1, step 3.

In step 3, scheme 9, 32 is transformed into 33 by an appropriate method, e.g., double nucleophilic substitution, with an appropriately substituted α,ω-dibromoalkane or α,ω-bis-(alkyl/aryl-sulfonyloxy)alkane derivative. The reaction is typically carried out in an aprotic solvent like dimethylformamide, acetone, or tetrahydrofuran in the presence of a base like for example sodium hydride or potassium carbonate, at temperatures between 20° C. and 100° C. Alternatively, and especially preferred in the case where Y=C($R^{11}R^{12}$), with $R^{11}$ and/or $R^{12}$≠H, 32 is reacted with a suitable free or masked carbonyl derivative such as aldehyde, ketone or acetal, in the presence of a catalyst, e.g., toluene-4-sulfonic acid, titanium (IV) chloride or zinc chloride, optionally in the presence of a solvent, such as toluene or dichloromethane, at temperatures between 0° C. and 150° C.

Alternatively, steps 2 and 3 can be performed in reverse order.

In step 4, scheme 9, halide 33 is converted into ester 34, in analogy to scheme 7, step 5.

The preparation of the compounds of general formula VIII from intermediate 34 follows the same synthetic route as that described in the preparation of 3,4-dihydro-2H-benzo[1,4] oxazines of general formula II from the intermediate 4 (scheme 1, steps 4 and 5).

Alternatively, compounds of general formula VIII can be obtained directly from halide 33 through palladium-catalyzed aminocarbonylation, using reagents and conditions described in the art. The reaction requires an appropriately substituted amine, $R^6$—$NH_2$, and is typically performed in an aprotic solvent such as N,N-dimethylformamide, N,N-dimethylacetamide or tetrahydrofuran, at temperatures between 60° C. and 200° C. under an atmosphere of carbon monoxide at pressures between 1 bar and 100 bar, or in the presence of a reagent capable of liberating carbon monoxide such as molybdenum hexacarbonyl, and in the presence of a base, e.g., triethylamine, 4-methylmorpholine, or 1,8-diazabicyclo [5.4.0]undec-7-ene. Typically used palladium catalysts are palladium dichloride, palladium tetrakis(triphenylphosphine), dichloro[1,1'-bis(diphenylphosphino)ferrocene]palladium, or trans-bis(μ-acetato)bis[o-(di-o-tolylphosphino) benzyl]dipalladium(II). Optionally, additional phosphine ligands such as triphenylphosphine, tris(tert-butyl)phosphine tetrafluoroborate, or 2,2'-bis(diphenylphosphino)-1,1'-binaphthyl are used.

Compounds of formula I wherein W=—C($R^8R^9$)— and X is O are part of the present invention and can be represented by formula IX:

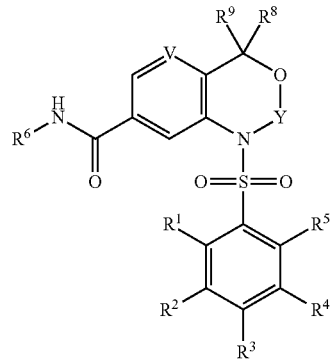

Compounds of general formula IX can be accessed according to scheme 10:

Scheme 10

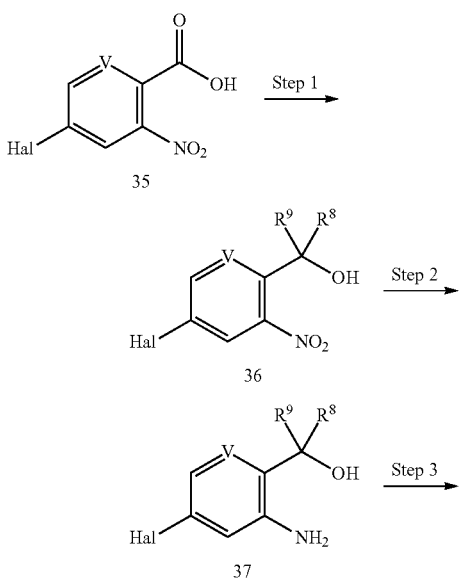

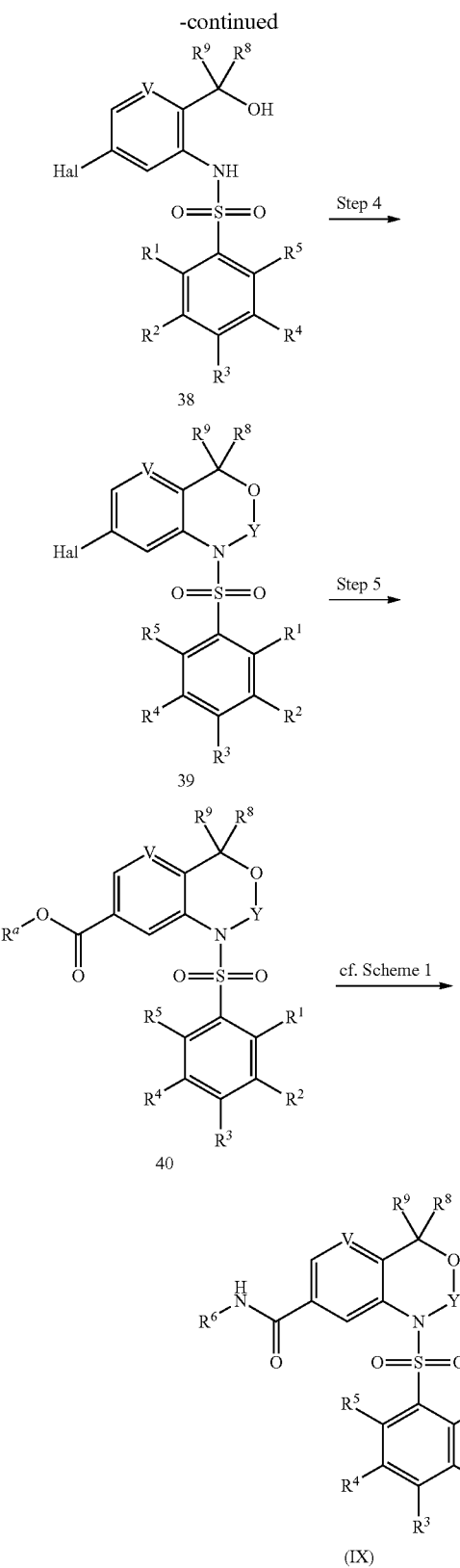

reaction is performed using a suitable reducing agent, e.g., borane-tetrahydrofuran, in a solvent such as tetrahydrofuran, at temperatures between 0° C. and 50° C. In step 2, scheme 10, the 2-nitrobenzylalcohol is reduced to the aniline 37 by a suitable reducing agent, e.g., iron, tin, or tin chloride, in a solvent such as methanol, ethanol, acetic acid, water, or mixtures thereof, optionally in the presence of an acid such as ammonium chloride, hydrochloric acid, or sulfuric acid, at temperatures of 20-100° C.

In the case where $R^8$ and $R^9$=alkyl, the acid 35 is converted into the corresponding alkyl ester through acid-promoted esterification, using the alcohol as solvent, at temperatures between 25° C. and the boiling point of the alcohol, in the presence of a mineral acid such as hydrochloric acid or sulfuric acid. The alkyl ester thus obtained is then reduced at the nitro group as described above, leading to an alkyl 2-aminobenzoate, which is treated with a suitable organometallic reagent such as organomagnesium or organolithium compound to produce 37.

In the case where $R^8 \ne R^9$, the acid 35 is converted into the corresponding N-methoxy-N-methylamide, using reagents methods known in the art. For instance, the acid 35 is activated using a suitable reagent, e.g., methanesulfonyl chloride, thionyl chloride, isobutyl chloroformate, and a base, e.g., triethylamine or 4-methylmorpholine, then the acid chloride or mixed anhydride intermediate obtained is reacted with N,O,dimethylhydroxylamine, in a solvent such as tetrahydrofuran or dichloromethane, at temperatures between −10° C. and 40° C. In the next step, the nitro group is reduced as described above. The obtained 2-amino-N-methoxy-N-methylbenzamide intermediate is then reacted with the appropriate organomagnesium ($R^8$—Mg-Hal, with Hal=Cl, Br, I) or organolithium ($R^8$—Li) reagent, to give an alkyl aryl ketone. This ketone intermediate is transformed into the benzyl alcohol 37 using a suitable organomagnesium ($R^9$—Mg-Hal, with Hal=Cl, Br, I), organolithiumium ($R^9$—Li) reagent, or with a hydride reagent such as sodium borohydride (in the case where $R^9$=H).

In step 3, scheme 10, amine 37 is converted to the sulfonamide of general formula 38, in analogy to scheme 1, step 3.

In step 4, scheme 10, the 2-(sulfonylamino)benzylalcohol 38 is transformed into 39 by an appropriate method, e.g., double nucleophilic substitution, with an appropriately substituted α,ω-dibromoalkane derivative. The reaction is typically carried out in an aprotic solvent like dimethylformamide, tetrahydrofuran in the presence of a base like for example sodium hydride or potassium tert-butoxide, at temperatures between 20° C. and 100° C. Alternatively, and especially preferred in the case where Y=C($R^{11}R^{12}$), 38 is reacted with a suitable free or masked carbonyl derivative such as aldehyde, ketone or acetal, in the presence of a catalyst, e.g., toluene-4-sulfonic acid, titanium(IV) chloride or zinc chloride, optionally in the presence of a solvent, such as toluene or dichloromethane, at temperatures between 0° C. and 150° C.

In step 5, scheme 10, halide 39 is converted into ester 40, in analogy to scheme 7, step 5.

The preparation of the compounds of general formula IX from intermediate 40 follows the same synthetic route as that described in the preparation of 3,4-dihydro-2H-benzo[1,4]oxazines of general formula II from the intermediate 4 (scheme 1, steps 4 and 5).

In step 1, scheme 10, 4-halo-2-nitroarene-carboxylic acid 35 (Hal=Br, I) is converted to benzyl alcohol 36, using methods well known in the art. In the case where $R^8$=$R^9$=H, the Alternatively, intermediates of general formula 40 can be prepared as illustrated in the general scheme 11:

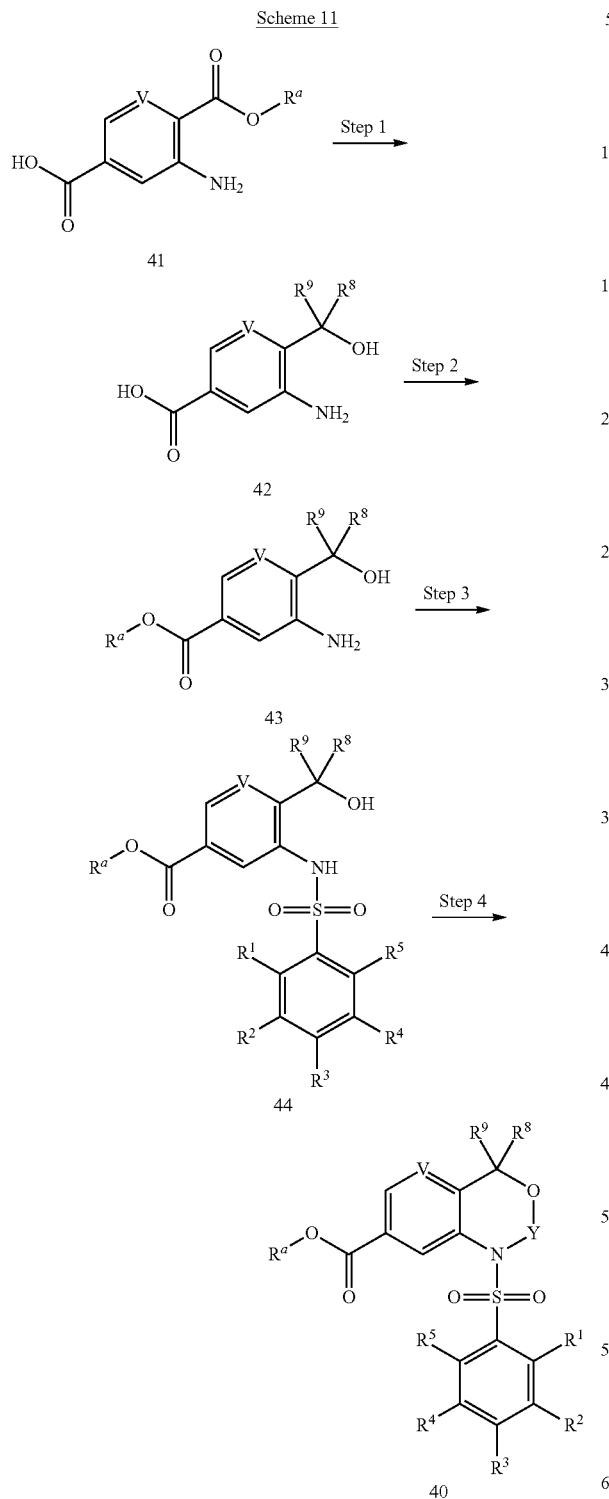

In step 1, scheme 11, 4-(alkoxycarbonyl)-3-amino-arene-carboxylic acid 41 ($R^a$=lower alkyl, e.g., methyl or ethyl) is reacted at the ester functional group with an appropriate reagent, leading to benzyl alcohol derivative 42. In the case where $R^8$ and $R^9$=H, this conversion is accomplished with a borohydride reagent, e.g., lithium borohydride, in a solvent such as tetrahydrofuran. In the case where $R^8$ and $R^9$=alkyl, 41 is reacted with two equivalents of a suitable organolithium or organomagnesium reagent, in a solvent such as diethyl ether or tetrahydrofuran.

In step 2, scheme 11, carboxylic acid 42 is converted into the corresponding alkyl ester ($R^a$=lower alkyl) using methods known in the art, e.g., alkylation. This reaction is carried out using suitable reagents, e.g., alkyl halides or sulfonic acid alkyl esters, and a base such as potassium hydrogencarbonate or potassium carbonate, in a solvent such as N,N-dimethylformamide, acetone, or acetonitrile, at temperatures between 0° C. and 80° C.

In step 3, scheme 11, amine 43 is converted to the sulfonamide of general formula 44, in analogy to scheme 1, step 3.

In step 4, scheme 11, compound 44 is cyclized with appropriate reagents, in analogy to scheme 10, step 5, leading to compound of general formula 40.

Compounds of formula I wherein W is a single bond, and X is $NR^{10}$ are part of the present invention and can be represented by formula X:

Compounds of general formula X can be accessed according to the general scheme 12:

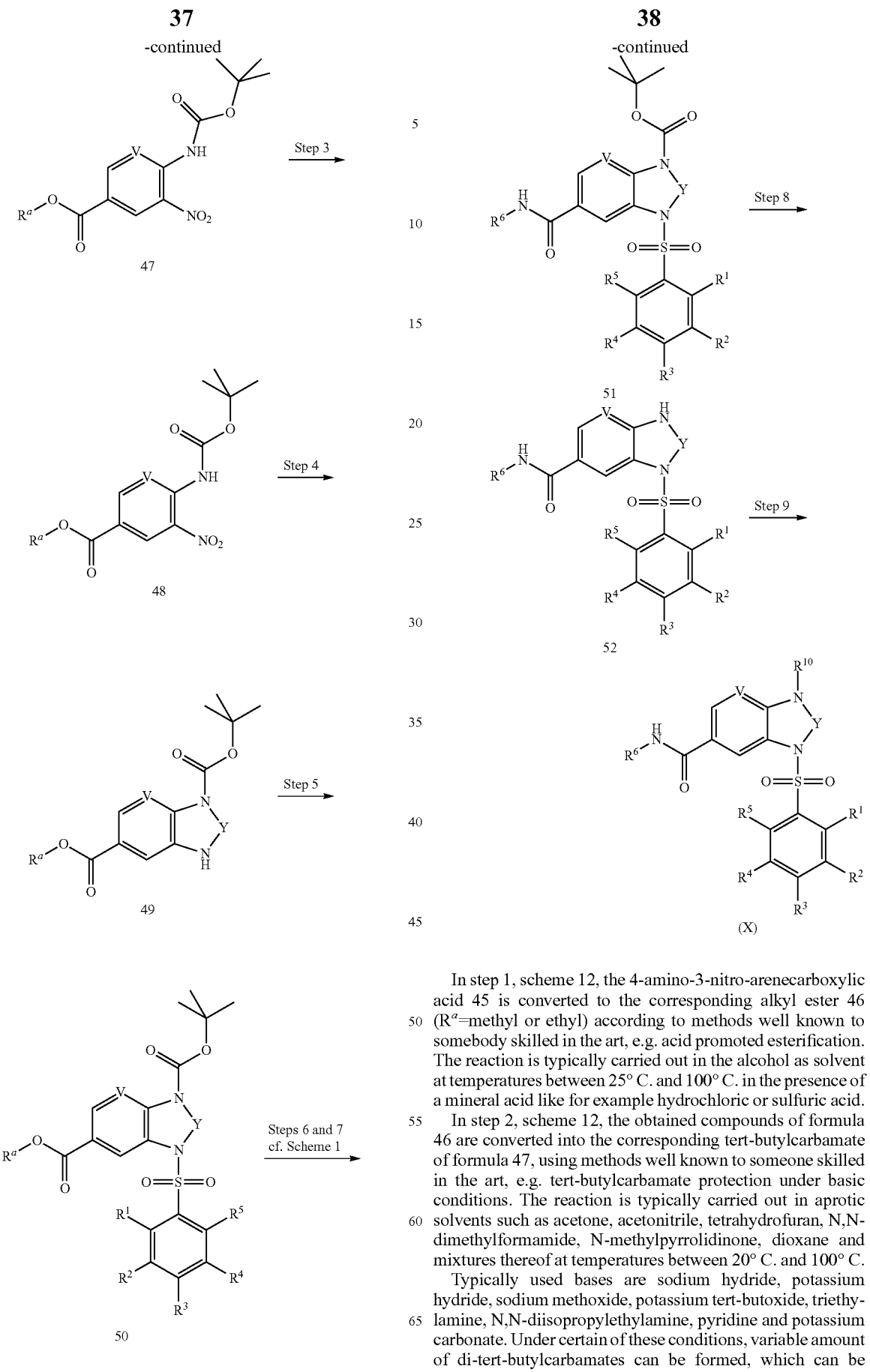

In step 1, scheme 12, the 4-amino-3-nitro-arenecarboxylic acid 45 is converted to the corresponding alkyl ester 46 ($R^a$=methyl or ethyl) according to methods well known to somebody skilled in the art, e.g. acid promoted esterification. The reaction is typically carried out in the alcohol as solvent at temperatures between 25° C. and 100° C. in the presence of a mineral acid like for example hydrochloric or sulfuric acid.

In step 2, scheme 12, the obtained compounds of formula 46 are converted into the corresponding tert-butylcarbamate of formula 47, using methods well known to someone skilled in the art, e.g. tert-butylcarbamate protection under basic conditions. The reaction is typically carried out in aprotic solvents such as acetone, acetonitrile, tetrahydrofuran, N,N-dimethylformamide, N-methylpyrrolidinone, dioxane and mixtures thereof at temperatures between 20° C. and 100° C.

Typically used bases are sodium hydride, potassium hydride, sodium methoxide, potassium tert-butoxide, triethylamine, N,N-diisopropylethylamine, pyridine and potassium carbonate. Under certain of these conditions, variable amount of di-tert-butylcarbamates can be formed, which can be reconverted to the mono-tert-butylcarbamates using methods well known to somebody skilled in the art, e.g. acid promoted tert-butylcarbamate deprotection. The reaction is typically carried out with or without solvents such as dichloromethane, dioxane and tetrahydrofuran and mixtures thereof at temperature between −20° C. and 20° C. Typically used acids are hydrogen chloride, concentrated hydrochloric acid and trifluoroacetic acid.

In step 3, scheme 12, the obtained compounds of general formula 47 are converted to the corresponding amines 48 using methods well known to those skilled in the art, e.g. nitro reduction. The reaction is typically carried out in solvents such as ethanol, methanol or water under an atmosphere of hydrogen at a pressure of 1 to 50 bar and temperatures between 0° C. and 100° C. with catalysts such as palladium, platinum or platinum oxide. Alternatively, the reaction can be carried out using reducing metals like for example tin or tin chloride in the presence of concentrated mineral acids like hydrochloric or sulfuric acid, or with Ni/Raney.

In step 4, scheme 12, the obtained amine of formula 48 is cyclized to compound 49, in analogy to scheme 9, step 3.

In step 5, scheme 12, amine 49 is converted into the sulfonamide derivative 50, in analogy to scheme 1, step 3.

The preparation of the amides of general formula 51 from esters of formula 50 follows the same synthetic route as that described in the preparation of 3,4-dihydro-2H-benzo[1,4]oxazines of general formula II from the intermediate 4 (scheme 1, steps 4 and 5).

In step 8, scheme 12, the tert-butylcarbamate group is removed to give the compounds of formula 52, using methods well known to someone skilled in the art, e.g. acid mediated tert-butylcarbamate deprotection. This is typically carried out with or without solvents such as dichloromethane, dioxane and tetrahydrofuran and mixtures thereof at temperature between 0° C. and 60° C. Typically used acids are hydrogen chloride, concentrated hydrochloric acid and trifluoroacetic acid.

In step 9, scheme 12, the free amine group of compounds of the general formula 52 can be functionalized to give the compounds of general formula X in a variety of ways well known to somebody skilled in the art, e.g. alkylation, acylation, reductive alkylation, sulfonylation, formation of carbamates and formation of ureas.

Compounds of general formula I wherein W is a bond X is $SO_2$, and Y=—$CH_2C(R^{13}R^{14})$— are part of the present invention and are represented by the general formula XI.

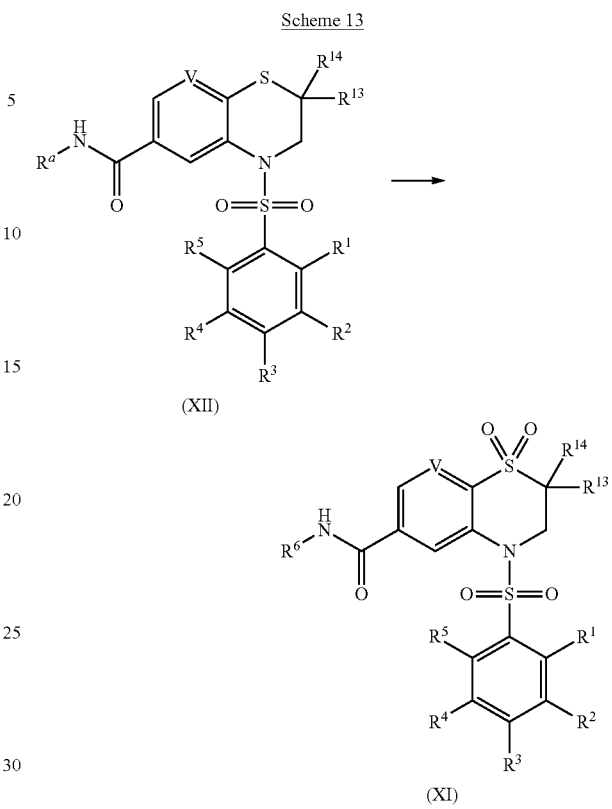

Scheme 13

Sulfides XII, which are prepared as illustrated in schemes 7 and 8, can be converted to sulfones of general formula XI through reaction with an appropriate oxidizing agent. For instance, XII is treated with at least two equivalents of a peroxide or peracid such as hydrogen peroxide or 3-chloroperbenzoic acid, in a solvent such as dichloromethane, water, formic acid or mixtures thereof, at temperatures between 0° C. and 25° C., preferably 0° C. This conversion may also be accomplished on any synthetic precursor of XII containing the alkyl-aryl-sulfide moiety.

Compounds of general formula I wherein W is a bond, X is SO, and Y=—$CH_2C(R^{13}R^{14})$— are part of the present invention and are represented by the general formula XIII.

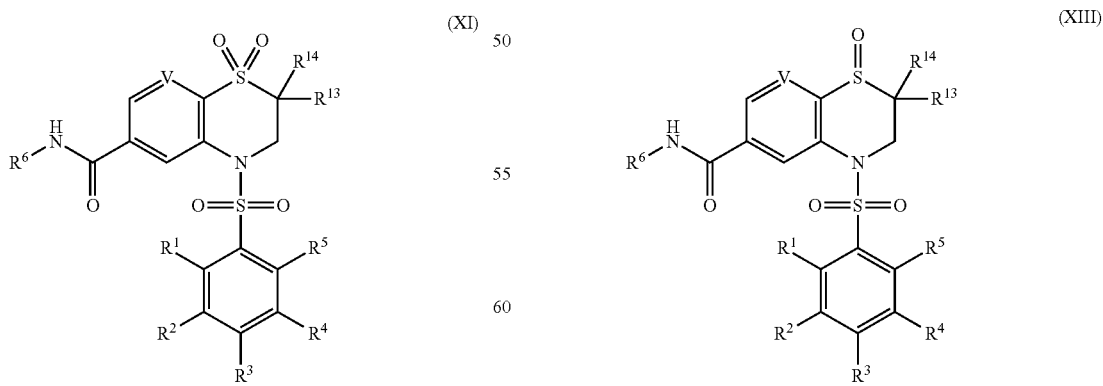

Compounds of general formula XI can be prepared for example starting from sulfides of general formula XII, as illustrated in scheme 13.

Compounds of general formula XIII can be prepared for example starting from sulfides of general formula XII, as illustrated in scheme 14.

Scheme 14

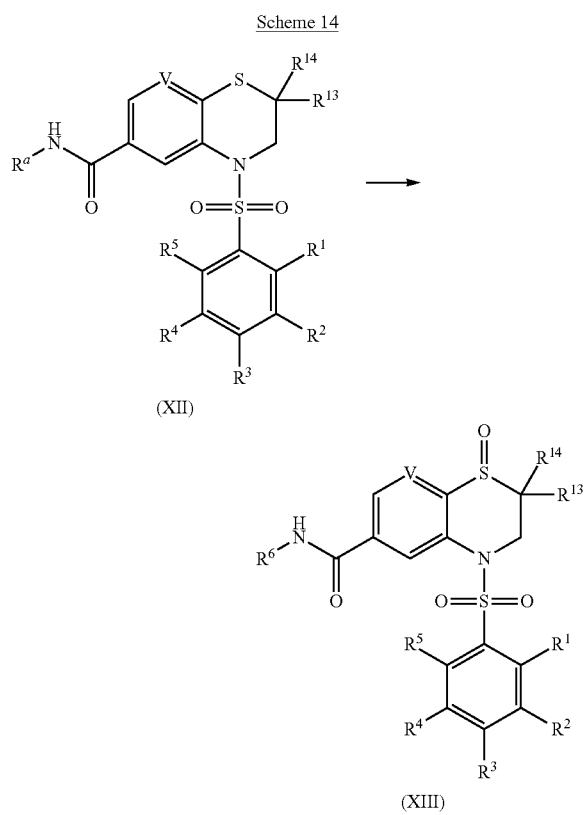

(XII)

(XIII)

Sulfides XII can be converted to sulfoxides of general formula XIII through reaction with an appropriate oxidizing agent. For instance, XII is treated with one equivalent of a peroxide or peracid such as hydrogen peroxide or 3-chloroperbenzoic acid, in a solvent such as dichloromethane, water, formic acid or mixtures thereof, at temperatures between 0° C. and 25° C., preferably 0° C. This conversion may also be accomplished on any synthetic precursor of XII containing the alkyl-aryl-sulfide moiety.

Compounds which carry a COOH group, e.g. as a substituent on $R^6$, can be prepared from the corresponding esters, e.g. the lower-alkyl esters (e.g. the methyl, ethyl, propyl or tert-butyl esters). Such esters are obtained as described in schemes 1-14 by employing an appropriate (alkoxycarbonylmethyl)-arylamine in the amide formation step. Alternatively, the esters are obtained as described in schemes 1-14 by employing an appropriate 4-bromoaniline or 4-iodoaniline derivative in the amide formation step and subjecting the N-4-halophenylamide derivative to a palladium-catalyzed alkoxycarbonylation, in analogy with scheme 7, step 5.

The esters are converted into their corresponding carboxylic acids using methods well known to someone skilled in the art, e.g. base or acid-mediated ester hydrolysis.

Base-mediated ester hydrolysis (preferred for methyl, ethyl, propyl esters) is typically carried out in solvents such as water, methanol, tetrahydrofuran and mixtures thereof at temperatures between −20° C. and 120° C. Typical reagents are aqueous or anhydrous lithium hydroxide, lithium hydroxide monohydrate, sodium hydroxide, potassium hydroxide, sodium hydrogen carbonate, sodium carbonate, potassium hydrogen carbonate and potassium carbonate.

Acid-mediated ester hydrolysis (preferred for tert-butyl esters) is typically carried out in liquids such as formic acid, aqueous or non-aqueous hydrogen chloride solutions, or trifluoroacetic acid at temperatures between 0° C. and 100° C. Optionally, co-solvents such as dichloromethane, 1,4-dioxane or water are used.

Compounds which carry an acid isostere such as 1H-tetrazol-5-yl, e.g. as a substituent on $R^6$, can be obtained from the corresponding nitriles which are converted to the corresponding 1H-tetrazoles using methods well known to somebody skilled in the art, e.g. dipolar cycloaddition with azides. The reaction is typically carried out in an aprotic solvent like dimethylformamide, dimethyl sulfoxide, tetrahydrofuran at temperatures between 25° C. and 200° C. using an azide source like ammonium azide, sodium azide or trialkyltin azide. The nitriles can be obtained as described in schemes 1-14 by employing an appropriate amino-cyano-arene in the amide formation step.

Compounds which carry an acid isostere such as 5-oxo-4H-[1,2,4]oxadiazol-3-yl, e.g. as a substituent on $R^6$, can be obtained as follows. In a first step, the corresponding benzonitriles are converted to N-hydroxy-benzamidines using methods well known to somebody skilled in the art, e.g. nucleophilic addition with hydroxylamine. The reaction is typically carried out in an aprotic solvent like dimethylformamide, dimethyl sulfoxide, tetrahydrofuran, acetonitrile, at temperatures between 0° C. and 150° C. in the presence of a base like triethylamine, diisopropylethylamine, 4-methylmorpholine or pyridine. In a second step, the obtained N-hydroxybenzamidines can be converted to the desired compounds using methods well known to somebody skilled in the art, e.g. intramolecular carbamate formation. The reaction is typically carried out in an aprotic solvent like benzene, toluene, xylene, dimethylformamide, dimethyl sulfoxide or mixtures thereof at temperatures between 0° C. and 200° C. in the presence of a base. Typical reagents for the formation of the carbamates are phosgene, triphosgene, carbonyldiimidazole, chloroformic acid alkyl esters, and the like. Typical bases are triethylamine, diisopropylethylamine, 4-methylmorpholine or pyridine.

Compounds which carry an acid isostere such as 2-oxo-3H-[1,2,3,5]oxathiadiazol-4-yl, e.g. as a substituent on $R^6$, can be obtained by starting from the corresponding N-hydroxy-benzamidines. N-Hydroxy-benzamidines can be converted to the desired compounds using methods well known to somebody skilled in the art, e.g. intramolecular sulfinamidate formation. The reaction is typically carried out in an aprotic solvent like dimethylformamide, dimethyl sulfoxide, acetonitrile, tetrahydrofuran or dichloromethane or mixtures thereof in the presence of a base. A typically used reagent is thionyl chloride and typical bases are triethylamine, diisopropylethylamine, 4-methylmorpholine or pyridine.

Compounds which carry an acid isostere such as 5-thioxo-4H-[1,2,4]oxadiazol-3-yl, e.g. as a substituent on $R^6$, can be obtained by starting from the corresponding N-hydroxy-benzamidines. The N-Hydroxy-benzamidines can be converted to the desired compounds using methods well known to somebody skilled in the art, e.g. intramolecular thiocarbamate formation. The reaction is typically carried out in an aprotic solvent like dimethyl-formamide, dimethyl sulfoxide, acetonitrile, tetrahydrofuran or dichloromethane or mixtures thereof in the presence of a base. A typically used reagent is 1,1'-thiocarbonyl-diimidazole and typical bases are triethylamine, diisopropylethylamine, 4-methyl-morpholine, 1,8-diazabicyclo[5.4.0]undec-7-cene (DBU), 1,5-diazabicyclo[4.3.0]non-5-ene and the like or pyridine.

Compounds which carry an acid isostere such as 5-oxo-4H-[1,2,4]thiadiazol-3-yl, e.g. as a substituent on $R^6$, can be obtained by starting from the corresponding N-hydroxy-benzamidines. The N-hydroxy-benzamidines can be converted to the desired compounds using methods well known to somebody skilled in the art, e.g. intramolecular thiocarbamate formation. The reaction is typically carried out in an aprotic solvent like dimethyl-formamide, dimethyl sulfoxide, acetonitrile, tetrahydrofuran or dichloromethane or mixtures thereof in the presence of a Lewis acid. A typically used reagent is 1,1'-thiocarbonyldiimidazole and a typical acids is boron trifluoride.

Compounds which carry a tertiary hydroxyl, e.g. in a substituent on $R^6$, can be obtained by starting from the corresponding ketones. The ketones are obtained as described in schemes 1-14 by employing an appropriate (alkylcarbonyl)-amino-arene in the amide formation step. The Ketones can be converted to the desired compounds using methods well known to somebody skilled in the art, e.g. Grignard addition or addition of other organometallic reagents, or reagents capable of generating a nucleophilic carbon under the reaction conditions. The reaction is typically carried out in an aprotic solvent like tetrahydrofuran, ether or dichloromethane or mixtures thereof at temperatures between −80° C. and 25° C. under anhydrous conditions.

Compounds of formula (I) which comprise an acid group such as COOH or an acid isostere can form salts with physiologically compatible bases. Examples of such salts are alkaline, earth-alkaline and ammonium salts such as e.g. sodium, potassium, calcium and trimethylammonium salt. One method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU). Pharmaceutically acceptable esters can furthermore be prepared by treatment of a suitable hydroxy group present in the molecule with a suitable acid, optionally or if necessary in the presence of a condensating agent as described above.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention have been found to inhibit liver carnitine palmitoyl transferase 1 (L-CPT1) activity. The compounds of the present invention can therefore be used in the treatment and/or prophylaxis of diseases which are modulated by L-CPT1 inhibitors, particularly diseases which are related to hyperglycemia and/or glucose tolerance disorders. Such diseases include e.g. diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by L-CPT1 inhibitors, particularly as therapeutically active substances for the treatment and/or prophylaxis of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

In another preferred embodiment, the invention relates to a method for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure, which method comprises administering a compound as defined above to a human being or animal.

The invention also embraces the use of compounds as defined above for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention also relates to the use of compounds as described above for the preparation of medicaments for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure. Such medicaments comprise a compound as described above.

Prevention and/or treatment of hyperglycemia and non insulin dependent diabetes mellitus is the preferred indication.

The following tests were carried out in order to determine the activity of the compounds of the present invention. Background information on the performed assays can be found in: Jackson et al., 1999, *Biochem. J.* 341, 483-489 and Jackson et al., 2000, *J. Biol. Chem.* 275, 19560-19566.

Human liver and muscle CPT1 cDNAs and rat CPT2 cDNA were subcloned in pGAPZB or pGAPZA, respectively. These plasmids were used to transform *P. pastoris* strain X-33 via electroporation after the preparation of electrocompetent cells. High copy number clones were selected where necessary using 0.5 or 1 mg/ml Zeocin. Cultures for activity measurements were induced for 16 h in YPD medium (1% yeast extract, 2% peptone, 2% glucose). Crude cell extracts were prepared by disrupting the cells with glass beads or French Press, depending on fermenter sizes. After centrifugation, the cell-free extracts were resuspended in cell breaking buffer (50 mM Tris, pH7.4, 100 mM KCl, 1 mM EDTA) in the presence of a protease inhibitor cocktail, before aliquoting and freezing at −20° C.

CPT activity was measured using a spectrophotometric assay using 5,5'-dithio-bis-(2-nitrobenzoic acid) (DTNB)

also called Ellman's reagent. The HS-CoA released on the formation of acylcarnitine from carnitine (500 μM) and palmitoyl-CoA (80 μM) reduced DTNB (300 μM) forming 5-mercapto-(2-nitrobenzoic acid) which absorbed at 410 nm with a molar extinction coefficient of 13600 $M^{-1} \cdot cm^{-1}$. The assay buffer contained 120 mM KCl, 25 mM Tris, pH 7.4, 1 mM EDTA. This assay was used for the identification of selective inhibitors of the liver CPT1 isoform versus the muscle CPT1 and CPT2 isoforms.

The compounds according to formula (I) preferably have an 1050 value below 10 M, preferably 10 nM to 10 M, more preferably 10 nM to 5 M. The following table shows data for some examples.

| Example | L-CPT1 inhibition $IC_{50}$ [mol/l] |
|---------|---------------------------------------|
| 2       | 0.078                                 |
| 32      | 0.140                                 |
| 73      | 0.056                                 |
| 92      | 0.023                                 |
| 113     | 0.016                                 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-200 mg, of a compound of formula I.

The following Examples serve to illustrate the present invention in more detail. They are, however, not intended to limit its scope in any manner.

EXAMPLES

Example 1

4-{[4-(5-Chloro-2-methoxy-benzenesulfonyl)-3,4-dihydro-2H-benzo[1,4]oxazine-6-carbonyl]-amino}-benzoic acid 4-{[4-(5-Chloro-2-methoxy-benzenesulfonyl)-3,4-dihydro-2H-benzo[1,4]oxazine-6-carbonyl]-amino}-benzoic acid was prepared as illustrated in scheme 1.

Step 1. A solution of 4-hydroxy-3-nitro-benzoic acid methyl ester (5.0 g, 25.4 mmol) in ethanol (120 mL) was treated with 5% palladium on active carbon (0.24 g, 2.3 mmol, 0.1 equiv.) and the flask was evacuated and placed under an hydrogen atmosphere. The mixture was stirred vigorously for 2 h and 45', the palladium was filtered off, washing extensively with ethanol. The solvent was removed in vacuo to yield 3-amino-4-hydroxy-benzoic acid methyl ester as a white solid, 4.2 g (100%), MS (ISP): m/e=168.3 $(M+H^{+\cdot})$. This was used crude in the following reaction.

Step 2. A solution of 3-amino-4-hydroxy-benzoic acid methyl ester (4.2 g, 25.4 mmol) in dimethylformamide (85 mL) was treated with $K_2CO_3$ (14.2 g, 102.9 mmol, 4 equiv.) and 1,2-dibromoethane (19.3 g, 102.9 mmol, 4 equiv.). The mixture was stirred at 70° C. overnight, then filtered to remove the solids. The filtrate was removed under vacuo, and the residue was purified by flash chromatography (heptane/ethyl acetate gradient) to yield 3,4-dihydro-2H-benzo[1,4]oxazine-6-carboxylic acid methyl ester, 3.65 g (73%) as a light yellow solid, MS (ISP): m/e=235.1 $(M+CH_3CN^{+\cdot})$; $\delta_H$ (300 MHz; $CDCl_3$) 7.36 (1H, dd, J=8.5, 2.0), 7.30 (1H, d, J=2.0), 6.78 (1H, d, J=8.5), 4.30 (2H, m); 3.85 (3H, s), 3.43 (2H, m).

Step 3. To a solution of 5-chloro-2-methoxy-benzenesulfonyl chloride (4.7 g, 19.7 mmol, 1.05 equiv.) in dichloromethane (60 mL) and pyridine (25 mL) was added a solution of 3,4-dihydro-2H-benzo[1,4]oxazine-6-carboxylic acid methyl ester (3.6 g, 18.8 mmol, 1 equiv.) in dichloromethane (60 mL). The mixture was stirred at room temperature overnight then the solvent was removed. The residue was purified by flash chromatography to yield 4-(5-chloro-2-methoxybenzenesulfonyl)-3,4-dihydro-2H-benzo[1,4]oxazine-6-carboxylic acid methyl ester as a pink solid, 7.12 g (95%), MS (ISP): m/e=398.0 $(M+H^{+\cdot})$; $\delta_H$ (300 MHz; $CDCl_3$) 8.24 (1H, s), 8.07 (1H, s), 7.72 (1H, dd), 7.48 (1H, dd), 6.91 (1H, d), 6.89 (1H, d), 4.10 (2H, m), 3.91 (2H, m), 3.88 (3H, s), 3.63 (3H, s).

Step 4. A solution of 4-(5-chloro-2-methoxy-benzenesulfonyl)-3,4-dihydro-2H-benzo[1,4]oxazine-6-carboxylic acid methyl ester (7.1 g, 17.8 mmol) in tetrahydrofuran (100 mL) and methanol (50 mL) was treated with 3N NaOH (25 mL, 75 mmol, 4.2 equiv.). The mixture was stirred at 45° C. for 1.5 hours. The organic solvents were then removed and the residue acidified with HCl 3N (25 mL). The white precipitate which formed was filtered, washing with water, and dried under high vacuum. 4-(5-Chloro-2-methoxy-benzenesulfonyl)-3,4-dihydro-2H-benzo[1,4]oxazine-6-carboxylic acid was obtained as a white solid, 6.79 g (99%), MS (ISP): m/e=382.0 (M−H), which was used crude in the following reaction.

Step 5. A suspension of 4-(5-chloro-2-methoxy-benzenesulfonyl)-3,4-dihydro-2H-benzo[1,4]oxazine-6-carboxylic acid (1.0 g, 2.6 mmol) in acetone (130 mL) and tetrahydrofuran (30 mL) was treated with triethylamine (0.5 g, 0.68 mL, 1.9 equiv.) and stirred at room temperature overnight. A solution of cyanuric chloride (596 mg, 3.2 mmol, 1.24 equiv.) in acetone (20 mL) was added dropwise over a period of 1 hour. The reaction mixture was stirred at room temperature for 4 hours, 4-amino-benzoic acid ethyl ester (775 mg, 4.7 mmol, 1.8 equiv.) was then added. The reaction mixture was stirred at room temperature overnight, the solvents were then removed. The residue was purified by flash chromatography, to yield 4-{[4-(5-chloro-2-methoxy-benzenesulfonyl)-3,4-dihydro-2H-benzo[1,4]oxazine-6-carbonyl]-amino}-benzoic acid ethyl ester as a white solid, 0.91 g (66%). $\delta_H$ (300 MHz; CDCl$_3$) 8.10 (1H, d), 8.03-8.07 (3H, m), 7.92 (1H, bs), 7.73 (2H, d), 7.70 (1H, d), 7.67 (1H, d), 7.53 (1H, d), 7.50 (1H, d), 4.37 (2H, q), 4.03 (2H, m), 3.88 (2H, m), 3.56 (3H, s), 1.40 (3H, t).

Step 6. A solution of 4-{[4-(5-chloro-2-methoxy-benzenesulfonyl)-3,4-dihydro-2H-benzo-[1,4]oxazine-6-carbonyl]-amino}-benzoic acid ethyl ester (0.91 g, 1.72 mmol) in tetrahydrofuran (10 mL) and methanol (10 mL) was treated with 3N NaOH (5 mL, 15 mmol, 8.7 equiv.). The mixture was stirred at 45° C. for 30'. The mixture was then acidified with HCl 3N (5 mL) and the solid which precipitated was filtered, washing with water, and dried under high vacuum. 4-{[4-(5-Chloro-2-methoxy-benzenesulfonyl)-3,4-dihydro-2H-benzo[1,4]oxazine-6-carbonyl]-amino}-benzoic acid was obtained as a white solid, 0.85 g (98%). MS (ISP): m/e=501.0 (M−H); $\delta_H$ (300 MHz; d6-DMSO) 12.65 (1H, s), 10.35 (1H, s), 8.05 (1H, d), 7.81-7.88 (5H, m), 7.66-7.71 (2H, m), 7.19 (1H, d), 6.98 (1H, d), 3.96 (2H, m), 3.85 (2H, m), 3.53 (3H, s).

Example 2

4-{[4-(5-Chloro-2-methoxy-benzenesulfonyl)-3,4-dihydro-2H-benzo[1,4]oxazine-6-carbonyl]-amino}-2-fluoro-benzoic acid 4-{[4-(5-Chloro-2-methoxy-benzenesulfonyl)-3,4-dihydro-2H-benzo[1,4]oxazine-6-carbonyl]-amino}-2-fluoro-benzoic acid, MS (ISP): m/e=519.0 (M−H), was prepared as described in example 1, steps 1 to 6. Step 5 was performed using 4-amino-2-fluoro-benzoic acid ethyl ester and yielded 4-{[4-(5-chloro-2-methoxy-benzenesulfonyl)-3,4-dihydro-2H-benzo[1,4]oxazine-6-carbonyl]-amino}-2-fluoro-benzoic acid ethyl ester, which was hydrolyzed in step 6.

Example 3

2-Chloro-4-{[4-(5-chloro-2-methoxy-benzenesulfonyl)-3,4-dihydro-2H-benzo[1,4]oxazine-6-carbonyl]-amino}-benzoic acid 2-Chloro-4-{[4-(5-chloro-2-methoxy-benzenesulfonyl)-3,4-dihydro-2H-benzo[1,4]oxazine-6-carbonyl]-amino}-benzoic acid, MS (ISP): m/e=534.9, 536.9 (M−H), was prepared as described in example 1, steps 1 to 6. Step 5 was performed using 4-amino-2-chloro-benzoic acid methyl ester and yielded 2-chloro-4-{[4-(5-chloro-2-methoxy-benzenesulfonyl)-3,4-dihydro-2H-benzo-[1,4]oxazine-6-carbonyl]-amino}-benzoic acid methyl ester, which was hydrolyzed in step 6.

Example 4

5-{[4-(5-Chloro-2-methoxy-benzenesulfonyl)-3,4-dihydro-2H-benzo[1,4]oxazine-6-carbonyl]-amino}-pyridine-2-carboxylic acid 5-{[4-(5-Chloro-2-methoxy-benzenesulfonyl)-3,4-dihydro-2H-benzo[1,4]oxazine-6-carbonyl]-amino}-pyridine-2-carboxylic acid, MS (ISP): m/e=502.0, 503.9 (M−H), was prepared as described in example 1, steps 1 to 6. Step 5 was performed using 5-amino-pyridine-2-carboxylic acid ethyl ester and yielded 5-{[4-(5-chloro-2-methoxy-benzenesulfonyl)-3,4-dihydro-2H-benzo[1,4]oxazine-6-carbonyl]-amino}-pyridine-2-carboxylic acid ethyl ester, which was hydrolyzed in step 6.

Example 5

4-{[4-(5-Chloro-2-methoxy-benzenesulfonyl)-3,4-dihydro-2H-benzo[1,4]oxazine-6-carbonyl]-amino}-2-methoxy-benzoic acid 4-{[4-(5-Chloro-2-methoxy-benzenesulfonyl)-3,4-dihydro-2H-benzo[1,4]oxazine-6-carbonyl]-amino}-2-methoxy-benzoic acid, MS (ISP): m/e=531.0 (M−H), was prepared as described in example 1, steps 1 to 6. Step 5 was performed using 4-amino-2-methoxy-benzoic acid ethyl ester and yielded 4-{[4-(5-chloro-2-methoxy-benzenesulfonyl)-3,4-dihydro-2H-benzo[1,4]oxazine-6-carbonyl]-amino}-2-methoxy-benzoic acid ethyl ester, which was hydrolyzed in step 6.

Example 6

4-{[4-(5-Chloro-2-methoxy-benzenesulfonyl)-3,4-dihydro-2H-benzo[1,4]oxazine-6-carbonyl]-amino}-2-methyl-benzoic acid 4-{[4-(5-Chloro-2-methoxy-benzenesulfonyl)-3,4-dihydro-2H-benzo[1,4]oxazine-6-carbonyl]-amino}-2-methyl-benzoic acid, MS (ISP): m/e=515.0 (M−H), was prepared as described in example 1, steps 1 to 6. Step 5 was performed using 4-amino-2-methyl-benzoic acid ethyl ester and yielded 4-{[4-(5-chloro-2-methoxy-benzenesulfonyl)-3,4-dihydro-2H-benzo[1,4]oxazine-6-carbonyl]-amino}-2-methyl-benzoic acid ethyl ester, which was hydrolyzed in step 6.

Example 7

4-{[4-(5-Chloro-2-methoxy-benzenesulfonyl)-3,4-dihydro-2H-benzo[1,4]oxazine-6-carbonyl]-amino}-3-methyl-benzoic acid 4-{[4-(5-Chloro-2-methoxy-benzenesulfonyl)-3,4-dihydro-2H-benzo[1,4]oxazine-6-carbonyl]-amino}-3-methyl-benzoic acid, MS (ISP): m/e=515.3 (M−H), was prepared as described in example 1, steps 1 to 6. Step 5 was performed using thionyl chloride in toluene and dimethyl-formamide for the formation of the acyl chloride, and 4-amino-3-methyl-benzoic acid methyl ester was used for the coupling, yielding 4-{[4-(5-chloro-2-methoxy-benzenesulfonyl)-3,4-dihydro-2H-benzo[1,4]oxazine-6-carbonyl]-amino}-3-methyl-benzoic acid methyl ester, which was hydrolyzed in step 6.

Example 8

2-{[4-(5-Chloro-2-methoxy-benzenesulfonyl)-3,4-dihydro-2H-benzo[1,4]oxazine-6-carbonyl]-amino}-thiazole-4-carboxylic acid 2-{[4-(5-Chloro-2-methoxy-benzenesulfonyl)-3,4-dihydro-2H-benzo[1,4]oxazine-6-carbonyl]-amino}-thiazole-4-carboxylic acid, MS (ISP): m/e=508.3 (M−H), was prepared as described in example 1, steps 1 to 6. Step 5 was performed using thionyl chloride in toluene and dimethylformamide for the formation of the acyl chloride, and 2-amino-thiazole-4-carboxylic acid ethyl ester was used for the coupling, yielding 2-{[4-(5-chloro-2-methoxy-benzenesulfonyl)-3,4-dihydro-2H-benzo[1,4]oxazine-6-carbonyl]-amino}-thiazole-4-carboxylic acid ethyl ester, which was hydrolyzed in step 6.

Example 9

4-(5-Chloro-2-methoxy-benzenesulfonyl)-3,4-dihydro-2H-benzo[1,4]oxazine-6-carboxylic acid [4-(1H-tetrazol-5-yl)-phenyl]-amide Step 1. A solution of 4-(5-chloro-2-methoxy-benzenesulfonyl)-3,4-dihydro-2H-benzo[1,4]oxazine-6-carboxylic acid (example 1, steps 1 to 4) (1.0 g, 2.6 mmol) in dichloromethane (50 mL) was treated with N,N-diisopropyl ethyl amine (0.34 g, 2.6 mmol) and cooled to 0° C. Bromo-tris-pyrrolidino-phosphonium hexafluorophosphate (2.4 g, 5.2 mmol) was added, and the mixture was stirred at 0° C. for 1 min. 4-Aminobenzonitrile (1.2 g, 10.4 mmol) was added and the mixture was stirred at room temperature overnight. The solvent was evaporated, and the crude was purified by flash chromatography (heptane/ethyl acetate gradient) yielding 4-(5-chloro-2-methoxybenzenesulfonyl)-3,4-dihydro-2H-benzo[1,4]oxazine-6-carboxylic acid (4-cyano-phenyl)-amide as a white solid, 0.18 g (14%), MS (ISP): m/e=482.0 (M−H).

Step 2. A microwave tube was charged with a solution of 4-(5-chloro-2-methoxybenzenesulfonyl)-3,4-dihydro-2H-benzo[1,4]oxazine-6-carboxylic acid (4-cyano-phenyl)-amide (50 mg, 0.10 mmol) in dimethylformamide (2.0 mL). Ammonium chloride (102 mg, 1.9 mmol) and sodium azide (121 mg, 1.9 mmol) were added and the tube was sealed under an argon atmosphere and irradiated in a microwave oven at a temperature of 155° C. for 35 min. The mixture was then acidified with HCl 1N and extracted three times with ethyl acetate. The combined organic extracts were dried over sodium sulfate and evaporated. The crude was resuspended in dichloromethane and sonicated. Filtration yielded 4-(5-chloro-2-methoxy-benzenesulfonyl)-3,4-dihydro-2H-benzo[1,4]oxazine-6-carboxylic acid [4-(1H-tetrazol-5-yl)-phenyl]-amide as a white solid, 35 mg (64%), MS (ISP): m/e=525.0, 527.0 (M−H).

Example 10

4-(5-Chloro-2-methoxy-benzenesulfonyl)-3,4-dihydro-2H-benzo[1,4]oxazine-6-carboxylic acid [4-(5-oxo-4,5-dihydro-[1,2,4]oxadiazol-3-yl)-phenyl]-amide Step 1. A solution of hydroxylamine hydrochloride (90 mg, 1.3 mmol) in dimethyl sulfoxide (1.25 mL) was treated with triethylamine (131 mg, 0.18 mL, 1.3 mmol) and stirred at room temperature for 5 min. The solids were filtered off, and 4-(5-chloro-2-methoxy-benzenesulfonyl)-3,4-dihydro-2H-benzo[1,4]oxazine-6-carboxylic acid (4-cyano-phenyl)-amide (125 mg, 0.26 mmol) was added. The mixture was stirred at 75° C. for 1.5 hours. After cooling back to room temperature, the mixture was diluted with water and extracted with ethyl acetate. The organic phase was extracted three times with 0.5N HCl. The combined acidic aqueous layer was then rebasified with 1N NaOH and extracted three times with ethyl acetate. The organic layer was washed with water, dried over sodium sulfate and evaporated. 4-(5-Chloro-2-methoxy-benzenesulfonyl)-3,4-dihydro-2H-benzo[1,4]oxazine-6-carboxylic acid [4-(N-hydroxycarbamimidoyl)-phenyl]-amide was obtained as a white solid, 97 mg (73%), MS (ISP): m/e=517.0 (M+H$^+$).

Step 2. A solution of 4-(5-chloro-2-methoxy-benzenesulfonyl)-3,4-dihydro-2H-benzo[1,4]oxazine-6-carboxylic acid [4-(N-hydroxycarbamimidoyl)-phenyl]-amide (97 mg, 0.19 mmol) in dimethylformamide (2.0 mL) was treated with pyridine (0.020 mL, 0.20 mmol) and the mixture was cooled at 0° C. Chloroformic acid 2-ethylhexyl ester (36 mg, 0.19 mmol) was added dropwise and the mixture was stirred at 0° C. for 30 min. The mixture was diluted with water and extracted three times with ethyl acetate. The combined organic extracts were dried over sodium sulfate and evaporated. The residue was suspended in xylene (8.0 mL) and refluxed for 2 hours. Upon cooling to room temperature a solid precipitated, which was filtered and dried under high vacuum. 4-(5-Chloro-2-methoxy-benzenesulfonyl)-3,4-dihydro-2H-benzo[1,4]oxazine-6-carboxylic acid [4-(5-oxo-4,5-dihydro-[1,2,4]oxadiazol-3-yl)-phenyl]-amide was obtained as a white solid, 74 mg (73%), MS (ISP): m/e=541.1, 542.7 (M−H).

Example 11

4-{[4-(5-Chloro-2-methoxy-benzenesulfonyl)-1,2,3,4-tetrahydro-quinoxaline-6-carbonyl]-amino}-benzoic acid The title compound was prepared as illustrated in scheme 12.

Step 1. 4-Amino-3-nitrobenzoic acid (5.0 g, 27.4 mmol) was dissolved in ethanol (100 mL) and treated with a 2N solution of HCl in ether (30 mL). The reaction mixture was refluxed for 16 h, then the solvent was removed in vacuo. The crude compound was dissolved in dichloromethane and washed with NaOH 0.5N. The organic phase was dried over sodium sulfate and the solvent was removed. 4-Amino-3-nitrobenzoic acid ethyl ester was thus obtained as a yellow solid, 4.6 g, (79%), MS (ISP): m/e=211.1 (M+H$^+$), and used crude in the following reaction.

Step 2. A solution of 4-amino-3-nitrobenzoic acid ethyl ester (4.1 g, 19.7 mmol) in acetonitrile (30 mL) was treated with triethylamine (25 mL) and dimethylaminopyridine (0.24 g, 2.0 mmol). Di-tert-butyl dicarbonate (6.5 g, 29.6 mmol) was added dropwise at room temperature over a period of 30 minutes. The reaction mixture was stirred at room temperature overnight. The mixture was diluted with water and dichloromethane. The organic phase was separated, dried over sodium sulfate and the volatiles were then evaporated. The residue was redissolved in dichloromethane (150 mL) and cooled to 0° C. Trifluoroacetic acid (6.0 mL) was added, and the mixture was stirred at 0° C. for 2 hours. The mixture was diluted with saturated NaHCO$_3$ and the organic phase was separated. The aqueous phase was extracted twice with dichloromethane. The combined organic phases were dried over sodium sulfate and evaporated. The residue was purified by flash chromatography (dichloromethane/methanol gradient), yielding 4-tert-butoxycarbonylamino-3-nitro-benzoic acid ethyl ester as a light yellow solid, 3.5 g (57%), MS (ISP): m/e=309.4 (M−H).

Step 3. 4-Tert-butoxycarbonylamino-3-nitro-benzoic acid ethyl ester (3.5 g, 11.3 mmol) was dissolved in ethanol (300 mL) and 10% palladium on carbon was added (0.45 g, 0.42 mmol). The mixture was evacuated and filled with hydrogen, then stirred at room temperature for 1 hour. The catalyst was filtered, washing with ethanol, and the solvent was evaporated. The crude 3-amino-4-tert-butoxycarbonylamino-benzoic acid ethyl ester thus obtained [3.1 g, 95%, MS (ISP): m/e=279.3 (M−H)] was used as such in the following reaction.

Step 4. 3-Amino-4-tert-butoxycarbonylamino-benzoic acid ethyl ester (3.1 g, 11.1 mmol) was dissolved in dimethylformamide (50 mL) and treated with NaH (~55% dispersion in oil) (0.3 g, 12.2 mmol). The reaction mixture was stirred at room temperature for 1 hour, dibromoethane (8.3 g, 3.8 mL, 44.2 mmol) was then added, and the mixture stirred for further 1 hour at room temperature. K$_2$CO$_3$ (6.11 g, 44.2 mmol) was added and the reaction mixture was stirred at 70° C. for 17 hours. A further aliquot of NaH (~55% dispersion in oil) (0.3 g, 12.2 mmol) was added and, 3 hours later, a further aliquot of dibromoethane (2.1 g, 11.1 mmol). Stirring was continued at 70° C. for 18 hours. Water was added and the mixture was extracted three times with dichloromethane. The combined organic phases were dried over sodium sulfate and evaporated. The residue was purified by flash chromatography, yielding 3,4-dihydro-2H-quinoxaline-1,6-dicarboxylic acid 1-tert-butyl ester 6-ethyl ester as a light yellow solid, 1.0 g (29%), MS (ISP): m/e=307.3 (M+H$^+$); $\delta_H$ (300 MHz; CDCl$_3$) 7.58 (1H, d), 7.34 (1H, d), 7.25 (1H, s), 4.33 (2H, q), 4.09 (1H, bs), 3.79 (2H, m), 3.43 (2H, m), 1.53 (9H, s), 1.37 (3H, t).

Step 5. 3,4-Dihydro-2H-quinoxaline-1,6-dicarboxylic acid 1-tert-butyl ester 6-ethyl ester (300 mg, 0.98 mmol) was dissolved in dichloromethane (20 mL) and pyridine (2 mL). N,N-Diisopropylethylamine (127 mg, 0.98 mmol) and 5-chloro-2-methoxy-benzenesulfonyl chloride (300 mg, 1.24 mmol) were added, and the mixture was stirred at room temperature overnight. The solvent was evaporated, and the crude compound was purified by flash chromatography, yielding 4-(5-chloro-2-methoxy-benzenesulfonyl)-3,4-dihydro-2H-quinoxaline-1,6-dicarboxylic acid 1-tert-butyl ester 6-ethyl ester as a light yellow gum, 435 mg (87%), $_H$ (300 MHz; CDCl$_3$) 8.17 (1H, s), 8.05 (1H, s), 7.82 (1H, d), 7.74 (1H, d), 7.46 (1H, dd), 6.82 (1H, d), 4.35 (2H, q), 3.93 (2H, m), 3.71 (2H, m), 3.56 (3H, s), 1.48 (9H, s), 1.39 (3H, t).

Step 6. A solution of 4-(5-chloro-2-methoxy-benzenesulfonyl)-3,4-dihydro-2H-quinoxaline-1,6-dicarboxylic acid 1-tert-butyl ester 6-ethyl ester (430 mg, 0.84 mmol) in tetrahydrofuran (10 mL) and methanol (10 mL) was treated with 2N NaOH (5 mL). The mixture was stirred at room temperature for 1 hour. The organic solvents were then partially removed and the residue acidified with HCl 1N (10 mL). The precipitate which formed was filtered, washing with water, and dried under high vacuum. 4-(5-Chloro-2-methoxy-benzenesulfonyl)-3,4-dihydro-2H-quinoxaline-1,6-dicarboxylic acid 1-tert-butyl ester was obtained as a light yellow gum, 386 mg (95%), MS (ISP): m/e=481.1 (M−H), which was used crude in the following reaction.

Step 7. A solution of 4-(5-chloro-2-methoxy-benzenesulfonyl)-3,4-dihydro-2H-quinoxaline-1,6-dicarboxylic acid 1-tert-butyl ester (100 mg, 0.21 mmol) in acetone (30 mL) and tetrahydrofuran (10 mL) was treated with triethylamine (21 mg, 0.21 mmol) and stirred at room temperature 1 hour. A solution of cyanuric chloride (46 mg, 0.25 mmol) in tetrahydrofurane (2 mL) was added dropwise over a period of 1 hour. The reaction mixture was stirred at room temperature for 2 hours, then 4-amino-benzoic acid ethyl ester (51 mg, 0.31 mmol) and a further aliquot of triethylamine (42 mg, 0.42 mmol) were added. The reaction mixture was stirred at room temperature for 48 hours, the solvents were then removed. The residue was purified by flash chromatography, to yield 4-(5-chloro-2-methoxy-benzenesulfonyl)-6-(4-ethoxycarbonyl-phenylcarbamoyl)-3,4-dihydro-2H-quinoxaline-1-carboxylic acid tert-butyl ester as a light yellow solid, 100 mg (77%), $\delta_H$ (300 MHz; CDCl$_3$) 8.01-8.08 (4H, m), 7.94 (1H, d), 7.73-7.77 (3H, m), 7.48 (1H, dd), 6.82 (1H, d), 4.38 (2H, q), 3.89 (2H, m), 3.64 (2H, m), 3.47 (3H, s), 1.48 (9H, s), 1.40 (3H, t).

Step 8. A solution of 4-(5-chloro-2-methoxy-benzenesulfonyl)-6-(4-ethoxycarbonyl-phenylcarbamoyl)-3,4-dihydro-2H-quinoxaline-1-carboxylic acid tert-butyl ester (95 mg, 0.15 mmol) in trifluoroacetic acid (2 mL) was stirred at room temperature 2 hours. The volatiles were removed and the residue was purified by trituration in dichloromethane. 4-{[4-(5-Chloro-2-methoxy-benzenesulfonyl)-1,2,3,4-tetrahydro-quinoxaline-6-carbonyl]-amino}-benzoic acid ethyl ester was obtained as a white solid, 61 mg (76%), MS (ISP): m/e=530.3, 532.3 (M+H$^+$).

Step 9. A suspension of 4-{[4-(5-chloro-2-methoxy-benzenesulfonyl)-1,2,3,4-tetrahydro-quinoxaline-6-carbonyl]-amino}-benzoic acid ethyl ester (30 mg, 0.06 mmol) in tetrahydrofuran (2 mL) and methanol (2 mL) was treated with NaOH 2N (2 mL) and warmed until a clear solution was obtained. The mixture was stirred at room temperature 2 hours, the organic solvents were then partially removed. The aqueous slurry was acidified with HCl 1N (4 mL) and the resulting precipitate filtered, washing with water. 4-{[4-(5-Chloro-2-methoxy-benzenesulfonyl)-1,2,3,4-tetrahydro-quinoxaline-6-carbonyl]-amino}-benzoic acid was obtained as a white solid, 26 mg (91%), MS (ISP): m/e=499.9, 501.9 (M−H); $\delta_H$ (300 MHz; d6-DMSO) 12.67 (1H, s), 10.15 (1H, s), 7.91 (4H, s), 7.89 (1H, s), 7.81 (1H, s), 7.73 (1H, d), 7.63 (1H, d), 7.23 (1H, d), 6.88 (1H, bs), 6.66 (1H, d), 3.64 (2H, bs), 3.53 (3H, s), 2.99 (2H, bs).

Example 12

5-{[4-(5-Chloro-2-methoxy-benzenesulfonyl)-1,2,3,4-tetrahydro-quinoxaline-6-carbonyl]-amino}-pyridine-2-carboxylic acid 5-{[4-(5-Chloro-2-methoxy-benzenesulfonyl)-1,2,3,4-tetrahydro-quinoxaline-6-carbonyl]-amino}-pyridine-2-carboxylic acid, MS (ISP): m/e=503.3 (M+H$^+$), was prepared as described in example 11, steps 1 to 9. Step 7 was performed using 5-amino-pyridine-2-carboxylic acid ethyl ester and yielded 4-(5-chloro-2-methoxy-benzenesulfonyl)-6-(6-ethoxycarbonyl-pyridin-3-ylcarbamoyl)-3,4-dihydro-2H-quinoxaline-1-carboxylic acid tert-butyl ester. This was deprotected in step 8 to 5-{[4-(5-chloro-2-methoxy-benzenesulfonyl)-1,2,3,4-tetrahydro-quinoxaline-6-carbonyl]-amino}-pyridine-2-carboxylic acid ethyl ester, which was hydrolyzed to the title compound in step 9.

Example 13

4-{[4-(5-Chloro-2-methoxy-benzenesulfonyl)-1,2,3,4-tetrahydro-quinoxaline-6-carbonyl]-amino}-2-fluoro-benzoic acid 4-{[4-(5-Chloro-2-methoxy-benzenesulfonyl)-1,2,3,4-tetrahydro-quinoxaline-6-carbonyl]-amino}-2-fluoro-benzoic acid, MS (ISP): m/e=518.0 (M−H), was prepared as described in example 11, steps 1 to 9. Step 7 was performed using 4-amino-2-fluoro-benzoic acid ethyl ester and yielded 4-(5-chloro-2-methoxy-benzenesulfonyl)-6-(4-ethoxycarbonyl-3-fluoro-phenylcarbamoyl)-3,4-dihydro-2H-quinoxaline-1-carboxylic acid tert-butyl ester. This was deprotected in step 8 to 4-{[4-(5-chloro-2-methoxy-benzenesulfonyl)-1,2,3,4-tetrahydro-quinoxaline-6-carbonyl]-amino}-2-fluoro-benzoic acid ethyl ester, which was hydrolyzed to the title compound in step 9.

Example 14

4-{[4-(3-Fluoro-benzenesulfonyl)-3,4-dihydro-2H-benzo[1,4]oxazine-6-carbonyl]-amino}-benzoic acid The title compound was prepared as illustrated in schemes 2 and 3.

Step 1. A solution of 4-hydroxy-3-nitro-benzoic acid methyl ester (30 g, 152 mmol) in acetone (1000 mL) was charged into a 2 L reactor and treated with $K_2CO_3$ (31.5 g, 228 mol) and benzyl bromide (52 g, 36.1 mL, 304 mmol). The mixture was mechanically stirred at heated at reflux for 16 hours under a light argon flux. After cooling to room temperature the solvent was evaporated. The residue was taken up in ethyl acetate/water and the two phases were separated. The aqueous phase was extracted three times with ethyl acetate (total solvent volume: 1.5 L, total water volume 1 L). The combined organic phases were dried over sodium sulfate and evaporated. 4-Benzyloxy-3-nitro-benzoic acid methyl ester thus obtained was used crude in the following reaction.

Step 2. A solution the crude 4-benzyloxy-3-nitro-benzoic acid methyl ester from the previous step in tetrahydrofurane (150 mL) and MeOH (600 mL) was treated with KOH 3N (152 mL) and stirred at room temperature for 18 hours. The mixture was acidified with HCl 3N. The precipitate thus formed was filtered, washing with MeOH/water 1:1 and dried under vacuum. 4-Benzyloxy-3-nitro-benzoic acid (42 g, 95% over two steps) was obtained as a white solid, which was used crude in the following reaction.

Step 3. A suspension of 4-benzyloxy-3-nitro-benzoic acid (36 g, 132 mmol) in toluene (1000 mL) and dimethylformamide (3 mL) was treated with thionyl chloride (47 g, 28.7 mL, 395 mmol) and stirred at 90° C. for 18 hours. The volatiles were evaporated completely and the residue dried under high vacuum. 4-Benzyloxy-3-nitro-benzoyl chloride thus obtained (37.5 g, 97%) was used crude in the following reaction.

Step 4. A solution of 4-amino-benzoic acid ethyl ester (17 g, 103 mmol) in dichloromethane (500 mL) and triethylamine (20.8 g, 28.5 mL, 206 mmol) was treated with dimethylaminopyridine (0.63 g, 5 mmol) and 4-benzyloxy-3-nitro-benzoyl chloride (30 g, 103 mmol). The mixture was stirred at room temperature overnight, while a thick white precipitate formed. The slurry was diluted with water (10 mL) and stirred vigorously, then filtered, washing with dichloromethane and water. The solid was dried under high vacuum to yield 4-(4-benzyloxy-3-nitro-benzoylamino)benzoic acid ethyl ester as a white solid, 26.5 g (61%), MS (ISP): m/e=419.3 (M−H).

Steps 5 and 6. A solution of 4-(4-benzyloxy-3-nitro-benzoylamino)-benzoic acid ethyl ester (26 g, 63 mmol) in DMF (2644 mL) was treated with 10% palladium on carbon (5.3 g). The reaction vessel was evacuated and filled with hydrogen. The mixture was stirred at room temperature for 4 hours, then the catalyst was filtered, washing with a small quantity of dimethylformamide. The resulting solution, containing crude 4-(3-amino-4-hydroxy-benzoylamino)-benzoic acid ethyl ester, was concentrated to a volume of 300 mL, and treated with $K_2CO_3$ (34.1 g, 247 mmol) and 1,2-dibromoethane (46.4 g, 247 mmol). The resulting mixture was warmed at 70° C. and stirred for 18 hours. The mixture was then concentrated to a volume of 100 mL and diluted with ethyl acetate and water. The organic phase was separated, washed three times with water, dried over sodium sulfate and evaporated. The residue was taken up in methanol and sonicated. The white solid was filtered, yielding pure 4-[(3,4-dihydro-2H-benzo[1,4]oxazine-6-carbonyl)-amino]-benzoic acid ethyl ester (8.6 g). The filtrate was evaporated and the residue purified by flash chromatography (toluene/acetonitrile gradient) providing further 2 g of material. 4-[(3,4-Dihydro-2H-benzo[1,4]oxazine-6-carbonyl)-amino]-benzoic acid ethyl ester was thus obtained as a white solid, 10.6 g (52%), MS (ISP): m/e=327.0 (M+H$^+$); $\delta_H$ (300 MHz; d6-DMSO) 10.27 (1H, s), 7.92 (4H, s), 7.16-7.19 (2H, m), 6.75 (1H, d), 6.04 (1H, s), 4.29 (2H, q), 4.19 (2H, s), 3.32 (2H, s), 1.32 (3H, t).

Step 7 and 8. A solution of 4-[(3,4-dihydro-2H-benzo[1,4] oxazine-6-carbonyl)-amino]-benzoic acid ethyl ester (27 mg, 0.085 mmol) in pyridine (0.4 mL) was treated with a solution of 3-fluoro-benzenesulfonyl chloride (25 mg, 0.13 mmol) in pyridine (0.2 mL). The resulting mixture was stirred at room temperature for 18 hours. The pyridine was evaporated, and the residual crude 4-{[4-(3-fluoro-benzenesulfonyl)-3,4-dihydro-2H-benzo[1,4]oxazine-6-carbonyl]-amino}-benzoic acid ethyl ester was dissolved in ethanol (0.6 mL) and treated with KOH 3N (0.15 mL). The resulting mixture was stirred at room temperature overnight. The mixture was acidified with HCl 3N and evaporated. The residue was purified by preparative HPLC (ZORBAX Eclipse XDB-C18, 21.2×50 mm, 5 µm, gradient acetonitrile/water+0.1% formic acid). 4-{[4-(3-Fluorobenzenesulfonyl)-3,4-dihydro-2H-benzo[1,4]oxazine-6-carbonyl]-amino}-benzoic acid (17.1 mg, 44%) was obtained as an off-white solid, MS (ISP): m/e=455.0 (M−H).

Example 15

4-{[4-(2,5-Difluoro-benzenesulfonyl)-3,4-dihydro-2H-benzo[1,4]oxazine-6-carbonyl]-amino}-benzoic acid 4-{[4-(2,5-Difluoro-benzenesulfonyl)-3,4-dihydro-2H-benzo[1,4]oxazine-6-carbonyl]-amino}-benzoic acid, MS (ISP): m/e=472.9 (M−H), was prepared as described for example 14, steps 1 to 8. Step 7 was performed using 2,5-difluoro-benzenesulfonyl chloride and yielded 4-{[4-(2,5-difluoro-benzenesulfonyl)-3,4-dihydro-2H-benzo[1,4]oxazine-6-carbonyl]-amino}-benzoic acid ethyl ester, which was hydrolyzed in step 8.

Example 16

4-{[4-(5-Fluoro-2-methyl-benzenesulfonyl)-3,4-dihydro-2H-benzo[1,4]oxazine-6-carbonyl]-amino}-benzoic acid 4-{[4-(5-Fluoro-2-methyl-benzenesulfonyl)-3,4-dihydro-2H-benzo[1,4]oxazine-6-carbonyl]-amino}-benzoic acid, MS (ISP): m/e=468.9 (M−H), was prepared as described for example 14, steps 1 to 8. Step 7 was performed using 5-fluoro-2-methyl-benzenesulfonyl chloride and yielded 4-{[4-(5-fluoro-2-methyl-benzenesulfonyl)-3,4-dihydro-2H-benzo[1,4]oxazine-6-carbonyl]-amino}-benzoic acid ethyl ester, which was hydrolyzed in step 8.

Example 17

4-{[4-(3-Difluoromethoxy-benzenesulfonyl)-3,4-dihydro-2H-benzo[1,4]oxazine-6-carbonyl]-amino}-benzoic acid 4-{[4-(3-Difluoromethoxy-benzenesulfonyl)-3,4-dihydro-2H-benzo[1,4]oxazine-6-carbonyl]-amino}-benzoic acid, MS (ISP): m/e=502.9 (M−H), was prepared as described for example 14, steps 1 to 8. Step 7 was performed using 3-difluoromethoxy-benzenesulfonyl chloride and yielded 4-{[4-(3-difluoromethoxy-benzenesulfonyl)-3,4-dihydro-2H-benzo[1,4]oxazine-6-carbonyl]-amino}-benzoic acid ethyl ester, which was hydrolyzed in step 8.

Example 18

4-{[4-(3,5-Dimethyl-benzenesulfonyl)-3,4-dihydro-2H-benzo[1,4]oxazine-6-carbonyl]-amino}-benzoic acid 4-{[4-(3,5-Dimethyl-benzenesulfonyl)-3,4-dihydro-2H-benzo[1,4]oxazine-6-carbonyl]-amino}-benzoic acid, MS (ISP): m/e=466.5 (M−H), was prepared as described for example 14, steps 1 to 8. Step 7 was performed using 3,5-dimethyl-benzenesulfonyl chloride and yielded 4-{[4-(3,5-dimethyl-benzenesulfonyl)-3,4-dihydro-2H-benzo[1,4]oxazine-6-carbonyl]-amino}-benzoic acid ethyl ester, which was hydrolyzed in step 8.

Example 19

4-{[4-(3-Trifluoromethyl-benzenesulfonyl)-3,4-dihydro-2H-benzo[1,4]oxazine-6-carbonyl]-amino}-benzoic acid 4-{[4-(3-Trifluoromethyl-benzenesulfonyl)-3,4-dihydro-2H-benzo[1,4]oxazine-6-carbonyl]-amino}-benzoic acid, MS (ISP): m/e=505.1 (M−H), was prepared as described for example 14, steps 1 to 8. Step 7 was performed using 3-trifluoromethyl-benzenesulfonyl chloride and yielded 4-{[4-(3-trifluoromethyl-benzenesulfonyl)-3,4-dihydro-2H-benzo[1,4]oxazine-6-carbonyl]-amino}-benzoic acid ethyl ester, which was hydrolyzed in step 8.

Example 20

4-{[4-(3-Chloro-benzenesulfonyl)-3,4-dihydro-2H-benzo[1,4]oxazine-6-carbonyl]-amino}-benzoic acid 4-{[4-(3-Chloro-benzenesulfonyl)-3,4-dihydro-2H-benzo[1,4]oxazine-6-carbonyl]-amino}-benzoic acid, MS (ISP): m/e=471.1 (M−H), was prepared as described for example 14, steps 1 to 8. Step 7 was performed using 3-chloro-benzenesulfonyl chloride and yielded 4-{[4-(3-chlorobenzenesulfonyl)-3,4-dihydro-2H-benzo[1,4]oxazine-6-carbonyl]-amino}-benzoic acid ethyl ester, which was hydrolyzed in step 8.

Example 21

2-Fluoro-4-{[4-(3-trifluoromethyl-benzenesulfonyl)-3,4-dihydro-2H-benzo[1,4]oxazine-6-carbonyl]-amino}-benzoic acid 2-Fluoro-4-{[4-(3-trifluoromethyl-benzenesulfonyl)-3,4-dihydro-2H-benzo[1,4]oxazine-6-carbonyl]-amino}-benzoic acid, MS (ISP): m/e=523.0 (M−H), was prepared as described for example 14, steps 1 to 8. Step 4 was performed using 4-amino-2-fluoro-benzoic acid ethyl ester, yielding 4-(4-benzyloxy-3-nitro-benzoylamino)-2-fluoro-benzoic acid ethyl ester, which was reduced to 4-(3-amino-4-hydroxy-benzoylamino)-2-fluoro-benzoic acid methyl ester in step 5 and cyclized to 4-[(3,4-dihydro-2H-benzo[1,4]oxazine-6-carbonyl)-amino]-2-fluoro-benzoic acid ethyl ester in step 6. Step 7 was performed using 3-trifluoromethyl-benzenesulfonyl chloride and yielded 2-fluoro-4-{[4-(3-trifluoromethyl-benzenesulfonyl)-3,4-dihydro-2H-benzo[1,4]oxazine-6-carbonyl]-amino}-benzoic acid ethyl ester, which was hydrolyzed in step 8.

Example 22

4-{[4-(3-Chloro-benzenesulfonyl)-3,4-dihydro-2H-benzo[1,4]oxazine-6-carbonyl]-amino}-2-fluoro-benzoic acid 4-{[4-(3-Chloro-benzenesulfonyl)-3,4-dihydro-2H-benzo[1,4]oxazine-6-carbonyl]-amino}-2-fluoro-benzoic acid, MS (ISP): m/e=489.1 (M−H), was prepared as described for example 21, steps 1 to 8. Step 7 was performed using 3-chloro-benzenesulfonyl chloride and yielded 4-{[4-(3-chloro-benzenesulfonyl)-3,4-dihydro-2H-benzo[1,4]oxazine-6-carbonyl]-amino}-2-fluoro-benzoic acid ethyl ester, which was hydrolyzed in step 8.

Example 23

2-Fluoro-4-{[4-(3-fluoro-benzenesulfonyl)-3,4-dihydro-2H-benzo[1,4]oxazine-6-carbonyl]-amino}-benzoic acid 2-Fluoro-4-{[4-(3-fluoro-benzenesulfonyl)-3,4-dihydro-2H-benzo[1,4]oxazine-6-carbonyl]-amino}-benzoic acid, MS (ISP): m/e=473.1 (M−H), was prepared as described for example 21, steps 1 to 8. Step 7 was performed using 3-fluoro-benzenesulfonyl chloride and yielded 2-fluoro-4-{[4-(3-fluoro-benzenesulfonyl)-3,4-dihydro-2H-benzo[1,4]oxazine-6-carbonyl]-amino}-benzoic acid ethyl ester, which was hydrolyzed in step 8.

Example 24

4-{[4-(2,5-Difluoro-benzenesulfonyl)-3,4-dihydro-2H-benzo[1,4]oxazine-6-carbonyl]-amino}-2-fluoro-benzoic acid 4-{[4-(2,5-Difluoro-benzenesulfonyl)-3,4-dihydro-2H-benzo[1,4]oxazine-6-carbonyl]-amino}-2-fluoro-benzoic acid, MS (ISP): m/e=491.1 (M−H), was prepared as described for example 21, steps 1 to 8. Step 7 was performed using 2,5-difluoro-benzenesulfonyl chloride and yielded 4-{[4-(2,5-difluoro-benzenesulfonyl)-3,4-dihydro-2H-benzo[1,4]oxazine-6-carbonyl]-amino}-2-fluoro-benzoic acid ethyl ester, which was hydrolyzed in step 8.

Example 25

2-Fluoro-4-{[4-(5-fluoro-2-methyl-benzenesulfonyl)-3,4-dihydro-2H-benzo[1,4]oxazine-6-carbonyl]-amino}-benzoic acid 2-Fluoro-4-{[4-(5-fluoro-2-methyl-benzenesulfonyl)-3,4-dihydro-2H-benzo[1,4]oxazine-6-carbonyl]-amino}-benzoic acid, MS (ISP): m/e=487.1 (M−H), was prepared as described for example 21, steps 1 to 8. Step 7 was performed using 5-fluoro-2-methyl-benzenesulfonyl chloride and yielded 2-fluoro-4-{[4-(5-fluoro-2-methyl-benzenesulfonyl)-3,4-dihydro-2H-benzo[1,4]oxazine-6-carbonyl]-amino}-benzoic acid ethyl ester, which was hydrolyzed in step 8.

Example 26

4-{[4-(3-Difluoromethoxy-benzenesulfonyl)-3,4-dihydro-2H-benzo[1,4]oxazine-6-carbonyl]-amino}-2-fluoro-benzoic acid 4-{[4-(3-Difluoromethoxy-benzenesulfonyl)-3,4-dihydro-2H-benzo[1,4]oxazine-6-carbonyl]-amino}-2-fluoro-benzoic acid, MS (ISP): m/e=521.2 (M−H), was prepared as described for example 21, steps 1 to 8. Step 7 was performed using 3-difluoromethoxy-benzenesulfonyl chloride and yielded 4-{[4-(3-difluoromethoxy-benzenesulfonyl)-3,4-dihydro-2H-benzo[1,4]oxazine-6-carbonyl]-amino}-2-fluoro-benzoic acid ethyl ester, which was hydrolyzed in step 8.

Example 27

4-{[4-(3,5-Dimethyl-benzenesulfonyl)-3,4-dihydro-2H-benzo[1,4]oxazine-6-carbonyl]-amino}-2-fluoro-benzoic acid 4-{[4-(3,5-Dimethyl-benzenesulfonyl)-3,4-dihydro-2H-benzo[1,4]oxazine-6-carbonyl]-amino}-2-fluoro-benzoic acid, MS (ISP): m/e=483.3 (M−H), was prepared as described for example 21, steps 1 to 8. Step 7 was performed using 3,5-dimethyl-benzenesulfonyl chloride and yielded 4-{[4-(3,5-dimethyl-benzenesulfonyl)-3,4-dihydro-2H-benzo[1,4]oxazine-6-carbonyl]-amino}-2-fluoro-benzoic acid ethyl ester, which was hydrolyzed in step 8.

Example 28

4-{[4-(3-Carbamoyl-benzenesulfonyl)-3,4-dihydro-2H-benzo[1,4]oxazine-6-carbonyl]-amino}-2-fluoro-benzoic acid 4-{[4-(3-Carbamoyl-benzenesulfonyl)-3,4-dihydro-2H-benzo[1,4]oxazine-6-carbonyl]-amino}-2-fluoro-benzoic acid, MS (ISP): m/e=500.0 (M+H$^{+\cdot}$), was prepared as described for example 21, steps 1 to 8. Step 7 was performed using 3-cyano-benzenesulfonyl chloride and yielded 4-{[4-(3-cyano-benzenesulfonyl)-3,4-dihydro-2H-benzo[1,4]oxazine-6-carbonyl]-amino}-2-fluoro-benzoic acid ethyl ester, which was hydrolyzed in step 8 at both the carboxylic acid ester and the cyano position.

Example 29

6-{[4-(5-Chloro-2-methoxy-benzenesulfonyl)-3,4-dihydro-2H-benzo[1,4]oxazine-6-carbonyl]-amino}-nicotinic acid 6-{[4-(5-Chloro-2-methoxy-benzenesulfonyl)-3,4-dihydro-2H-benzo[1,4]oxazine-6-carbonyl]-amino}-nicotinic acid, MS (ISP): m/e=502.1 (M−H), was prepared as described for example 14, steps 1 to 8. Step 4 was performed using 6-amino-nicotinic acid methyl ester, yielding 6-(4-benzyloxy-3-nitro-benzoylamino)-nicotinic acid methyl ester, which was reduced to 6-(3-amino-4-hydroxy-benzoylamino)-nicotinic acid methyl ester in step 5 and cyclized to 6-[(3,4-dihydro-2H-benzo[1,4]oxazine-6-carbonyl)-amino]-nicotinic acid methyl ester in step 6. Step 7 was performed using 5-chloro-2-methoxy-benzenesulfonyl chloride and yielded 6-{[4-(5-chloro-2-methoxy-benzenesulfonyl)-3,4-dihydro-2H-benzo[1,4]oxazine-6-carbonyl]-amino}-nicotinic acid methyl ester, which was hydrolyzed in step 8.

Example 30

2-Chloro-4-{[3-(5-chloro-2-methoxy-benzenesulfonyl)-2,3-dihydro-benzooxazole-5-carbonyl]-amino}-benzoic acid The title compound was prepared as illustrated in schemes 1 and 6.

Step 1. 5-Chloro-2-methoxybenzenesulfonyl chloride (5.77 g, 2.39 mmol) was added to a solution of 3-amino-4-hydroxy-benzoic acid methyl ester (example 1, step 1; 4.00 g, 23.9 mmol) in pyridine (38 mL). The homogeneous solution was stirred at room temperature for 72 h, then partitioned between ethyl acetate and 2 M aq. hydrochloric acid solution. The organic layer was washed with brine, dried (MgSO$_4$), and evaporated. The residue was triturated in ethyl acetate to furnish 3-(5-chloro-2-methoxy-benzenesulfonylamino)-4-hydroxy-benzoic acid methyl ester (7.19 g, 81%). Pink solid, MS (ISP)=370.0 (M−H)$^-$.

Step 2. Potassium carbonate (3.87 g, 28.0 mmol) was added to a solution of 3-(5-chloro-2-methoxy-benzenesulfonylamino)-4-hydroxy-benzoic acid methyl ester (2.08 g, 5.59 mmol) and dibromomethane (2.92 g, 16.5 mmol) in N,N-dimethylformamide (35 mL), and the suspension was heated at 80° C. for 48 h, then the reaction mixture was partitioned between water and dichloromethane. The organic layer was washed with brine, dried (MgSO$_4$), and evaporated. Chromatography (SiO$_2$, heptane-ethyl acetate gradient) produced 3-(5-chloro-2-methoxybenzenesulfonyl)-2,3-dihydro-benzooxazole-5-carboxylic acid methyl ester (2.13 g, 99%). White solid, MS (ISP)=384.1 (M+H)$^+$.

Step 3. Hydrolysis of 3-(5-chloro-2-methoxy-benzenesulfonyl)-2,3-dihydro-benzooxazole-5-carboxylic acid methyl ester in accordance with the general method of example 1, step 4 produced 3-(5-chloro-2-methoxy-benzenesulfonyl)-2,3-dihydro-benzooxazole-5-carboxylic acid. Light red solid, MS (ISP)=368.1 (M−H)$^-$.

Step 4. A solution of 3-(5-chloro-2-methoxy-benzenesulfonyl)-2,3-dihydro-benzooxazole-5-carboxylic acid (1.00 g, 2.70 mmol), ethyl 4-amino-2-chlorobenzoate (1.08 g, 5.41 mmol), 4-methylmorpholine (1.37 g, 13.5 mmol), and O-(7-azabenzotriazol-1-yl)-N,N,N',N'-tetramethyluronium hexafluoro-phosphate (1.54 g, 4.06 mmol) in N,N-dimethylformamide (10 mL) was stirred at room temperature for 15 min, then 4-(dimethylamino)pyridine (337 mg, 2.70 mmol) were added, and the solution was stirred at 60° C. for 18 h. After cooling, the reaction mixture was partitioned between water, heptane, and ethyl acetate. The organic layer was washed with brine, dried (MgSO$_4$), and evaporated. Chromatography (SiO$_2$, heptane-ethyl acetate gradient) produced 2-chloro-4-{[3-(5-chloro-2-methoxy-benzenesulfonyl)-2,3-dihydro-benzooxazole-5-carbonyl]-amino}-benzoic acid ethyl ester (849 mg, 57%). Off-white solid, MS (ISP)=551.2 (M+H)$^+$.

Step 5. Hydrolysis of 2-chloro-4-{[3-(5-chloro-2-methoxy-benzenesulfonyl)-2,3-dihydro-benzooxazole-5-carbonyl]-amino}-benzoic acid ethyl ester, in accordance with the general method of example 1, step 6 produced the title compound. White solid, MS (ISP)=521.1 (M−H)$^−$.

Example 31

4-{[3-(5-Chloro-2-methoxy-benzenesulfonyl)-2,3-dihydro-benzooxazole-5-carbonyl]-amino}-benzoic acid The title compound, MS (ISP)=487.1 (M−H)$^−$, was produced as described in example 30, steps 1 to 5. Step 4 was performed using 4-aminobenzoic acid ethyl ester and yielded 4-{[3-(5-chloro-2-methoxy-benzenesulfonyl)-2,3-dihydro-benzooxazole-5-carbonyl]-amino}-benzoic acid ethyl ester, which was hydrolyzed in step 5.

Example 32

4-{[3-(5-Chloro-2-methoxy-benzenesulfonyl)-2,3-dihydro-benzooxazole-5-carbonyl]-amino}-2-fluoro-benzoic acid The title compound, MS (ISP)=507.2 (M+H)$^+$, was produced as described in example 30, steps 1 to 5. Step 4 was performed using 4-amino-2-fluoro-benzoic acid ethyl ester and yielded 4-{[3-(5-chloro-2-methoxy-benzenesulfonyl)-2,3-dihydro-benzooxazole-5-carbonyl]-amino}-2-fluoro-benzoic acid ethyl ester, which was hydrolyzed in step 5.

Example 33

3-(5-Chloro-2-methoxy-benzenesulfonyl)-2,3-dihydro-benzooxazole-5-carboxylic acid phenylamide The title compound, MS (ISP)=445.2 (M+H)$^+$, was produced as described in example 30, steps 1 to 4. Step 4 was performed using aniline as amine reagent.

Example 34

3-(5-Chloro-2-methoxy-benzenesulfonyl)-2,3-dihydro-benzooxazole-5-carboxylic acid pyridin-3-ylamide The title compound, MS (ISP)=446.1 (M+H)$^+$, was produced as described in example 30, steps 1 to 4. Step 4 was performed using 3-aminopyridine as amine reagent.

Example 35

4-{[3-(5-Chloro-2-methoxy-benzenesulfonyl)-2-phenyl-2,3-dihydro-benzooxazole-5-carbonyl]-amino}-benzoic acid The title compound was prepared as illustrated in schemes 1 and 6.

Step 1. A mixture of 3-(5-chloro-2-methoxy-benzenesulfonylamino)-4-hydroxy-benzoic acid methyl ester (example 30, step 1; 200 mg, 0.537 mmol), benzaldehyde dimethyl acetal (0.5 mL) and toluene-4 sulfonic acid monohydrate (10 mg, 54 mmol) was stirred at 100° C. for 48 h. After cooling, heptane was added, and the precipitate was collected by filtration to afford 3-(5-chloro-2-methoxy-benzenesulfonyl)-2-phenyl-2,3-dihydro-benzooxazole-5-carboxylic acid methyl ester (208 mg, 84%). Light yellow solid, MS (ISP)=460.2 (M+H)$^+$.

Step 2. Hydrolysis of 3-(5-chloro-2-methoxy-benzenesulfonyl)-2-phenyl-2,3-dihydro-benzooxazole-5-carboxylic acid methyl ester in accordance with the general method of example 1, step 4 produced 3-(5-chloro-2-methoxy-benzenesulfonyl)-2-phenyl-2,3-dihydro-benzooxazole-5-carboxylic acid. White solid, MS (ISP)=443.9 (M−H)$^−$.

Step 3. Reaction of 3-(5-chloro-2-methoxy-benzenesulfonyl)-2-phenyl-2,3-dihydro-benzooxazole-5-carboxylic acid with 4-aminobenzoic acid ethyl ester in accordance with the general method of example 30, step 4 produced 4-{[3-(5-chloro-2-methoxy-benzenesulfonyl)-2-phenyl-2,3-dihydro-benzooxazole-5-carbonyl]-amino}-benzoic acid ethyl ester. Off-white solid, MS (ISP)=593.2 (M+H)$^+$.

Step 4. Hydrolysis of 4-{[3-(5-chloro-2-methoxy-benzenesulfonyl)-2-phenyl-2,3-dihydro-benzooxazole-5-carbonyl]-amino}-benzoic acid ethyl ester, in accordance with the general method of example 1, step 6 produced the title compound. White solid, MS (ISP)=563.2 (M−H)$^−$.

Example 36

4-{[9-(5-Chloro-2-methoxy-benzenesulfonyl)-6,7,8,9-tetrahydro-5-oxa-9-aza-benzocycloheptene-2-carbonyl]-amino}-benzoic acid The title compound was prepared as illustrated in schemes 1 and 4.

Step 1. Potassium carbonate (818 mg, 5.92 mmol) was added to a solution of 3-(5-chloro-2-methoxy-benzenesulfonylamino)-4-hydroxy-benzoic acid methyl ester (example 30, step 1; 1.00 g, 2.69 mmol) and 1,3-dibromopropane (597 mg, 2.96 mmol) in N,N-dimethylformamide (17 mL), and the suspension was heated at 60° C. for 5 h, then the reaction mixture was partitioned between water and ethyl acetate. The organic layer was washed with brine, dried (MgSO$_4$), and evaporated. Chromatography (SiO$_2$, heptane-ethyl acetate gradient) produced 9-(5-chloro-2-methoxybenzenesulfonyl)-6,7,8,9-tetrahydro-5-oxa-9-aza-benzocycloheptene-2-carboxylic acid methyl ester (996 mg, 90%). White solid, MS (ISP)=412.1 (M+H)$^+$.

Step 2. Hydrolysis of 9-(5-chloro-2-methoxy-benzenesulfonyl)-6,7,8,9-tetrahydro-5-oxa-9-aza-benzocycloheptene-2-carboxylic acid methyl ester in accordance with the general method of example 1, step 4 produced 9-(5-chloro-2-methoxy-benzenesulfonyl)-6,7,8,9-tetrahydro-5-oxa-9-aza-benzocycloheptene-2-carboxylic acid. White solid, MS (ISP)=396.1 (M−H)$^−$.

Step 3. Reaction of 9-(5-chloro-2-methoxy-benzenesulfonyl)-6,7,8,9-tetrahydro-5-oxa-9-aza-benzocycloheptene-2- carboxylic acid with 4-aminobenzoic acid ethyl ester in accordance with the general method of example 30, step 4 produced 4-{[9-(5-chloro-2-methoxy-benzenesulfonyl)-6,7,8,9-tetrahydro-5-oxa-9-aza-benzocycloheptene-2-carbonyl]-amino}-benzoic acid ethyl ester. White solid, MS (ISP)= 545.3 (M+H)$^+$.

Step 4. Hydrolysis of 4-{[9-(5-chloro-2-methoxy-benzenesulfonyl)-6,7,8,9-tetrahydro-5-oxa-9-aza-benzocycloheptene-2-carbonyl]-amino}-benzoic acid ethyl ester in accordance with the general method of example 1, step 6 produced the title compound. White solid, MS (ISP)=515.2 (M−H)$^-$.

Example 37

2-Chloro-4-{[9-(5-chloro-2-methoxy-benzenesulfonyl)-6,7,8,9-tetrahydro-5-oxa-9-aza-benzocycloheptene-2-carbonyl]-amino}-benzoic acid The title compound, MS (ISP)=548.9 (M−H)$^-$, was produced as described in example 36, steps 1 to 4. Step 3 was performed using ethyl 4-amino-2-chlorobenzoate and yielded 2-chloro-4-{[9-(5-chloro-2-methoxy-benzenesulfonyl)-6,7,8,9-tetrahydro-5-oxa-9-aza-benzocycloheptene-2-carbonyl]-amino}-benzoic acid ethyl ester, which was hydrolyzed in step 4.

Example 38

4-{[6-(5-Chloro-2-methoxy-benzenesulfonyl)-3,4,5,6-tetrahydro-2H-benzo[b][1,4]oxazocine-8-carbonyl]-amino}-benzoic acid The title compound, MS (ISP)=529.0 (M−H)$^-$, was produced in analogy with example 36, steps 1 to 4. Step 1 was performed using 1,4-dibromobutane, yielding 6-(5-chloro-2-methoxybenzenesulfonyl)-3,4,5,6-tetrahydro-2H-benzo[b][1,4]oxazocine-8-carboxylic acid methyl ester, which was hydrolyzed in step 2 to afford 6-(5-chloro-2-methoxy-benzenesulfonyl)-3,4,5,6-tetrahydro-2H-benzo[b][1,4]oxazocine-8-carboxylic acid. This was reacted with ethyl 4-aminobenzoate in step 3 to produce 4-{[6-(5-chloro-2-methoxy-benzenesulfonyl)-3,4,5,6-tetrahydro-2H-benzo[b][1,4]oxazocine-8-carbonyl]-amino}-benzoic acid ethyl ester, which was hydrolyzed in step 4.

Example 39

2-Chloro-4-{[6-(5-chloro-2-methoxy-benzenesulfonyl)-3,4,5,6-tetrahydro-2H-benzo[b][1,4]oxazocine-8-carbonyl]-amino}-benzoic acid The title compound, MS (ISP)=565.2 (M+H)$^+$, was produced as described in example 38, steps 1 to 4. Step 3 was performed using ethyl 4-amino-2-chloro-benzoate and yielded 2-chloro-4-{[6-(5-chloro-2-methoxy-benzenesulfonyl)-3,4,5,6-tetrahydro-2H-benzo[b][1,4]oxazocine-8-carbonyl]-amino}-benzoic acid ethyl ester, which was hydrolyzed in step 4.

Example 40

4-{[3-(5-Chloro-2-methoxy-benzenesulfonyl)-7-trifluoromethyl-2,3-dihydro-benzooxazole-5-carbonyl]-amino}-benzoic acid The title compound was prepared as illustrated in schemes 1 and 6.

Step 1. 4-Hydroxy-3-nitro-5-trifluoromethyl-benzoic acid methyl ester was hydrogenated in analogy with example 1, step 1 to produce 3-amino-4-hydroxy-5-trifluoromethyl-benzoic acid methyl ester. Yellow solid, MS (ISP)=234.1 (M−H)$^-$.

Step 2. A suspension of 3-amino-4-hydroxy-5-trifluoromethyl-benzoic acid methyl ester (4.66 g, 19.8 mmol) and 5-chloro-2-methoxybenzenesulfonyl chloride (4.78 g, 19.8 mmol) in toluene (38 mL) was heated at reflux for 48 h. After cooling, the precipitate was collected by filtration and washed with toluene to afford 3-(5-chloro-2-methoxy-benzenesulfonylamino)-4-hydroxy-5-trifluoromethyl-benzoic acid methyl ester. Off-white solid, MS (ISP)=438.0 (M−H)$^-$.

Step 3. Cyclization of 3-(5-chloro-2-methoxy-benzenesulfonylamino)-4-hydroxy-5-trifluoromethyl-benzoic acid methyl ester with dibromomethane in accordance with example 30, step 2 furnished 3-(5-chloro-2-methoxy-benzenesulfonyl)-7-trifluoromethyl-2,3-dihydro-benzooxazole-5-carboxylic acid methyl ester. White foam, MS (ISP)=451.9 (M+H)$^+$.

Step 4. Hydrolysis of 3-(5-chloro-2-methoxy-benzenesulfonyl)-7-trifluoromethyl-2,3-dihydro-benzooxazole-5-carboxylic acid methyl ester in analogy with example 1, step 4 produced 3-(5-chloro-2-methoxy-benzenesulfonyl)-7-trifluoromethyl-2,3-dihydro-benzooxazole-5-carboxylic acid. White solid, MS (ISP)=436.0 (M−H)$^-$.

Step 5. Reaction of 3-(5-chloro-2-methoxy-benzenesulfonyl)-7-trifluoromethyl-2,3-dihydro-benzooxazole-5-carboxylic acid with ethyl 4-aminobenzoate in analogy with example 30, step 4 gave 4-{[3-(5-chloro-2-methoxy-benzenesulfonyl)-7-trifluoromethyl-2,3-dihydro-benzooxazole-5-carbonyl]-amino}-benzoic acid ethyl ester. Light yellow solid, MS (ISP)=584.9 (M+H)$^+$.

Step 6. Hydrolysis of 4-{[3-(5-chloro-2-methoxy-benzenesulfonyl)-7-trifluoromethyl-2,3-dihydro-benzooxazole-5-carbonyl]-amino}-benzoic acid ethyl ester in analogy with example 1, step 6 afforded the title compound. White solid, MS (ISP)=554.9 (M−H)$^-$.

Preparation of the Starting Material:

A solution of 3-trifluoromethyl-4-hydroxybenzoic acid (5.00 g, 24.3 mmol) in 15% methanolic sulfuric acid solution (50 mL) was heated at reflux over 48 h, then poured upon ice and extracted with ethyl acetate. The organic layer was washed with 1 M aq. sodium carbonate solution and brine, dried (MgSO$_4$), and evaporated to afford 4-hydroxy-3-trifluoromethyl-benzoic acid methyl ester (4.67 g, 87%). Off-white solid, MS (ISP)=219.0 (M−H)$^-$.

65% aq. nitric acid solution (1.76 mL, 39 mmol) and fuming nitric acid (3.25 mL, 78 mmol) were added at −10° C. to a solution of 4-hydroxy-3-trifluoromethyl-benzoic acid methyl ester (4.31 g, 19.6 mmol) in acetic acid (54 mL). The ice bath was removed and the solution was stirred at room temperature for 5 h, then partitioned between water and ethyl acetate. The organic layer was washed with brine, dried (MgSO$_4$), and evaporated to afford 4-hydroxy-3-nitro-5-trifluoromethyl-benzoic acid methyl ester (5.16 g, 99%). Orange solid, MS (ISP)=263.9 (M−H)$^-$.

Example 41

4-{[4-(5-Chloro-2-methoxy-benzenesulfonyl)-8-trifluoromethyl-3,4-dihydro-2H-benzo[1,4]oxazine-6-carbonyl]-amino}-benzoic acid The title compound, MS (ISP)=569.0 (M–H)⁻, was produced in analogy with example 36, steps 1-4. Step 1 was performed using 3-(5-chloro-2-methoxy-benzenesulfonylamino)-4-hydroxy-5-trifluoromethyl-benzoic acid methyl ester (example 40, step 2) and 1,2-dibromoethane, yielding 4-(5-chloro-2-methoxy-benzenesulfonyl)-8-trifluoromethyl-3,4-dihydro-2H-benzo[1,4]oxazine-6-carboxylic acid methyl ester, which was hydrolyzed in step 2 to afford 4-(5-chloro-2-methoxybenzenesulfonyl)-8-trifluoromethyl-3,4-dihydro-2H-benzo[1,4]oxazine-6-carboxylic acid. This was reacted with ethyl 4-aminobenzoate in step 3 to produce 4-{[4-(5-chloro-2-methoxybenzenesulfonyl)-8-trifluoromethyl-3,4-dihydro-2H-benzo[1,4]oxazine-6-carbonyl]-amino}-benzoic acid ethyl ester, which was hydrolyzed in step 4.

Example 42

4-{[3-(5-Chloro-2-methoxy-benzenesulfonyl)-7-methoxy-2,3-dihydro-benzooxazole-5-carbonyl]-amino}-benzoic acid The title compound was prepared as illustrated in schemes 1 and 6.

Step 1. 3-Methoxy-4-hydroxy-5-nitro-benzoic acid methyl ester (*J. Am. Chem. Soc.* 1983, 105, 5015) was hydrogenated in analogy with example 1, step 1 to produce 3-amino-4-hydroxy-5-methoxy-benzoic acid methyl ester. Dark green solid, MS (ISP)=198.3 (M+H)⁺.

Step 2. 3-Amino-4-hydroxy-5-methoxy-benzoic acid methyl ester was reacted with 5-chloro-2-methoxybenzenesulfonyl chloride in accordance with the general method of example 40, step 2 and led to 3-(5-chloro-2-methoxy-benzenesulfonylamino)-4-hydroxy-5-methoxy-benzoic acid methyl ester. Light grey solid, MS (ISP)=400.1 (M–H)⁻.

Step 3. Cyclization of 3-(5-chloro-2-methoxy-benzenesulfonylamino)-4-hydroxy-5-methoxy-benzoic acid methyl ester with dibromomethane in accordance with example 30, step 2 furnished 3-(5-chloro-2-methoxy-benzenesulfonyl)-7-methoxy-2,3-dihydro-benzooxazole-5-carboxylic acid methyl ester. White solid, MS (ISP)=414.2 (M+H)⁺.

Step 4. Hydrolysis of 3-(5-chloro-2-methoxy-benzenesulfonyl)-7-methoxy-2,3-dihydro-benzooxazole-5-carboxylic acid methyl ester in analogy with example 1, step 4 produced 3-(5-chloro-2-methoxy-benzenesulfonyl)-7-methoxy-2,3-dihydro-benzooxazole-5-carboxylic acid. White solid, MS (ISP)=398.0 (M–H)⁻.

Step 5. Reaction of 3-(5-chloro-2-methoxy-benzenesulfonyl)-7-methoxy-2,3-dihydro-benzooxazole-5-carboxylic acid with ethyl 4-aminobenzoate in analogy with example 30, step 4 gave 4-{[3-(5-chloro-2-methoxy-benzenesulfonyl)-7-methoxy-2,3-dihydro-benzooxazole-5-carbonyl]-amino}-benzoic acid ethyl ester. White solid, MS (ISP)=547.2 (M+H)⁺.

Step 6. Hydrolysis of 4-{[3-(5-chloro-2-methoxy-benzenesulfonyl)-7-methoxy-2,3-dihydro-benzooxazole-5-carbonyl]-amino}-benzoic acid ethyl ester in analogy with example 1, step 6 afforded the title compound. White solid, MS (ISP)=517.1 (M–H)⁻.

Example 43

4-{[4-(5-Chloro-2-methoxy-benzenesulfonyl)-8-methoxy-3,4-dihydro-2H-benzo[1,4]oxazine-6-carbonyl]-amino}-benzoic acid The title compound, MS (ISP)=531.1 (M–H)⁻, was produced in analogy with example 36, steps 1-4. Step 1 was performed using 3-(5-chloro-2-methoxy-benzenesulfonylamino)-4-hydroxy-5-methoxy-benzoic acid methyl ester (example 42, step 2) and 1,2-dibromoethane, yielding 4-(5-chloro-2-methoxy-benzenesulfonyl)-8-methoxy-3,4-dihydro-2H-benzo[1,4]oxazine-6-carboxylic acid methyl ester, which was hydrolyzed in step 2 to afford 4-(5-chloro-2-methoxy-benzenesulfonyl)-8-methoxy-3,4-dihydro-2H-benzo[1,4]oxazine-6-carboxylic acid. This was reacted with ethyl 4-aminobenzoate in step 3 to produce 4-{[4-(5-chloro-2-methoxy-benzenesulfonyl)-8-methoxy-3,4-dihydro-2H-benzo[1,4]oxazine-6-carbonyl]-amino}-benzoic acid ethyl ester, which was hydrolyzed in step 4.

Example 44

4-{[3-(5-Chloro-2-methoxy-benzenesulfonyl)-7-fluoro-2,3-dihydro-benzooxazole-5-carbonyl]-amino}-benzoic acid The title compound was prepared as illustrated in schemes 1 and 6.

Step 1. 3-Fluoro-4-hydroxy-5-nitro-benzoic acid methyl ester was hydrogenated in analogy with example 1, step 1 to produce 3-amino-5-fluoro-4-hydroxy-benzoic acid methyl ester. Light yellow solid, MS (ISP)=184.1 (M–H)⁻.

Step 2. 3-Amino-5-fluoro-4-hydroxy-benzoic acid methyl ester was reacted with 5-chloro-2-methoxybenzenesulfonyl chloride in accordance with the general method of example 40, step 2 and led to 3-(5-chloro-2-methoxy-benzenesulfonylamino)-5-fluoro-4-hydroxy-benzoic acid methyl ester. White solid, MS (ISP)=388.2 (M–H)⁻.

Step 3. Cyclization of 3-(5-chloro-2-methoxy-benzenesulfonylamino)-5-fluoro-4-hydroxy-benzoic acid methyl ester with dibromomethane in accordance with example 30, step 2 furnished 3-(5-chloro-2-methoxy-benzenesulfonyl)-7-fluoro-2,3-dihydro-benzooxazole-5-carboxylic acid methyl ester. White solid, MS (ISP)=402.0 (M+H)⁺.

Step 4. Hydrolysis of 3-(5-chloro-2-methoxy-benzenesulfonyl)-7-fluoro-2,3-dihydrobenzooxazole-5-carboxylic acid methyl ester in analogy with example 1, step 4 produced 3-(5-chloro-2-methoxy-benzenesulfonyl)-7-fluoro-2,3-dihydro-benzooxazole-5-carboxylic acid. White solid, MS (ISP)=386.0 (M–H)⁻.

Step 5. Reaction of 3-(5-chloro-2-methoxy-benzenesulfonyl)-7-fluoro-2,3-dihydrobenzooxazole-5-carboxylic acid with ethyl 4-aminobenzoate in analogy with example 30, step 4 gave 4-{[3-(5-chloro-2-methoxy-benzenesulfonyl)-7-fluoro-2,3-dihydro-benzooxazole-5-carbonyl]-amino}-benzoic acid ethyl ester. White solid, MS (ISP)=535.2 (M+H)⁺.

Step 6. Hydrolysis of 4-{[3-(5-chloro-2-methoxy-benzenesulfonyl)-7-fluoro-2,3-dihydrobenzooxazole-5-carbonyl]-amino}-benzoic acid ethyl ester in analogy with example 1, step 6 afforded the title compound. White solid, MS (ISP)=505.1 (M–H)⁻.

Preparation of the Starting Material:

A solution of 3-fluoro-4-hydroxybenzoic acid (5.00 g, 32.0 mmol) in 15% methanolic sulfuric acid solution (50 mL) was heated at reflux over 48 h, then poured upon ice and extracted with ethyl acetate. The organic layer was washed with 1 M aq.

sodium carbonate solution and brine, dried (MgSO$_4$), and evaporated to afford 4-fluoro-3-trifluoromethyl-benzoic acid methyl ester (4.48 g, 82%). Off-white solid, MS (ISP)=169.1 (M−H)⁻.

65% aq. nitric acid solution (2.3 mL, 50 mmol) and fuming nitric acid (2.1 mL, 50 mmol) were added at −10° C. to a solution of 4-hydroxy-3-trifluoromethyl-benzoic acid methyl ester (4.27 g, 25.1 mmol) in diethyl ether (60 mL). The ice bath was removed and the reaction mixture was stirred at room temperature for 16 h, then partitioned between water and ethyl acetate. The organic layer was washed with brine, dried (MgSO$_4$), and evaporated to afford 3-fluoro-4-hydroxy-5-nitro-benzoic acid methyl ester (5.39 g, 100%). Yellow solid, MS (ISP)=214.1 (M−H)⁻.

Example 45

2-Chloro-4-{[3-(5-chloro-2-methoxy-benzenesulfonyl)-7-fluoro-2,3-dihydro-benzooxazole-5-carbonyl]-amino}-benzoic acid The title compound, MS (ISP)=539.1 (M−H)⁻, was produced as described in example 44, steps 1-5. Step 4 was performed using ethyl 4-amino-2-chlorobenzoate and yielded 2-chloro-4-{[3-(5-chloro-2-methoxy-benzenesulfonyl)-7-fluoro-2,3-dihydro-benzooxazole-5-carbonyl]-amino}-benzoic acid ethyl ester, which was hydrolyzed in step 5.

Example 46

4-{[3-(5-Chloro-2-methoxy-benzenesulfonyl)-7-fluoro-2,3-dihydro-benzooxazole-5-carbonyl]-amino}-2-fluoro-benzoic acid The title compound, MS (ISP)=523.2 (M−H)⁻, was produced as described in example 44, steps 1-5. Step 4 was performed using ethyl 4-amino-2-fluorobenzoate and yielded 4-{[3-(5-chloro-2-methoxy-benzenesulfonyl)-7-fluoro-2,3-dihydro-benzooxazole-5-carbonyl]-amino}-2-fluoro-benzoic acid ethyl ester, which was hydrolyzed in step 5.

Example 47

4-{[4-(5-Chloro-2-methoxy-benzenesulfonyl)-8-fluoro-3,4-dihydro-2H-benzo[1,4]oxazine-6-carbonyl]-amino}-benzoic acid The title compound, MS (ISP)=519.1 (M−H)⁻, was produced in analogy with example 36, steps 1-4. Step 1 was performed using 3-(5-chloro-2-methoxy-benzenesulfonylamino)-5-fluoro-4-hydroxy-benzoic acid methyl ester (example 44, step 2) and 1,2-dibromoethane, yielding 4-(5-chloro-2-methoxy-benzenesulfonyl)-8-fluoro-3,4-dihydro-2H-benzo[1,4]oxazine-6-carboxylic acid methyl ester, which was hydrolyzed in step 2 to afford 4-(5-chloro-2-methoxy-benzenesulfonyl)-8-fluoro-3,4-dihydro-2H-benzo[1,4]oxazine-6-carboxylic acid. This was reacted with ethyl 4-aminobenzoate in step 3 to produce 4-{[4-(5-chloro-2-methoxy-benzenesulfonyl)-8-fluoro-3,4-dihydro-2H-benzo[1,4]oxazine-6-carbonyl]-amino}-benzoic acid ethyl ester, which was hydrolyzed in step 4.

Example 48

2-Chloro-4-{[4-(5-chloro-2-methoxy-benzenesulfonyl)-8-fluoro-3,4-dihydro-2H-benzo[1,4]oxazine-6-carbonyl]-amino}-benzoic acid The title compound, MS (ISP)=552.9 (M−H)⁻, was produced as described in example 47, steps 1-4. Step 3 was performed using ethyl 4-amino-2-chlorobenzoate and yielded 2-chloro-4-{[4-(5-chloro-2-methoxy-benzenesulfonyl)-8-fluoro-3,4-dihydro-2H-benzo[1,4]oxazine-6-carbonyl]-amino}-benzoic acid ethyl ester, which was hydrolyzed in step 4.

Example 49

4-{[4-(5-Chloro-2-methoxy-benzenesulfonyl)-8-fluoro-3,4-dihydro-2H-benzo[1,4]oxazine-6-carbonyl]-amino}-2-fluoro-benzoic acid The title compound, MS (ISP)=536.8 (M−H)⁻, was produced as described in example 47, steps 1-4. Step 3 was performed using ethyl 4-amino-2-fluorobenzoate and yielded 4-{[4-(5-chloro-2-methoxy-benzenesulfonyl)-8-fluoro-3,4-dihydro-2H-benzo[1,4]oxazine-6-carbonyl]-amino}-2-fluoro-benzoic acid ethyl ester, which was hydrolyzed in step 4.

Example 50

4-{[7-Chloro-3-(5-chloro-2-methoxy-benzenesulfonyl)-2,3-dihydro-benzooxazole-5-carbonyl]-amino}-benzoic acid The title compound was prepared as illustrated in schemes 1 and 6.

Step 1. A solution of 3-chloro-4-hydroxy-5-nitro-benzoic acid methyl ester (500 mg, 2.16 mmol) in methanol (22 mL) was added within 10 min to a mixture of iron powder (410 mg, 7.34 mmol) ammonium chloride (647 mg, 12.1 mmol) in water (22 mL). The reaction mixture was heated at reflux over 16 h, then after cooling filtered through a pad of diatomaceous earth. The filtrate was extracted with ethyl acetate, dried (MgSO$_4$), and evaporated. Chromatography (SiO$_2$, ethyl acetate/heptane 7:3) afforded 3-amino-5-chloro-4-hydroxy-benzoic acid methyl ester (293 mg, 68%). Light yellow solid, MS (ISP)=200.1 (M−H)⁻.

Step 2. 3-Amino-5-chloro-4-hydroxy-benzoic acid methyl ester was reacted with 5-chloro-2-methoxybenzenesulfonyl chloride in accordance with the general method of example 40, step 2 and led to 3-chloro-5-(5-chloro-2-methoxy-benzenesulfonylamino)-4-hydroxy-benzoic acid methyl ester. White solid, MS (ISP)=404.2 (M−H)⁻.

Step 3. 3-Chloro-5-(5-chloro-2-methoxy-benzenesulfonylamino)-4-hydroxy-benzoic acid methyl ester with dibromomethane in accordance with example 30, step 2 furnished 7-chloro-3-(5-chloro-2-methoxy-benzenesulfonyl)-2,3-dihydro-benzooxazole-5-carboxylic acid methyl ester. White solid, MS (ISP)=418.0 (M+H)⁺.

Step 4. Hydrolysis of 7-chloro-3-(5-chloro-2-methoxy-benzenesulfonyl)-2,3-dihydrobenzooxazole-5-carboxylic acid methyl ester in analogy with example 1, step 4 produced 7-chloro-3-(5-chloro-2-methoxy-benzenesulfonyl)-2,3-dihydro-benzooxazole-5-carboxylic acid. White solid, MS (ISP)=402.1 (M−H)⁻.

Step 5. Reaction of 7-chloro-3-(5-chloro-2-methoxy-benzenesulfonyl)-2,3-dihydrobenzooxazole-5-carboxylic acid with ethyl 4-aminobenzoate in analogy with example 30, step 4 gave 4-{[7-chloro-3-(5-chloro-2-methoxy-benzenesulfonyl)-2,3-dihydro-benzooxazole-5-carbonyl]-amino}-benzoic acid ethyl ester. Light yellow solid, MS (ISP)=551.1 (M+H)⁺.

Step 6. Hydrolysis of 4-{[7-chloro-3-(5-chloro-2-methoxy-benzenesulfonyl)-2,3-dihydrobenzooxazole-5-carbonyl]-amino}-benzoic acid ethyl ester in analogy with example 1, step 6 afforded the title compound. White solid, MS (ISP)=520.9 (M−H)⁻.

Preparation of the Starting Material:

65% aq. nitric acid solution (2.4 mL, 54 mmol) and fuming nitric acid (2.2 mL, 54 mmol) were added at −10° C. to a solution of 3-chloro-4-hydroxy-benzoic acid methyl ester (5.00 g, 26.8 mmol) in diethyl ether (65 mL). The ice bath was removed and the reaction mixture was stirred at room temperature for 16 h, then partitioned between water and ethyl acetate. The organic layer was washed with brine, dried (MgSO$_4$), and evaporated to afford 3-chloro-4-hydroxy-5-nitro-benzoic acid methyl ester (6.24 g, 100%). Yellow solid, MS (ISP)=230.3 (M−H)⁻.

Example 51

4-{[8-Chloro-4-(5-chloro-2-methoxy-benzenesulfonyl)-3,4-dihydro-2H-benzo[1,4]oxazine-6-carbonyl]-amino}-benzoic acid The title compound, MS (ISP)=534.8 (M−H)⁻, was produced in analogy with example 36, steps 1-4. Step 1 was performed using 3-chloro-5-(5-chloro-2-methoxy-benzenesulfonylamino)-4-hydroxy-benzoic acid methyl ester (example 50, step 2) and 1,2-dibromoethane, yielding 8-chloro-4-(5-chloro-2-methoxy-benzenesulfonyl)-3,4-dihydro-2H-benzo[1,4]oxazine-6-carboxylic acid methyl ester, which was hydrolyzed in step 2 to afford 8-chloro-4-(5-chloro-2-methoxybenzenesulfonyl)-3,4-dihydro-2H-benzo[1,4]oxazine-6-carboxylic acid. This was reacted with ethyl 4-aminobenzoate in step 3 to produce 4-{[8-chloro-4-(5-chloro-2-methoxy-benzenesulfonyl)-3,4-dihydro-2H-benzo[1,4]oxazine-6-carbonyl]-amino}-benzoic acid ethyl ester, which was hydrolyzed in step 4.

Example 52

4-{[3-(5-Chloro-2-methoxy-benzenesulfonyl)-7-methyl-2,3-dihydro-benzooxazole-5-carbonyl]-amino}-benzoic acid The title compound was prepared as illustrated in schemes 1 and 6.

Step 1. 4-hydroxy-3-methyl-5-nitro-benzoic acid was hydrogenated in analogy with example 1, step 1 to produce 3-amino-4-hydroxy-5-methyl-benzoic acid methyl ester. Orange solid, MS (ISP)=180.1 (M−H)⁻.

Step 2. 3-Amino-4-hydroxy-5-methyl-benzoic acid methyl ester was reacted with 5-chloro-2-methoxybenzenesulfonyl chloride in accordance with the general method of example 40, step 2 and led to 3-(5-chloro-2-methoxy-benzenesulfonylamino)-4-hydroxy-5-methyl-benzoic acid methyl ester. Light brown solid, MS (ISP)=384.1 (M−H)⁻.

Step 3. Cyclization of 3-(5-chloro-2-methoxy-benzenesulfonylamino)-4-hydroxy-5-methyl-benzoic acid methyl ester with dibromomethane in accordance with example 30, step 2 furnished 3-(5-Chloro-2-methoxy-benzenesulfonyl)-7-methyl-2,3-dihydro-benzooxazole-5-carboxylic acid methyl ester. Off-white solid, MS (ISP)=398.1 (M+H)⁺.

Step 4. Hydrolysis of 3-(5-chloro-2-methoxy-benzenesulfonyl)-7-methyl-2,3-dihydrobenzooxazole-5-carboxylic acid methyl ester in analogy with example 1, step 6 produced 3-(5-chloro-2-methoxy-benzenesulfonyl)-7-methyl-2,3-dihydro-benzooxazole-5-carboxylic acid. White solid, MS (ISP)=381.9 (M−H)⁻.

Step 5. Reaction of 3-(5-chloro-2-methoxy-benzenesulfonyl)-7-methyl-2,3-dihydrobenzooxazole-5-carboxylic acid with ethyl 4-aminobenzoate in analogy with example 30, step 4 gave 4-{[3-(5-chloro-2-methoxy-benzenesulfonyl)-7-methyl-2,3-dihydro-benzooxazole-5-carbonyl]-amino}-benzoic acid ethyl ester. Orange solid, MS (ISP)=530.9 (M+H)⁺.

Step 6. Hydrolysis of 4-{[3-(5-chloro-2-methoxy-benzenesulfonyl)-7-methyl-2,3-dihydrobenzooxazole-5-carbonyl]-amino}-benzoic acid ethyl ester in analogy with example 1, step 6 afforded the title compound. Brown solid, MS (ISP)=501.1 (M−H)⁻.

Preparation of the Starting Material:

A solution of 4-hydroxy-3-methylbenzoic acid (5.00 g, 32.8 mmol) in 15% methanolic sulfuric acid solution (50 mL) was heated at reflux over 48 h, then poured upon ice and extracted with ethyl acetate. The organic layer was washed with 1 M aq. sodium carbonate solution and brine, dried (MgSO$_4$), and evaporated to afford 4-hydroxy-3-methyl-benzoic acid methyl ester (5.18 g, 95%). Brown solid, MS (ISP)=165.1 (M−H)⁻.

65% aq. nitric acid solution (2.7 mL, 60 mmol) and fuming nitric acid (2.5 mL, 60 mmol) were added at −10° C. to a solution of 4-hydroxy-3-methyl-benzoic acid methyl ester (4.97 g, 29.9 mmol) in diethyl ether (60 mL). The ice bath was removed and the reaction mixture was stirred at room temperature for 16 h, then partitioned between water and ethyl acetate. The organic layer was washed with brine, dried (MgSO$_4$), and evaporated to afford 4-hydroxy-3-methyl-5-nitro-benzoic acid (6.27 g, 99%). Yellow solid, MS (ISP)=210.1 (M−H)⁻.

Example 53

4-{[4-(5-Chloro-2-methoxy-benzenesulfonyl)-8-methyl-3,4-dihydro-2H-benzo[1,4]oxazine-6-carbonyl]-amino}-benzoic acid The title compound, MS (ISP)=514.9 (M−H)⁻, was produced in analogy with example 36, steps 1-4. Step 1 was performed using 3-(5-chloro-2-methoxy-benzenesulfonylamino)-4-hydroxy-5-methyl-benzoic acid methyl ester (example 52, step 2) and 1,2-dibromoethane, yielding 4-(5-chloro-2-methoxy-benzenesulfonyl)-8-methyl-3,4-dihydro-2H-benzo[1,4]oxazine-6-carboxylic acid methyl ester, which was hydrolyzed in step 2 to afford 4-(5-chloro-2-methoxy-benzenesulfonyl)-8-methyl-3,4-dihydro-2H-benzo[1,4]oxazine-6-carboxylic acid. This was reacted with ethyl 4-aminobenzoate in step 3 to produce 4-{[4-(5-chloro-2-methoxy-benzenesulfonyl)-8-methyl-3,4-dihydro-2H-benzo[1,4]oxazine-6-carbonyl]-amino}-benzoic acid ethyl ester, which was hydrolyzed in step 4.

Example 54

3-(5-Chloro-2-methoxy-benzenesulfonyl)-2,3-dihydro-benzooxazole-5-carboxylic acid (4-fluoro-phenyl)-amide The title compound, MS (ISP)=463.1 (M+H)⁺, was produced as described in example 30, steps 1-4. Step 4 was performed using 4-fluoroaniline as amine reagent.

Example 55

4-{[4-(5-Chloro-2-methoxy-benzenesulfonyl)-3,4-dihydro-2H-benzo[1,4]thiazine-6-carbonyl]-amino}-benzoic acid The title compound was prepared as illustrated in schemes 7 and 8.

Step 1. Borane-tetrahydrofuran complex solution (1 M in tetrahydrofuran, 45 mL, 45 mmol) was added at 0° C. to a suspension of methyl-3-oxo-3,4-dihydro-2H-1,4-benzothiazine-6-carboxylate (2.00 g, 8.96 mmol) in tetrahydrofuran (20 mL). The ice bath was removed, the homogenous solution stirred at room temperature for 2 h, then excess reagent was destroyed by careful addition of methanol (42 mL) at 0° C. After evaporation of volatile material, the residue was taken up in 5% methanolic sulfuric acid solution (25 mL) and the solution was heated at reflux over 80 min. After cooling, the reaction mixture was partitioned between ethyl acetate and water, the organic layer was dried ($MgSO_4$) and evaporated to produce 3,4-dihydro-2H-benzo[1,4]thiazine-6-carboxylic acid methyl ester (1.79 g, 96%). Light yellow solid, MS (ISP)=210.1 $(M+H)^+$.

Step 2. 3,4-Dihydro-2H-benzo[1,4]thiazine-6-carboxylic acid methyl ester was reacted with 5-chloro-2-methoxybenzenesulfonyl chloride in accordance with the general method of example 30, step 1 and led to 4-(5-chloro-2-methoxy-benzenesulfonyl)-3,4-dihydro-2H-benzo[1,4]thiazine-6-carboxylic acid methyl ester. Pink solid, MS (ISP)=414.2 $(M+H)^+$.

Step 3. Hydrolysis of 4-(5-chloro-2-methoxy-benzenesulfonyl)-3,4-dihydro-2H-benzo[1,4]thiazine-6-carboxylic acid methyl ester in accordance with the general method of example 1, step 4 produced 4-(5-chloro-2-methoxy-benzenesulfonyl)-3,4-dihydro-2H-benzo[1,4]thiazine-6-carboxylic acid. White solid, MS (ISP)=398.1 $(M-H)^-$.

Step 4. Reaction of 4-(5-chloro-2-methoxy-benzenesulfonyl)-3,4-dihydro-2H-benzo[1,4]thiazine-6-carboxylic acid with ethyl 4-aminobenzoate in accordance with the general method of example 30, step 4 produced 4-{[4-(5-chloro-2-methoxy-benzenesulfonyl)-3,4-dihydro-2H-benzo[1,4]thiazine-6-carbonyl]-amino}-benzoic acid ethyl ester. White solid, MS (ISP)=547.2 $(M+H)^+$.

Step 5. Hydrolysis of 4-{[4-(5-chloro-2-methoxy-benzenesulfonyl)-3,4-dihydro-2H-benzo[1,4]thiazine-6-carbonyl]-amino}-benzoic acid ethyl ester in accordance with the general method of example 1, step 6 produced the title compound. White solid, MS (ISP)=517.0 $(M-H)^-$.

Example 56

4-{[1-(5-Chloro-2-methoxy-benzenesulfonyl)-2,3-dihydro-1H-4-oxa-1,5-diaza-naphthalene-7-carbonyl]-amino}-benzoic acid The title compound was prepared as illustrated in scheme 7.

Step 1. Sodium hydride (55% dispersion in mineral oil, 603 mg, 13.8 mmol) was added to a solution of ethyl glycolate (1.43 g, 13.8 mmol) in 1,4-dioxane, and the reaction mixture was heated at 70° C. for 1 h, then 5-bromo-2-chloro-3-nitropyridine (Eur. Pat. Appl. EP 122109 (1984); 1.64 g, 6.91 mmol) was added, and stirring was continued at 70° C. for 1 h and at room temperature for 16 h. The reaction mixture was then neutralized with sat. aq. sodium hydrogencarbonate solution and extracted three times with dichloromethane. The organic layers were pooled, dried ($Na_2SO_4$), and evaporated. Chromatography ($SiO_2$, hexane-ethyl acetate gradient) furnished (5-bromo-3-nitropyridin-2-yloxy)-acetic acid ethyl ester (1.03 g, 49%). Light yellow liquid, MS (ISP)=305.1 $(M+H)^+$.

Step 2. Iron powder (22.8 g, 408 mmol) was added to a solution of (5-bromo-3-nitropyridin-2-yloxy)-acetic acid ethyl ester (2.28 g, 7.47 mmol) in acetic acid (230 mL), and the reaction mixture was heated at 60° C. over 150 min, cooled to room temperature, and filtered. The filtrate was evaporated, taken up in dichloromethane/methanol 1:1 and neutralized with 1 M aq. sodium carbonate solution. The organic layer was washed with water and the aqueous layer re-extracted with dichloromethane. The combined organic layers were washed again with 1 M aq. sodium carbonate solution, dried ($Na_2SO_4$), and evaporated to produce 7-bromo-1H-4-oxa-1,5-diaza-naphthalen-2-one (1.46 g, 85%). Off-white solid, MS (ISP)=226.9 $(M-H)^-$.

Step 3. Borane-tetrahydrofuran complex (1 M in tetrahydrofuran, 32 mL, 32 mmol) was added dropwise at 0° C. to a solution of 7-bromo-1H-4-oxa-1,5-diaza-naphthalen-2-one (1.45 g, 6.33 mmol) in tetrahydrofuran (240 mL). The ice bath was removed and the solution heated at reflux over 3 h, then volatile material was removed by distillation. The residue was taken up in 37% aq. hydrochloric acid solution and the reaction mixture, heated at 100° C. for 75 min, basified to pH 10 with 30% aq. sodium hydroxide solution, and extracted three times with dichloromethane. The combined organic layers were dried ($Na_2SO_4$) and evaporated to afford 7-bromo-2,3-dihydro-1H-4-oxa-1,5-diaza-naphthalene (944 mg, 69%). White solid, MS (ISP)=215.1 $(M+H)^+$.

Step 4. 7-Bromo-2,3-dihydro-1H-4-oxa-1,5-diaza-naphthalene was reacted with 5-chloro-2-methoxybenzenesulfonyl chloride in accordance with the general method of example 1, step 3 and led to 7-bromo-1-(5-chloro-2-methoxy-benzenesulfonyl)-2,3-dihydro-1H-4-oxa-1,5-diaza-naphthalene. White solid, MS (ISP)=420.9 $(M+H)^+$ Step 5. A solution of 7-bromo-1-(5-chloro-2-methoxy-benzenesulfonyl)-2,3-dihydro-1H-4-oxa-1,5-diaza-naphthalene (200 mg, 0.476 mmol), triethylamine (120 mg, 1.19 mmol), and dichloro[1,1'-bis(diphenylphosphino)ferrocene] palladium dichloromethane complex (19 mg, 29 μmol) in ethanol (2 mL) and ethyl acetate (2 mL) was heated at 110° C. under a carbon monoxide atmosphere (70 bar) for 20 h. The reaction mixture was evaporated and the residue chromatographed ($SiO_2$, toluene-acetonitrile gradient) to produce 1-(5-chloro-2-methoxy-benzenesulfonyl)-2,3-dihydro-1H-4-oxa-1,5-diaza-naphthalene-7-carboxylic acid ethyl ester (132 mg, 67%). Off-white solid, MS (ISP)=413.2 $(M+H)^+$.

Step 6. A mixture of 1-(5-chloro-2-methoxy-benzenesulfonyl)-2,3-dihydro-1H-4-oxa-1,5-diaza-naphthalene-7-carboxylic acid ethyl ester (124 mg, 0.30 mmol) in tetrahydrofuran (0.6 mL) and 1 M aq. potassium hydroxide solution (0.60 mL, 0.60 mmol) was stirred at 50° C. over 72 h. Evaporation of volatile material furnished 1-(5-chloro-2-methoxy-benzenesulfonyl)-2,3-dihydro-1H-4-oxa-1,5-diaza-naphthalene-7-carboxylic acid potassium salt (116 mg), which was directly used in the next step. Light yellow solid, MS (ISP)=383.1 $(M-K)^-$.

Step 7. Reaction of 1-(5-chloro-2-methoxy-benzenesulfonyl)-2,3-dihydro-1H-4-oxa-1,5-diaza-naphthalene-7-carboxylic acid potassium salt with tert-butyl 4-aminobenzoate in accordance with the general method of example 30, step 4 produced 4-{[1-(5-chloro-2-methoxy-benzenesulfonyl)-2,3-dihydro-1H-4-oxa-1,5-diaza-naphthalene-7-carbonyl]-amino}-benzoic acid tert-butyl ester. White solid, MS (ISP)=560.1 $(M+H)^+$.

Step 8. 4-{[1-(5-chloro-2-methoxy-benzenesulfonyl)-2,3-dihydro-1H-4-oxa-1,5-diaza-naphthalene-7-carbonyl]-amino}-benzoic acid tert-butyl ester (27 mg, 48 µmol) was dissolved in hydrogen chloride solution (4 M in 1,4-dioxane, 1.0 mL) and stirred at room temperature for 4 days, then the precipitate was collected by filtration and washed with ethyl acetate to produce the title compound (21 mg, 86%). White solid, MS (ISP)=502.0 (M−H)⁻.

Example 57

1-(5-chloro-2-methoxy-benzenesulfonyl)-2,3-dihydro-1H-4-oxa-1,5-diaza-naphthalene-7-carboxylic acid phenylamide The title compound, MS (ISP)=460.1 (M+H)⁺, was produced in analogy with example 30, step 4 from 1-(5-chloro-2-methoxy-benzenesulfonyl)-2,3-dihydro-1H-4-oxa-1,5-diaza-naphthalene-7-carboxylic acid potassium salt (example 56, step 6) and aniline.

Example 58

4-(5-Chloro-2-methoxy-benzenesulfonyl)-4H-benzo[1,4]oxazine-6-carboxylic acid phenylamide The title compound was prepared as illustrated in schemes 1, 4, and 5.
Step 1. Allyl bromide (195 mg, 1.63 mmol) and potassium carbonate (372 mg, 2.69 mmol) was added to a solution of 3-(5-chloro-2-methoxy-benzenesulfonylamino)-4-hydroxy-benzoic acid methyl ester (example 30, step 1; 200 mg, 0.538 mmol) in acetone, and the reaction mixture was stirred at 60° C. for 16 h. After cooling, insoluble material was filtered off and the filtrate evaporated to produce 3-[allyl-(5-chloro-2-methoxy-benzenesulfonyl)-amino]-4-allyloxy-benzoic acid methyl ester (243 mg, 100%). Orange solid, MS (ISP)=452.1 (M+H)⁺.
Step 2. A solution of 3-[allyl-(5-chloro-2-methoxy-benzenesulfonyl)-amino]-4-allyloxy-benzoic acid methyl ester (243 mg, 0.537 mmol) and carbonylchlorohydrotris(triphenylphosphine)ruthenium (15 mg, 16 mmol) in toluene (2.6 mL) was stirred at 95° C. for 16 h, then another portion of carbonylchlorohydrotris(triphenylphosphine)ruthenium (27 mg, 25 mmol) was added, and stirring was continued over 48 h, then the solvent was evaporated. Chromatography (SiO₂, heptane-ethyl acetate gradient) furnished 3-[(5-chloro-2-methoxy-benzenesulfonyl)-propenyl-amino]-4-[(propenyl)oxy]-benzoic acid methyl ester (177 mg, 73%). Light red oil, MS (ISP)=452.1 (M+H)⁺.
Step 3. A solution of 3-[(5-chloro-2-methoxy-benzenesulfonyl)-propenyl-amino]-4-[(propenyl)oxy]-benzoic acid methyl ester (170 mg, 0.378 mmol) and dichloro(1,3-dimesityl-4,5-dihydroimidazol-2-ylidene)(phenylmethylene)(tricyclohexylphosphine)ruthenium (32 mg, 38 mmol) in toluene (1.7 mL) was stirred at 45° C. for 24 h, then the solvent was evaporated. Chromatography (SiO₂, heptane-ethyl acetate gradient) afforded 4-(5-chloro-2-methoxy-benzenesulfonyl)-4H-benzo[1,4]oxazine-6-carboxylic acid methyl ester (75 mg, 50%). Light red solid, MS (ISP)=395.7 (M+H)⁺.
Step 4. Hydrolysis of 4-(5-chloro-2-methoxy-benzenesulfonyl)-4H-benzo[1,4]oxazine-6-carboxylic acid methyl ester in accordance with the general method of example 1, step 4 produced 4-(5-chloro-2-methoxy-benzenesulfonyl)-4H-benzo[1,4]oxazine-6-carboxylic acid. Light red solid, MS (ISP)=380.1 (M−H)⁻.

Step 5. Reaction of 4-(5-chloro-2-methoxy-benzenesulfonyl)-4H-benzo[1,4]oxazine-6-carboxylic acid with aniline in accordance with the general method of example 30, step 4 produced the title compound. Orange solid, MS (ISP)=455.2 (M−H)⁻.

Example 59

(2-{[3-(5-Chloro-2-methoxy-benzenesulfonyl)-2,3-dihydro-benzooxazole-5-carbonyl]-amino}-thiazol-4-yl)-acetic acid The title compound, MS (ISP)=508.1 (M−H)⁻, was produced as described in example 30, steps 1-5. Step 4 was performed using ethyl 2-amino-4-thiazoleacetate and yielded (2-{[3-(5-chloro-2-methoxy-benzenesulfonyl)-2,3-dihydro-benzooxazole-5-carbonyl]-amino}-thiazol-4-yl)acetic acid ethyl ester, which was hydrolyzed in step 5.

Example 60

(3-{[3-(5-Chloro-2-methoxy-benzenesulfonyl)-2,3-dihydro-benzooxazole-5-carbonyl]-amino}-phenyl)-acetic acid The title compound, MS (ISP)=501.0 (M−H)⁻, was produced as described in example 30, steps 1-5. Step 4 was performed using ethyl (3-aminophenyl)acetate and yielded (3-{[3-(5-chloro-2-methoxy-benzenesulfonyl)-2,3-dihydro-benzooxazole-5-carbonyl]-amino}-phenyl)-acetic acid ethyl ester, which was hydrolyzed in step 5.

Example 61

(4-{[3-(5-Chloro-2-methoxy-benzenesulfonyl)-2,3-dihydro-benzooxazole-5-carbonyl]-amino}-phenyl)-acetic acid The title compound, MS (ISP)=501.1 (M−H)⁻, was produced as described in example 30, steps 1-5. Step 4 was performed using ethyl (4-aminophenyl)acetate and yielded (4-{[3-(5-chloro-2-methoxy-benzenesulfonyl)-2,3-dihydro-benzooxazole-5-carbonyl]-amino}-phenyl)-acetic acid ethyl ester, which was hydrolyzed in step 5.

Example 62

(2-{[4-(5-Chloro-2-methoxy-benzenesulfonyl)-8-fluoro-3,4-dihydro-2H-benzo[1,4]oxazine-6-carbonyl]-amino}-thiazol-4-yl)-acetic acid The title compound, MS (ISP)=540.1 (M−H)⁻, was produced as described in example 47, steps 1-4. Step 3 was performed using ethyl 2-amino-4-thiazoleacetate and yielded (2-{[4-(5-chloro-2-methoxy-benzenesulfonyl)-8-fluoro-3,4-dihydro-2H-benzo[1,4]oxazine-6-carbonyl]-amino}-thiazol-4-yl)-acetic acid ethyl ester, which was hydrolyzed in step 4.

Example 63

(4-{[4-(5-Chloro-2-methoxy-benzenesulfonyl)-8-fluoro-3,4-dihydro-2H-benzo[1,4]oxazine-6-carbonyl]-amino}-phenyl)-acetic acid The title compound, MS (ISP)=533.0 (M−H)⁻, was produced as described in example 47, steps 1-4. Step 3 was performed using ethyl (4-aminophenyl)acetate and yielded (4-{[4-(5-chloro-2-methoxy-benzenesulfonyl)-8-fluoro-3,4-dihydro-2H-benzo[1,4]oxazine-6-carbonyl]-amino}-phenyl)-acetic acid ethyl ester, which was hydrolyzed in step 4.

Example 64

(2-{[3-(5-Chloro-2-methoxy-benzenesulfonyl)-7-fluoro-2,3-dihydro-benzooxazole-5-carbonyl]-amino}-thiazol-4-yl)-acetic acid The title compound, MS (ISP)=526.1 (M−H)⁻, was produced as described in example 44, steps 1-5. Step 4 was performed using ethyl 2-amino-4-thiazoleacetate and yielded (2-{[4-(5-chloro-2-methoxy-benzenesulfonyl)-7-fluoro-2,3-dihydro-benzooxazole-5-carbonyl]-amino}-thiazol-4-yl)-acetic acid ethyl ester, which was hydrolyzed in step 5.

Example 65

(4-{[3-(5-Chloro-2-methoxy-benzenesulfonyl)-7-fluoro-2,3-dihydro-benzooxazole-5-carbonyl]-amino}-phenyl)-acetic acid The title compound, MS (ISP)=519.1 (M−H)⁻, was produced as described in example 44, steps 1-5. Step 4 was performed using ethyl (4-aminophenyl)acetate and yielded (2-{[3-(5-chloro-2-methoxy-benzenesulfonyl)-7-fluoro-2,3-dihydro-benzooxazole-5-carbonyl]-amino}-thiazol-4-yl)acetic acid ethyl ester, which was hydrolyzed in step 5.

Example 66

(2-{[4-(5-Chloro-2-methoxy-benzenesulfonyl)-3,4-dihydro-2H-benzo[1,4]oxazine-6-carbonyl]-amino}-thiazol-4-yl)-acetic acid The title compound, MS (ISP)=522.2 (M−H)⁻, was produced in analogy with example 36, steps 1-4. Step 1 was performed using 3-(5-chloro-2-methoxy-benzenesulfonylamino)-4-hydroxy-benzoic acid methyl ester (example 30, step 1) and 1,2-dibromoethane, yielding 4-(5-chloro-2-methoxy-benzenesulfonyl)-3,4-dihydro-2H-benzo[1,4]oxazine-6-carboxylic acid methyl ester, which was hydrolyzed in step 2 to afford 4-(5-chloro-2-methoxy-benzenesulfonyl)-3,4-dihydro-2H-benzo[1,4]oxazine-6-carboxylic acid. This was reacted with ethyl 2-amino-4-thiazoleacetate in step 3 to produce (2-{[4-(5-chloro-2-methoxy-benzenesulfonyl)-3,4-dihydro-2H-benzo[1,4]oxazine-6-carbonyl]-amino}-thiazol-4-yl)-acetic acid ethyl ester, which was hydrolyzed in step 4.

Example 67

(4-{[4-(5-Chloro-2-methoxy-benzenesulfonyl)-3,4-dihydro-2H-benzo[1,4]oxazine-6-carbonyl]-amino}-phenyl)-acetic acid The title compound, MS (ISP)=515.2 (M−H)⁻, was produced as described in example 66, steps 1-4. Step 3 was performed using ethyl (4-aminophenyl)acetate and yielded (4-{[4-(5-chloro-2-methoxy-benzenesulfonyl)-3,4-dihydro-2H-benzo[1,4]oxazine-6-carbonyl]-amino}-phenyl)acetic acid ethyl ester, which was hydrolyzed in step 4.

Example 68

(2-{[4-(5-Chloro-2-methoxy-benzenesulfonyl)-3,4-dihydro-2H-benzo[1,4]thiazine-6-carbonyl]-amino}-thiazol-4-yl)-acetic acid The title compound, MS (ISP)=540.1 (M+H)⁺, was produced as described in example 55, steps 1-5. Step 4 was performed using ethyl 2-amino-4-thiazoleacetate and yielded (2-{[4-(5-chloro-2-methoxy-benzenesulfonyl)-3,4-dihydro-2H-benzo[1,4]thiazine-6-carbonyl]-amino}-thiazol-4-yl)-acetic acid ethyl ester, which was hydrolyzed in step 5.

Example 69

(4-{[4-(5-Chloro-2-methoxy-benzenesulfonyl)-3,4-dihydro-2H-benzo[1,4]thiazine-6-carbonyl]-amino}-phenyl)-acetic acid The title compound, MS (ISP)=531.1 (M−H)⁻, was produced as described in example 55, steps 1-5. Step 4 was performed using ethyl (4-aminophenyl)acetate and yielded (4-{[4-(5-chloro-2-methoxy-benzenesulfonyl)-3,4-dihydro-2H-benzo[1,4]thiazine-6-carbonyl]-amino}-phenyl)acetic acid ethyl ester, which was hydrolyzed in step 5.

Example 70

4-{[4-(5-Chloro-2-methoxy-benzenesulfonyl)-1,1-dioxo-1,2,3,4-tetrahydro-benzo[1,4]thiazine-6-carbonyl]-amino}-benzoic acid The title compound was prepared as illustrated in schemes 7, 8, and 13.

Step 1. Reaction of 4-(5-chloro-2-methoxy-benzenesulfonyl)-3,4-dihydro-2H-benzo[1,4]-thiazine-6-carboxylic acid (example 55, step 3) with tert-butyl 4-aminobenzoate in accordance with the general method of example 30, step 4 produced 4-{[4-(5-chloro-2-methoxy-benzenesulfonyl)-3,4-dihydro-2H-benzo[1,4]thiazine-6-carbonyl]-amino}-benzoic acid tert-butyl ester. White solid, MS (ISP)=575.2 (M+H)⁺.

Step 2. A suspension of 4-{[4-(5-chloro-2-methoxy-benzenesulfonyl)-3,4-dihydro-2H-benzo[1,4]thiazine-6-carbonyl]-amino}-benzoic acid tert-butyl ester (100 mg, 0.174 mmol) in formic acid (2 mL) was treated with 30% aq. hydrogen peroxide solution (89 µL, 0.87 mmol) and stirred at room temperature, then after 24 h another portion of 30% aq. hydrogen peroxide solution (89 µL, 0.87 mmol) was added. After a total reaction time of 48 h water (7 mL) was added, then after 30 min the precipitate was collected by filtration and dried to afford the title compound (75 mg, 79%). White solid, MS (ISP)=549.2 (M−H)⁻.

Example 71

4-(5-Chloro-2-methoxy-benzenesulfonyl)-3,4-dihydro-2H-benzo[1,4]oxazine-6-carboxylic acid phenylamide The title compound, MS (ISP)=459.2 (M+H)⁺, was produced as described in example 66, steps 1-3. Step 3 was performed using aniline as amine reagent.

Example 72

3-{[4-(5-Chloro-2-methoxy-benzenesulfonyl)-3,4-dihydro-2H-benzo[1,4]oxazine-6-carbonyl]-amino}-benzoic acid The title compound, MS (ISP)=501.3 (M−H)⁻, was produced as described in example 66, steps 1-4. Step 3 was performed using methyl 3-aminobenzoate and yielded 3-{[4-(5-chloro-2-methoxy-benzenesulfonyl)-3,4-dihydro-2H-benzo[1,4]oxazine-6-carbonyl]-amino}-benzoic acid methyl ester, which was hydrolyzed in step 4.

Example 73

4-{[1-(5-Chloro-2-methoxy-benzenesulfonyl)-1,4-dihydro-2H-benzo[d][1,3]oxazine-7-carbonyl]-amino}-benzoic acid The title compound was prepared as illustrated in scheme 10.

Step 1. Borane tetrahydrofuran complex solution (1 M in tetrahydrofuran, 13 mL, 13 mmol) was added over 5 min to a solution of 4-bromo-2-nitrobenzoic acid (2.00 g, 8.13 mmol) at room temperature, then after 72 h the reaction mixture was carefully poured upon sat. aq. sodium hydrogencarbonate solution and extracted with ethyl acetate. The organic layer was dried (MgSO₄) and evaporated to produce (4-bromo-2-nitro-phenyl)-methanol (1.85 g, 96%). White solid, ¹H-NMR (300 MHz, CDCl₃): 8.25 (d, J=1.8, 1 H), 7.80 (dd, J=8.1, 1.8, 1 H), 7.67 (d, J=8.1, 1 H), 4.96 (d, J=6.3, 2 H), 2.37 (t, J=6.3, 1 H).

Step 2. A mixture of (4-bromo-2-nitro-phenyl)-methanol (1.85 g, 7.97 mmol), iron powder (2.23 g, 39.9 mmol), ammonium chloride (213 mg, 3.99 mmol), ethanol (20 mL), and water (10 mL) was heated at 75° C. for 1 h, then after cooling filtered through a pad of diatomaceous earth. The filtrate was evaporated and the residue partitioned between ethyl acetate and water, the organic layer was washed with brine, dried (MgSO₄), and evaporated to produce (2-amino-4-bromophenyl)-methanol (1.53 g, 90%). Off-white solid, MS (EI)=201.0 (M⁺).

Step 3. A solution of (2-amino-4-bromo-phenyl)-methanol (1.53 g, 7.57 mmol) in pyridine (15 mL) was treated with 5-chloro-2-methoxybenzenesulfonyl chloride (1.85 g, 7.57 mmol) at room temperature and stirred for 72 h, then poured upon ice-cold 2 M aq. hydrochloric acid solution and extracted with ethyl acetate. The organic layer was washed with brine, dried (MgSO₄), and evaporated to produce a gummy residue, from which the product was precipitated by addition of toluene. The precipitate was collected by filtration and dried to afford N-(5-bromo-2-hydroxymethyl-phenyl)-5-chloro-2-methoxy-benzenesulfonamide (2.51 g, 82%). Off-white solid, MS (ISP)=404.2 (M−H)⁻.

Step 4. A mixture of N-(5-bromo-2-hydroxymethyl-phenyl)-5-chloro-2-methoxy-benzenesulfonamide (2.51 g, 6.17 mmol), toluene-4-sulfonic acid monohydrate (117 mg, 0.617 mmol), and formaldehyde diethyl acetal (15.5 mL) was heated under reflux at 100° C. for 16 h. After cooling, heptane was added to the suspension, which was stirred for 15 min. The precipitate was collected by filtration and dried to afford 7-bromo-1-(5-chloro-2-methoxy-benzenesulfonyl)-1,4-dihydro-2H-benzo[d][1,3]oxazine (2.25 g, 87%). Off-white solid, MS (ISP)=418.1 (M+H)⁺.

Step 5. A solution of 7-bromo-1-(5-chloro-2-methoxy-benzenesulfonyl)-1,4-dihydro-2H-benzo[d][1,3]oxazine (2.00 g, 4.78 mmol), triethylamine (1.21 g, 11.9 mmol), and dichloro[1,1'-bis(diphenylphosphino)ferrocene]palladium dichloromethane complex (200 mg, 0.239 mmol) in methanol (30 mL) and ethyl acetate (30 mL) was heated at 130° C. under a carbon monoxide atmosphere (100 bar) for 3 h. The reaction mixture was evaporated and the residue chromatographed (SiO₂, heptane-ethyl acetate gradient) to produce 1-(5-chloro-2-methoxybenzenesulfonyl)-1,4-dihydro-2H-benzo[d][1,3]oxazine-7-carboxylic acid methyl ester (825 mg, 43%). Orange solid, MS (ISP)=398.1 (M+H)⁺.

Step 6. Hydrolysis of 1-(5-chloro-2-methoxy-benzenesulfonyl)-1,4-dihydro-2H-benzo[d][1,3]-7-carboxylic acid methyl ester in accordance with the general method of example 1, step 4 produced 1-(5-chloro-2-methoxy-benzenesulfonyl)-1,4-dihydro-2H-benzo[d][1,3]oxazine-7-carboxylic acid. Off-white solid, MS (ISP)=382.3 (M−H)⁻.

Step 7. Reaction of 1-(5-chloro-2-methoxy-benzenesulfonyl)-1,4-dihydro-2H-benzo[d][1,3]oxazine-7-carboxylic acid with ethyl 4-aminobenzoate in accordance with the general method of example 30, step 4 produced 4-{[1-(5-chloro-2-methoxy-benzenesulfonyl)-1,4-dihydro-2H-benzo[d][1,3]oxazine-7-carbonyl]-amino}-benzoic acid ethyl ester. White foam, MS (ISP)=531.1 (M+H)⁺.

Step 8. Hydrolysis of 4-{[1-(5-chloro-2-methoxy-benzenesulfonyl)-1,4-dihydro-2H-benzo[d][1,3]oxazine-7-carbonyl]-amino}-benzoic acid ethyl ester in accordance with the general method of example 1, step 6 produced the title compound. White solid, MS (ISP)=503.1 (M+H)⁺.

Example 74

(2-{[1-(5-Chloro-2-methoxy-benzenesulfonyl)-1,4-dihydro-2H-benzo[d][1,3]oxazine-7-carbonyl]-amino}-thiazol-4-yl)-acetic acid The title compound, MS (ISP)=524.2 (M+H)⁺, was produced as described in example 73, steps 1-8. Step 7 was performed using ethyl 2-amino-4-thiazoleacetate and yielded (2-{[4-(5-chloro-2-methoxy-benzenesulfonyl)-1,4-dihydro-2H-benzo[d][1,3]oxazine-7-carbonyl]-amino}-thiazol-4-yl)-acetic acid ethyl ester, which was hydrolyzed in step 8.

Example 75

(4-{[1-(5-Chloro-2-methoxy-benzenesulfonyl)-1,4-dihydro-2H-benzo[d][1,3]oxazine-7-carbonyl]-amino}-phenyl)-acetic acid The title compound, MS (ISP)=517.1 (M+H)⁺, was produced as described in example 73, steps 1-8. Step 7 was performed using ethyl (4-aminophenyl)acetate and yielded (4-{[1-(5-chloro-2-methoxy-benzenesulfonyl)-1,4-dihydro-2H-benzo[d][1,3]oxazine-7-carbonyl]-amino}-phenyl)acetic acid ethyl ester, which was hydrolyzed in step 8.

Example 76

2-Chloro-5-{[4-(5-chloro-2-methoxy-benzenesulfonyl)-3,4-dihydro-2H-benzo[1,4]oxazine-6-carbonyl]-amino}-benzoic acid The title compound, MS (ISP)=535.0 (M−H)⁻, was produced as described in example 66, steps 1-4. Step 3 was performed using methyl 5-amino-2-chlorobenzoate and yielded 2-chloro-5-{[4-(5-chloro-2-methoxy-benzenesulfonyl)-3,4-dihydro-2H-benzo[1,4]oxazine-6-carbonyl]-amino}-benzoic acid methyl ester, which was hydrolyzed in step 4.

Example 77

(2-{[4-(5-Chloro-2-methoxy-benzenesulfonyl)-8-trifluoromethyl-3,4-dihydro-2H-benzo[1,4]oxazine-6-carbonyl]-amino}-thiazol-4-yl)-acetic acid The title compound, MS (ISP)=590.2 (M−H)⁻, was produced as described in example 41, steps 1-4. Step 3 was performed using ethyl 2-amino-4-thiazoleacetate and yielded (2-{[4-(5-chloro-2-methoxy-benzenesulfonyl)-8-trifluoromethyl-3,4-dihydro-2H-benzo[1,4]oxazine-6-carbonyl]-amino}-thiazol-4-yl)-acetic acid ethyl ester, which was hydrolyzed in step 4.

Example 79

(2-{[4-(5-Chloro-2-methoxy-benzenesulfonyl)-8-methyl-3,4-dihydro-2H-benzo[1,4]oxazine-6-carbonyl]-amino}-thiazol-4-yl)-acetic acid The title compound, MS (ISP)=536.1 (M−H)⁻, was produced as described in example 53, steps 1-4. Step 3 was performed using ethyl 2-amino-4-thiazoleacetate and yielded (2-{[4-(5-chloro-2-methoxy-benzenesulfonyl)-8-methyl-3,4-dihydro-2H-benzo[1,4]oxazine-6-carbonyl]-amino}-thiazol-4-yl)-acetic acid ethyl ester, which was hydrolyzed in step 4.

Example 80

(4-{[3-(5-Chloro-2-methoxy-benzenesulfonyl)-7-methyl-2,3-dihydro-benzooxazole-5-carbonyl]-amino}-phenyl)-acetic acid The title compound, MS (ISP)=515.1 (M−H)⁻, was produced as described in example 52, steps 1-6. Step 5 was performed using ethyl (4-aminophenyl)acetate and yielded (4-{[3-(5-chloro-2-methoxy-benzenesulfonyl)-7-methyl-2,3-dihydro-benzooxazole-5-carbonyl]-amino}-phenyl)acetic acid ethyl ester, which was hydrolyzed in step 6.

Example 81

(2-{[3-(5-Chloro-2-methoxy-benzenesulfonyl)-7-methyl-2,3-dihydro-benzooxazole-5-carbonyl]-amino}-thiazol-4-yl)-acetic acid The title compound, MS (ISP)=522.1 (M−H)⁻, was produced as described in example 52, steps 1-6. Step 5 was performed using ethyl 2-amino-4-thiazoleacetate and yielded (2-{[4-(5-chloro-2-methoxy-benzenesulfonyl)-7-methyl-2,3-dihydro-benzooxazole-5-carbonyl]-amino}-thiazol-4-yl)-acetic acid ethyl ester, which was hydrolyzed in step 6.

Example 82

(4-{[4-(5-Chloro-2-methoxy-benzenesulfonyl)-8-methyl-3,4-dihydro-2H-benzo[1,4]oxazine-6-carbonyl]-amino}-phenyl)-acetic acid The title compound, MS (ISP)=529.0 (M−H)⁻, was produced as described in example 53, steps 1-4. Step 3 was performed using ethyl (4-aminophenyl)acetate and yielded (4-{[4-(5-chloro-2-methoxy-benzenesulfonyl)-8-methyl-3,4-dihydro-2H-benzo[1,4]oxazine-6-carbonyl]-amino}-phenyl)-acetic acid ethyl ester, which was hydrolyzed in step 4.

Example 83

(2-{[4-(5-Chloro-2-methoxy-benzenesulfonyl)-3,4-dihydro-2H-benzo[1,4]oxazine-6-carbonyl]-amino}-thiazol-5-yl)-acetic acid The title compound, MS (ISP)=522.1 (M−H)⁻, was produced as described in example 66, steps 1-4. Step 3 was performed using ethyl (2-amino-thiazol-5-yl)-acetate and yielded (2-{[4-(5-chloro-2-methoxy-benzenesulfonyl)-3,4-dihydro-2H-benzo[1,4]oxazine-6-carbonyl]-amino}-thiazol-5-yl)-acetic acid ethyl ester, which was hydrolyzed in step 4.

Example 84

2-{[4-(5-Chloro-2-methoxy-benzenesulfonyl)-3,4-dihydro-2H-benzo[1,4]oxazine-6-carbonyl]-amino}-thiazole-5-carboxylic acid The title compound, MS (ISP)=508.1 (M−H)⁻, was produced as described in example 66, steps 1-4. Step 3 was performed using 2-amino-thiazole-5-carboxylic acid ethyl ester and yielded 2-{[4-(5-chloro-2-methoxy-benzenesulfonyl)-3,4-dihydro-2H-benzo[1,4]oxazine-6-carbonyl]-amino}-thiazole-5-carboxylic acid ethyl ester, which was hydrolyzed in step 4.

Example 85

(3-{[4-(5-Chloro-2-methoxy-benzenesulfonyl)-3,4-dihydro-2H-benzo[1,4]oxazine-6-carbonyl]-amino}-phenyl)-acetic acid The title compound, MS (ISP)=515.1 (M−H)⁻, was produced as described in example 66, steps 1-4. Step 3 was performed using ethyl (3-aminophenyl)acetate and yielded (3-{[4-(5-chloro-2-methoxy-benzenesulfonyl)-3,4-dihydro-2H-benzo[1,4]oxazine-6-carbonyl]-amino}-phenyl)acetic acid ethyl ester, which was hydrolyzed in step 4.

Example 86

3-(4-{[4-(5-Chloro-2-methoxy-benzenesulfonyl)-3,4-dihydro-2H-benzo[1,4]oxazine-6-carbonyl]-amino}-phenyl)-propionic acid The title compound, MS (ISP)=529.0 (M−H)⁻, was produced as described in example 66, steps 1-4. Step 3 was performed using 3-(4-amino-phenyl)-propionic acid ethyl ester and yielded 3-(4-{[4-(5-chloro-2-methoxy-benzenesulfonyl)-3,4-dihydro-2H-benzo[1,4]oxazine-6-carbonyl]-amino}-phenyl)-propionic acid ethyl ester, which was hydrolyzed in step 4.

Example 88

(3-{[4-(5-Chloro-2-methoxy-benzenesulfonyl)-3,4-dihydro-2H-benzo[1,4]oxazine-6-carbonyl]-amino}-pyrazol-1-yl)-acetic acid The title compound, MS (ISP)=505.3 (M−H)⁻, was produced as described in example 66, steps 1-4. Step 3 was performed using (3-amino-pyrazol-1-yl)-acetic acid ethyl ester and yielded (3-{[4-(5-chloro-2-methoxy-benzenesulfonyl)-3,4-dihydro-2H-benzo[1,4]oxazine-6-carbonyl]-amino}-pyrazol-1-yl)-acetic acid ethyl ester, which was hydrolyzed in step 4.

Example 89

4-{[4-(5-Chloro-2-methoxy-benzenesulfonyl)-3,4-dihydro-2H-benzo[1,4]oxazine-6-carbonyl]-amino}-2-cyano-benzoic acid Step 1. Reaction of 4-(5-chloro-2-methoxy-benzenesulfonyl)-3,4-dihydro-2H-benzo-[1,4]oxazine-6-carboxylic acid (example 1, step 4) with 2-bromo-5-aminobenzonitrile in accordance with the general method of example 30, step 4 produced 4-(5-chloro-2-methoxy-benzenesulfonyl)-3,4-dihydro-2H-benzo[1,4]oxazine-6-carboxylic acid (4-bromo-3-cyano-phenyl)-amide. White solid, MS (ISP)=562.1 (M+H)$^+$.

Step 2. A solution of 4-(5-chloro-2-methoxy-benzenesulfonyl)-3,4-dihydro-2H-benzo-[1,4]oxazine-6-carboxylic acid (4-bromo-3-cyano-phenyl)-amide (109 mg, 0.194 mmol), triethylamine (49 mg, 0.48 mmol), and dichloro[1,1'-bis(diphenylphosphino)ferrocene]palladium dichloromethane complex (20 mg, 25 μmol) in ethyl acetate (1.5 mL) and 1-propanol (1.5 mL) was heated at 110° C. under a carbon monoxide atmosphere for 16 h, then volatile material was removed by distillation. Chromatography of the residue (SiO$_2$; heptane-ethyl acetate gradient, then dichloromethane/methanol 9:1) followed by trituration in dichloromethane produced 4-{[4-(5-chloro-2-methoxy-benzenesulfonyl)-3,4-dihydro-2H-benzo[1,4]oxazine-6-carbonyl]-amino}-2-cyano-benzoic acid propyl ester (46 mg, 42%). White solid, MS (ISP)=568.2 (M−H)$^-$.

Step 3. Hydrolysis of 4-{[4-(5-chloro-2-methoxy-benzenesulfonyl)-3,4-dihydro-2H-benzo[1,4]oxazine-6-carbonyl]-amino}-2-cyano-benzoic acid propyl ester, in accordance with the general method of example 1, step 6 produced the title compound. White solid, MS (ISP)=526.4 (M−H)$^-$.

Example 90

2-Fluoro-4-{[4-(2-methoxy-5-methyl-benzenesulfonyl)-3,4-dihydro-2H-benzo[1,4]oxazine-6-carbonyl]-amino}-benzoic acid The title compound, MS (ISP)=501.1 (M+H)$^+$, was produced as described in example 1, steps 1-6. Step 3 was performed using 2-methoxy-5-methylbenzenesulfonyl chloride, furnishing 4-(2-methoxy-5-methyl-benzenesulfonyl)-3,4-dihydro-2H-benzo[1,4]oxazine-6-carboxylic acid methyl ester, which was hydrolyzed in step 4, leading to 4-(2-methoxy-5-methyl-benzenesulfonyl)-3,4-dihydro-2H-benzo[1,4]oxazine-6-carboxylic acid. This was reacted with ethyl 4-amino-2-fluorobenzoate in step 5 and yielded 2-fluoro-4-{[4-(2-methoxy-5-methyl-benzenesulfonyl)-3,4-dihydro-2H-benzo[1,4]oxazine-6-carbonyl]-amino}-benzoic acid ethyl ester, which was hydrolyzed in step 6.

Example 91

(2-{[4-(Toluene-3-sulfonyl)-3,4-dihydro-2H-benzo[1,4]oxazine-6-carbonyl]-amino}-thiazol-4-yl)-acetic acid The title compound, MS (ISP)=472.1 (M−H)$^-$, was produced as described in example 1, steps 1-6. Step 3 was performed using 3-methylbenzenesulfonyl chloride, furnishing 4-(toluene-3-sulfonyl)-3,4-dihydro-2H-benzo[1,4]oxazine-6-carboxylic acid methyl ester, which was hydrolyzed in step 4, leading to 4-(toluene-3-sulfonyl)-3,4-dihydro-2H-benzo[1,4]oxazine-6-carboxylic acid. This was reacted with ethyl 2-amino-4-thiazoleacetate in step 5 and yielded (2-{[4-(toluene-3-sulfonyl)-3,4-dihydro-2H-benzo[1,4]oxazine-6-carbonyl]-amino}-thiazol-4-yl)-acetic acid ethyl ester, which was hydrolyzed in step 6.

Example 92

(2-{[4-(3-Chloro-benzenesulfonyl)-3,4-dihydro-2H-benzo[1,4]oxazine-6-carbonyl]-amino}-thiazol-4-yl)-acetic acid The title compound, MS (ISP)=492.0 (M−H)$^-$, was produced as described in example 1, steps 1-6. Step 3 was performed using 3-chlorobenzenesulfonyl chloride, furnishing 4-(3-chlorobenzenesulfonyl)-3,4-dihydro-2H-benzo[1,4]oxazine-6-carboxylic acid methyl ester, which was hydrolyzed in step 4, leading to 4-(3-chloro-benzenesulfonyl)-3,4-dihydro-2H-benzo[1,4]oxazine-6-carboxylic acid. This was reacted with ethyl 2-amino-4-thiazoleacetate in step 5 and yielded (2-{[4-(3-chloro-benzenesulfonyl)-3,4-dihydro-2H-benzo[1,4]oxazine-6-carbonyl]-amino}-thiazol-4-yl)acetic acid ethyl ester, which was hydrolyzed in step 6.

Example 93

(2-{[4-(3,5-Dimethyl-benzenesulfonyl)-3,4-dihydro-2H-benzo[1,4]oxazine-6-carbonyl]-amino}-thiazol-4-yl)-acetic acid The title compound, MS (ISP)=486.3 (M−H)$^-$, was produced as described in example 1, steps 1-6. Step 3 was performed using 3,5-dimethylbenzenesulfonyl chloride, furnishing 4-(3,5-Dimethyl-benzenesulfonyl)-3,4-dihydro-2H-benzo[1,4]oxazine-6-carboxylic acid methyl ester, which was hydrolyzed in step 4, leading to 4-(3,5-dimethyl-benzenesulfonyl)-3,4-dihydro-2H-benzo[1,4]oxazine-6-carboxylic acid. This was reacted with ethyl 2-amino-4-thiazoleacetate in step 5 and yielded (2-{[4-(3,5-dimethyl-benzenesulfonyl)-3,4-dihydro-2H-benzo[1,4]oxazine-6-carbonyl]-amino}-thiazol-4-yl)-acetic acid ethyl ester, which was hydrolyzed in step 6.

Example 94

(3-{[3-(5-Chloro-2-methoxy-benzenesulfonyl)-2,3-dihydro-benzooxazole-5-carbonyl]-amino}-pyrazol-1-yl)-acetic acid The title compound, MS (ISP)=491.1 (M−H)$^-$, was produced as described in example 52, steps 1-6. Step 5 was performed using (3-amino-pyrazol-1-yl)-acetic acid ethyl ester and yielded (3-{[3-(5-chloro-2-methoxy-benzenesulfonyl)-2,3-dihydro-benzooxazole-5-carbonyl]-amino}-pyrazol-1-yl)-acetic acid ethyl ester, which was hydrolyzed in step 6.

Example 95

4-{[4-(3-Chloro-benzenesulfonyl)-3,4-dihydro-2H-benzo[1,4]thiazine-6-carbonyl]-amino}-benzoic acid Step 1. 3,4-Dihydro-2H-benzo[1,4]thiazine-6-carboxylic acid methyl ester (example 55, step 1) was reacted with 3-chloro-benzenesulfonyl chloride in accordance with the general method of example 30, step 1 and led to 4-(3-chloro-benzenesulfonyl)-3,4-dihydro-2H-benzo[1,4]thiazine-6-carboxylic acid methyl ester. Off-white foam, MS (ISP)=384.1 (M+H)+.

Step 2. Hydrolysis of 4-(3-chloro-benzenesulfonyl)-3,4-dihydro-2H-benzo[1,4]thiazine-6-carboxylic acid methyl ester in accordance with the general method of example 1, step 4 produced 4-(3-chloro-benzenesulfonyl)-3,4-dihydro-2H-benzo[1,4]thiazine-6-carboxylic acid. White solid, MS (ISP)=370.0 (M+H)+.

Step 3. Reaction of 4-(3-chloro-benzenesulfonyl)-3,4-dihydro-2H-benzo[1,4]thiazine-6-carboxylic acid with tert-butyl 4-aminobenzoate in accordance with the general method of example 30, step 4 produced 4-{[4-(3-chloro-benzenesulfonyl)-3,4-dihydro-2H-benzo[1,4]thiazine-6-carbonyl]-amino}-benzoic acid tert-butyl ester. White foam, MS (ISP)=545.3 (M+H)+.

Step 4. Hydrolysis of 4-{[4-(3-chloro-benzenesulfonyl)-3,4-dihydro-2H-benzo[1,4]thiazine-6-carbonyl]-amino}-benzoic acid tert-butyl ester in accordance with the general method of example 96, step 2 produced the title compound. White solid, MS (ISP)=487.1 (M−H)−.

Example 96

4-{[4-(3-Chloro-benzenesulfonyl)-1-oxo-1,2,3,4-tetrahydro-benzo[1,4]thiazine-6-carbonyl]-amino}-benzoic acid Step 1. A solution of 4-(3-chloro-benzenesulfonyl)-3,4-dihydro-2H-benzo[1,4]thiazine-6-carboxylic acid tert-butyl ester (example 95, step 3; 192 mg, 0.352 mmol) in dichloromethane (2 mL) was treated at 0° C. with 3-chloroperbenzoic acid (61 mg, 0.35 mmol). The reaction mixture was stirred at 0° C. for 4 h, then partitioned between dichloromethane and 2 M aq. sodium carbonate solution. The organic layer was dried (MgSO4), and evaporated. Chromatography (SiO2, ethyl acetate) afforded 4-{[4-(3-chloro-benzenesulfonyl)-1-oxo-1,2,3,4-tetrahydro-benzo[1,4]thiazine-6-carbonyl]-amino}-benzoic acid tert-butyl ester (153 mg, 77%). White solid, MS (ISP)=561.2 (M+H)+.

Step 2. A suspension of 4-{[4-(3-chloro-benzenesulfonyl)-1-oxo-1,2,3,4-tetrahydro-benzo[1,4]thiazine-6-carbonyl]-amino}-benzoic acid tert-butyl ester (153 mg, 0.273 mmol) in formic acid (4 mL) was stirred for 16 h at room temperature, then the solution obtained was treated with water, and the suspension was stirred for another 90 min. The precipitate was collected by filtration and dried to produce the title compound (126 mg, 92%). White solid, 505.2 (M+H)+.

Example 97

4-{[4-(3-Chloro-benzenesulfonyl)-1,1-dioxo-1,2,3,4-tetrahydro-benzo[1,4]thiazine-6-carbonyl]-amino}-benzoic acid The title compound, MS (ISP)=521.2 (M+H)+, was produced in accordance with the general method of example 70, step 2 from 4-(3-chloro-benzenesulfonyl)-3,4-dihydro-2H-benzo[1,4]thiazine-6-carboxylic acid tert-butyl ester (example 95, step 3).

Example 98

4-{[4-(3,5-Dimethyl-benzenesulfonyl)-3,4-dihydro-2H-benzo[1,4]thiazine-6-carbonyl]-amino}-benzoic acid Step 1. 3,4-Dihydro-2H-benzo[1,4]thiazine-6-carboxylic acid methyl ester (example 55, step 1) was reacted with 3,5-dimethyl-benzenesulfonyl chloride in accordance with the general method of example 30, step 1 and led to 4-(3,5-dimethyl-benzenesulfonyl)-3,4-dihydro-2H-benzo[1,4]thiazine-6-carboxylic acid methyl ester. White foam, MS (ISP)=378.2 (M+H)+.

Step 2. Hydrolysis of 4-(3,5-dimethyl-benzenesulfonyl)-3,4-dihydro-2H-benzo-[1,4]thiazine-6-carboxylic acid methyl ester in accordance with the general method of example 1, step 4 produced 4-(3,5-dimethyl-benzenesulfonyl)-3,4-dihydro-2H-benzo[1,4]thiazine-6-carboxylic acid. White solid, MS (ISP)=364.1 (M+H)+.

Step 3. Reaction of 4-(3,5-dimethyl-benzenesulfonyl)-3,4-dihydro-2H-benzo[1,4]thiazine-6-carboxylic acid with tert-butyl 4-aminobenzoate in accordance with the general method of example 30, step 4 produced 4-{[4-(3,5-dimethyl-benzenesulfonyl)-3,4-dihydro-2H-benzo[1,4]thiazine-6-carbonyl]-amino}-benzoic acid tert-butyl ester. White solid, MS (ISP)=539.3 (M+H)+.

Step 4. Hydrolysis of 4-{[4-(3,5-dimethyl-benzenesulfonyl)-3,4-dihydro-2H-benzo-[1,4]thiazine-6-carbonyl]-amino}-benzoic acid tert-butyl ester in accordance with the general method of example 96, step 2 produced the title compound. White solid, MS (ISP)=483.4 (M+H)+.

Example 99

4-{[4-(3,5-Dimethyl-benzenesulfonyl)-1-oxo-1,2,3,4-tetrahydro-benzo[1,4]thiazine-6-carbonyl]-amino}-benzoic acid The title compound, MS (ISP)=499.2 (M+H)+, was produced as described in example 96, steps 1-2. Oxidation of 4-(3,5-dimethyl-benzenesulfonyl)-3,4-dihydro-2H-benzo[1,4]thiazine-6-carboxylic acid tert-butyl ester (example 98, step 3) in step 1 produced 4-{[4-(3,5-dimethylbenzenesulfonyl)-1-oxo-1,2,3,4-tetrahydro-benzo[1,4]thiazine-6-carbonyl]-amino}-benzoic acid tert-butyl ester, which was hydrolyzed in step 2.

Example 100

4-{[4-(3,5-Dimethyl-benzenesulfonyl)-1,1-dioxo-1,2,3,4-tetrahydro-benzo[1,4]thiazine-6-carbonyl]-amino}-benzoic acid The title compound, MS (ISP)=515.3 (M+H)+, was produced in accordance with the general method of example 70, step 2 from 4-(3,5-dimethyl-benzenesulfonyl)-3,4-dihydro-2H-benzo[1,4]thiazine-6-carboxylic acid tert-butyl ester (example 98, step 3).

Example 101

4-{[4-(5-Chloro-2-methoxy-benzenesulfonyl)-1-oxo-1,2,3,4-tetrahydro-benzo[1,4]thiazine-6-carbonyl]-amino}-benzoic acid The title compound, MS (ISP)=533.3 (M−H)−, was produced as described in example 96, steps 1-2. Oxidation of 4-(5-chloro-2-methoxy-benzenesulfonyl)-3,4-dihydro-2H-benzo[1,4]thiazine-6-carboxylic acid tert-butyl ester (example 70, step 1) in step 1 produced 4-{[4-(5-chloro-2-methoxy-benzenesulfonyl)-1-oxo-1,2,3,4-tetrahydro-benzo[1,4]

Example 102

(4-{[4-(5-Chloro-2-methoxy-benzenesulfonyl)-1-oxo-1,2,3,4-tetrahydro-benzo[1,4]thiazine-6-carbonyl]-amino}-phenyl)-acetic acid Step 1. Reaction of 4-(5-chloro-2-methoxy-benzenesulfonyl)-3,4-dihydro-2H-benzo-[1,4]thiazine-6-carboxylic acid (example 55, step 3) with tert-butyl (4-aminophenyl)acetate in accordance with the general method of example 30, step 5 produced (4-{[4-(5-chloro-2-methoxybenzenesulfonyl)-3,4-dihydro-2H-benzo[1,4]thiazine-6-carbonyl]-amino}-phenyl)-acetic acid tert-butyl ester. Orange solid, MS (ISP)= 589.5 $(M+H)^+$.

Step 2. Oxidation of (4-{[4-(5-chloro-2-methoxy-benzenesulfonyl)-3,4-dihydro-2H-benzo[1,4]thiazine-6-carbonyl]-amino}-phenyl)-acetic acid tert-butyl ester in accordance with the general method of example 96, step 1 produced (4-{[4-(5-chloro-2-methoxy-benzenesulfonyl)-1-oxo-1,2,3,4-tetrahydro-benzo[1,4]thiazine-6-carbonyl]-amino}-phenyl)-acetic acid tert-butyl ester. Off-white solid, MS (ISP)=605.3 $(M+H)^+$.

Step 3. Hydrolysis of (4-{[4-(5-chloro-2-methoxy-benzenesulfonyl)-1-oxo-1,2,3,4-tetrahydro-benzo[1,4]thiazine-6-carbonyl]-amino}-phenyl)-acetic acid tert-butyl ester in accordance with the general method of example 96, step 2 produced the title compound. White solid, 549.2 $(M+H)^+$.

Example 103

(4-{[4-(5-Chloro-2-methoxy-benzenesulfonyl)-1,1-dioxo-1,2,3,4-tetrahydro-benzo[1,4]thiazine-6-carbonyl]-amino}-phenyl)-acetic acid The title compound, MS (ISP)=565.2 $(M+H)^+$, was produced in accordance with the general method of example 70, step 2 from (4-{[4-(5-chloro-2-methoxy-benzenesulfonyl)-3,4-dihydro-2H-benzo[1,4]thiazine-6-carbonyl]-amino}-phenyl)-acetic acid tert-butyl ester (example 102, step 1).

Example 104

4-{[4-(5-Chloro-2-methoxy-benzenesulfonyl)-3,4-dihydro-2H-benzo[1,4]thiazine-6-carbonyl]-amino}-2-fluoro-benzoic acid Step 1. Reaction of 4-(5-chloro-2-methoxy-benzenesulfonyl)-3,4-dihydro-2H-benzo-[1,4]thiazine-6-carboxylic acid (example 55, step 3) with tert-butyl 4-amino-2-fluorobenzoate in accordance with the general method of example 30, step 5 produced 4-{[4-(5-chloro-2-methoxybenzenesulfonyl)-3,4-dihydro-2H-benzo[1,4]thiazine-6-carbonyl]-amino}-2-fluoro-benzoic acid tert-butyl ester. Off-white solid, MS (ISP)=591.2 $(M+H)^+$.

Step 2. Hydrolysis of 4-{[4-(5-chloro-2-methoxy-benzenesulfonyl)-3,4-dihydro-2H-benzo[1,4]thiazine-6-carbonyl]-amino}-2-fluoro-benzoic acid tert-butyl ester in accordance with the general method of example 96, step 2 produced the title compound. White solid, MS (ISP)=537.2 $(M+H)^+$.

Example 105

4-{[4-(5-Chloro-2-methoxy-benzenesulfonyl)-1,1-dioxo-1,2,3,4-tetrahydro-benzo[1,4]thiazine-6-carbonyl]-amino}-2-fluoro-benzoic acid The title compound, MS (ISP)=569.1 $(M+H)^+$, was produced in accordance with the general method of example 70, step 2 from 4-{[4-(5-chloro-2-methoxy-benzenesulfonyl)-3,4-dihydro-2H-benzo[1,4]thiazine-6-carbonyl]-amino}-2-fluoro-benzoic acid tert-butyl ester (example 104, step 1).

Example 106

2-Chloro-4-{[4-(5-chloro-2-methoxy-benzenesulfonyl)-3,4-dihydro-2H-benzo[1,4]thiazine-6-carbonyl]-amino}-benzoic acid Step 1. Reaction of 4-(5-chloro-2-methoxy-benzenesulfonyl)-3,4-dihydro-2H-benzo-[1,4]thiazine-6-carboxylic acid (example 55, step 3) with tert-butyl 4-amino-2-chloro in step 1 in accordance with the general method of example 30, step 5 produced 2-chloro-4-{[4-(5-chloro-2-methoxy-benzenesulfonyl)-3,4-dihydro-2H-benzo[1,4]thiazine-6-carbonyl]-amino}-benzoic acid tert-butyl ester. White solid, MS (ISP)= 609.1 $(M+H)^+$.

Step 2. Hydrolysis of 2-chloro-4-{[4-(5-chloro-2-methoxy-benzenesulfonyl)-3,4-dihydro-2H-benzo[1,4]thiazine-6-carbonyl]-amino}-benzoic acid tert-butyl ester in accordance with the general method of example 96, step 2 produced the title compound. White solid, MS (ISP)=553.0 $(M+H)^+$.

Preparation of tert-butyl 4-amino-2-chloro-benzoate

Lithium tert-butylate (2.2 M in tetrahydrofuran, 6.2 mL, 13.6 mmol) was added to a solution of 2-chloro-4-nitrobenzoyl chloride (2.00 g, 9.09 mmol) in tetrahydrofuran (12 mL) at 0° C. The orange solution was kept at 0° C. for 1.5 h, then allowed to reach room temperature over 16 h, then partitioned between 1 M aq. sodium carbonate solution and isopropyl acetate. The organic layer was dried (MgSO$_4$) and evaporated to afford tert-butyl 2-chloro-4-nitro-benzoate (2.05 g, 88%) which was directly used in the next step. Brown oil, MS (EI)=257.1 $(M^+)$.

To a solution of tert-butyl 2-chloro-4-nitro-benzoate (2.05 g, 7.98 mmol) in ethanol 12 mL) and ethyl acetate (108 mL) was added platinum on activated charcoal (5%, 295 mg), and the mixture was stirred under at room temperature under a hydrogen atmosphere (1 bar). After filtration through a pad of diatomaceous earth, the filtrate was evaporated to afford tert-butyl 4-amino-2-chlorobenzoate (1.75 g, 96%). Orange solid, MS (EI)=227.2 $(M^+)$.

Example 107

2-Chloro-4-{[4-(5-chloro-2-methoxy-benzenesulfonyl)-1,1-dioxo-1,2,3,4-tetrahydro-benzo[1,4]thiazine-6-carbonyl]-amino}-benzoic acid The title compound, MS (ISP)=584.9 $(M+H)^+$, was produced in accordance with the general method of example 70, step 2 from 2-chloro-4-{[4-(5-chloro-2-methoxy-benzenesulfonyl)-3,4-dihydro-2H-benzo[1,4]thiazine-6-carbonyl]-amino}-benzoic acid tert-butyl ester (example 106, step 1).

Example 108

4-(5-Chloro-2-methoxy-benzenesulfonyl)-6-phenyl-carbamoyl-3,4-dihydro-2H-benzo[1,4]oxazine-2-carboxylic acid ethyl ester Step 1. A mixture of 2-amino-4-bromophenol (5.00 g, 26.6 mmol), ethyl 2,3-dibromopropionate (7.84 g, 29.2 mmol), and potassium carbonate (10.3 g, 81.8 mmol) in acetone (55 mL) was heated at reflux for 16 h. After evaporation of volatile material, the residue was partitioned between dichloromethane and water. The organic layer was washed with 1 M aq. sodium carbonate solution and brine, dried ($MgSO_4$), and evaporated. Chromatography ($SiO_2$, heptane-ethyl acetate gradient produced 6-bromo-3,4-dihydro-2H-benzo[1,4]oxazine-2-carboxylic acid ethyl ester (5.95 g, 78%). Orange solid, MS (ISP)=286.0 $(M+H)^+$.

Step 2. 6-Bromo-3,4-dihydro-2H-benzo[1,4]oxazine-2-carboxylic acid ethyl ester was reacted with 5-chloro-2-methoxy-benzenesulfonyl chloride in accordance with the general method of example 30, step 1 and led to 6-bromo-4-(5-chloro-2-methoxy-benzenesulfonyl)-3,4-dihydro-2H-benzo[1,4]oxazine-2-carboxylic acid ethyl ester. Yellow solid, MS (ISP)=489.9 $(M+H)^+$.

Step 3. A mixture of 6-bromo-4-(5-chloro-2-methoxy-benzenesulfonyl)-3,4-dihydro-2H-benzo[1,4]oxazine-2-carboxylic acid ethyl ester (200 mg, 0.408 mmol), molybdenum hexacarbonyl (108 mg, 0.408 mmol), aniline (114 mg, 1.22 mmol), 1,8-diazabicyclo[5.4.0]undec-7-ene (192 mg, 1.22 mmol) trans-bis(μ-acetato)bis[o-(di-o-tolylphosphino)benzyl]dipalladium(II) (12 mg, 37 μmol), and tris(tert-butyl)phosphine tetrafluoroborate (6 mg, 20 μmol) in tetrahydrofuran (1 mL) was heated for 10 min at 140° C. under microwave irradiation, then the reaction mixture was partitioned between water and ethyl acetate. The organic layer was washed with brine, dried ($MgSO_4$), and evaporated. Chromatography ($SiO_2$, heptane-ethyl acetate gradient produced the title compound (111 mg, 51%). Off-white foam, MS (ISP)=531.0 $(M+H)^+$.

Example 109

4-(5-Chloro-2-methoxy-benzenesulfonyl)-6-phenyl-carbamoyl-3,4-dihydro-2H-benzo[1,4]oxazine-2-carboxylic acid The title compound, MS (ISP)=501.4 $(M-H)^-$, was produced in accordance with the general method of example 1, step 6 from 4-(5-chloro-2-methoxy-benzenesulfonyl)-6-phenylcarbamoyl-3,4-dihydro-2H-benzo[1,4]oxazine-2-carboxylic acid ethyl ester.

Example 110

4-(5-Chloro-2-methoxy-benzenesulfonyl)-6-(2-fluoro-phenylcarbamoyl)-3,4-dihydro-2H-benzo[1,4]oxazine-2-carboxylic acid ethyl ester The title compound, MS (ISP)=549.3 $(M+H)^+$, was produced as described in example 108, steps 1-3. Step 3 was performed using 2-fluoroaniline as amine reagent.

Example 111

4-(5-Chloro-2-methoxy-benzenesulfonyl)-6-(2-fluoro-phenylcarbamoyl)-3,4-dihydro-2H-benzo[1,4]oxazine-2-carboxylic acid The title compound, MS (ISP)=519.3 $(M-H)^-$, was produced in accordance with the general method of example 1, step 6 from 4-(5-chloro-2-methoxy-benzenesulfonyl)-6-(2-fluorophenylcarbamoyl)-3,4-dihydro-2H-benzo[1,4]oxazine-2-carboxylic acid ethyl ester ethyl ester.

Example 112

4-(5-Chloro-2-methoxy-benzenesulfonyl)-6-(3-fluoro-phenylcarbamoyl)-3,4-dihydro-2H-benzo[1,4]oxazine-2-carboxylic acid ethyl ester The title compound, MS (ISP)=549.3 $(M+H)^+$, was produced as described in example 108, steps 1-3. Step 3 was performed using 3-fluoroaniline as amine reagent.

Example 113

4-(5-Chloro-2-methoxy-benzenesulfonyl)-6-(3-fluoro-phenylcarbamoyl)-3,4-dihydro-2H-benzo[1,4]oxazine-2-carboxylic acid The title compound, MS (ISP)=519.3 $(M-H)^-$, was produced in accordance with the general method of example 1, step 6 from 4-(5-chloro-2-methoxy-benzenesulfonyl)-6-(3-fluorophenylcarbamoyl)-3,4-dihydro-2H-benzo[1,4]oxazine-2-carboxylic acid ethyl ester ethyl ester.

Example 114

4-(5-Chloro-2-methoxy-benzenesulfonyl)-6-(4-fluoro-phenylcarbamoyl)-3,4-dihydro-2H-benzo[1,4]oxazine-2-carboxylic acid ethyl ester The title compound, MS (ISP)=549.3 $(M+H)^+$, was produced as described in example 108, steps 1-3. Step 3 was performed using 4-fluoroaniline as amine reagent.

Example 115

4-(5-Chloro-2-methoxy-benzenesulfonyl)-6-(4-fluoro-phenylcarbamoyl)-3,4-dihydro-2H-benzo[1,4]oxazine-2-carboxylic acid The title compound, MS (ISP)=519.1 $(0M-H)^-$, was produced in accordance with the general method of example 1, step 6 from 4-(5-chloro-2-methoxy-benzenesulfonyl)-6-(4-fluorophenylcarbamoyl)-3,4-dihydro-2H-benzo[1,4]oxazine-2-carboxylic acid ethyl ester ethyl ester.

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Polyvinylpyrrolidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |

| Ingredients | Per tablet | |
|---|---|---|
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene glycol 400 | 150.0 mg |
| Acetic Acid | q.s. ad pH 5.0 |
| Water for injection solutions | ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula (I) | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

It is to be understood that the invention is not limited to the particular embodiments of the invention described above, as variations of the particular embodiments may be made and still fall within the scope of the appended claims.

What is claimed is:

1. A compound of formula (I):

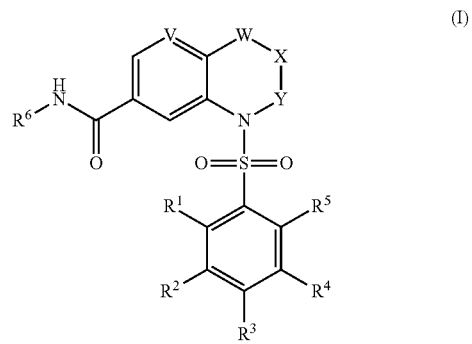

wherein:

V is —C($R^7$)—;

W is a single bond;

X is N($R^{10}$);

Y is —C($R^{11}R^{12}$)C($R^{13}R^{14}$) or —C($R^{11}$)=C($R^{12}$)—;

$R^1$, $R^2$, $R^3$, $R^4$ and $R^5$ independently from each other are hydrogen, halogen, cyano, hydroxy, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H,lower-alkyl)-S(O)$_2$ or N(lower-alkyl)$_2$-S(O)$_2$, NH$_2$—C(O), N(H,lower-alkyl)-C(O), N(lower-alkyl)$_2$-C(O), COOH or lower-alkoxy-C(O), wherein lower-alkyl is optionally substituted with hydroxy, NH$_2$, N(H, lower-alkyl) or N(lower-alkyl)$_2$;

$R^6$ is an aryl or heteroaryl group, which aryl or heteroaryl group is optionally substituted by 1 to 4 substituents selected from the group consisting of halogen, hydroxy, cyano, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H,lower-alkyl)S(O)$_2$, N(lower-alkyl)$_2$-S(O)$_2$, NH$_2$—C(O), N(H,lower-alkyl)-C(O), N(lower-alkyl)$_2$-C(O), lower-alkoxy-C(O), COOH, 1H-tetrazol-5-yl, 5-oxo-4H-[1,2,4]oxadiazol-3-yl, 5-oxo-4H-[1,2,4]thiadiazol-3-yl, 5-thioxo-4H-[1,2,4]oxadiazol-3-yl, 2-oxo-3H-[1,2,3,5]oxathiadiazol-4-yl, SO$_3$H, 3-hydroxy-isooxazol-5-yl, 6-oxo-6H-pyran-3-yl, 6-oxo-6H-pyran-2-yl, 2-oxo-2H-pyran-3-yl, 2-oxo-2H-pyran-4-yl and P(O)(OCH$_2$CH$_3$)OH, wherein lower-alkyl is optionally substituted with COOH, hydroxy, NH$_2$, N(H,lower-alkyl) or N(lower-alkyl)$_2$, and wherein fluoro-lower-alkyl is optionally substituted with hydroxy;

$R^7$ is hydrogen, halogen, lower-alkyl, lower-alkoxy, fluoro-lower-alkyl, fluoro-lower-alkoxy, hydroxy or hydroxy-lower-alkyl;

$R^{10}$ is hydrogen, lower-alkyl, cycloalkyl, lower-alkyl-C(O), lower-alkyl-S(O)$_2$, lower-alkoxy-C(O), (lower-alkyl)NH—C(O), or (lower-alkyl)$_2$N—C(O);

$R^{11}$, $R^{12}$, $R^{13}$, and $R^{14}$ independently from each other are hydrogen, halogen, hydroxy, lower alkyl, lower-alkoxy, fluoro-lower-alkyl, fluoro-lower-alkoxy, hydroxy-lower-alkyl, aryl, COOH, C(O)O-lower-alkyl or cyano;

or a pharmaceutically acceptable salt or ester thereof.

2. The compound according to claim 1, wherein $R^{11}$, $R^{12}$, $R^{13}$, and $R^{14}$ independently from each other are hydrogen, halogen, hydroxy, lower alkyl, lower-alkoxy, fluoro-lower-alkyl, fluoro-lower-alkoxy, hydroxy-lower-alkyl, aryl or cyano.

3. The compound according to claim 1, wherein $R^1$, $R^2$, $R^3$, $R^4$ and $R^5$ independently from each other are hydrogen, halogen, lower-alkyl, fluoro-lower-alkyl, lower-alkoxy, fluoro-lower-alkoxy or NH$_2$—C(O).

4. The compound according to claim 1, wherein $R^1$, $R^2$, $R^3$, $R^4$ and $R^5$ independently from each other are hydrogen, halogen or lower-alkyl.

5. The compound according to claim 1, wherein $R^1$ is lower-alkoxy.

6. The compound according to claim 1, wherein $R^1$ is methoxy.

7. The compound according to claim 1, wherein $R^2$, $R^3$ and $R^5$ are hydrogen.

8. The compound according to claim 1, wherein $R^4$ is halogen.

9. The compound according to claim 1, wherein $R^4$ is chloro.

10. The compound according to claim 1, wherein $R^6$ is an aryl or heteroaryl group, which aryl or heteroaryl group is optionally substituted by 1 to 4 substituents selected from the group consisting of halogen, cyano, lower-alkyl, carboxy-lower-alkyl, lower-alkoxy, COOH, 1H-tetrazol-5-yl and 5-oxo-4H-[1,2,4]oxadiazol-3-yl.

11. The compound according to claim 1, wherein $R^6$ is a phenyl, pyridinyl, pyrazolyl or thiazolyl group, which group is optionally substituted by 1 to 2 substituents selected from the group consisting of halogen, cyano, lower-alkyl, carboxy-lower-alkyl, lower-alkoxy, COOH, 1H-tetrazol-5-yl and 5-oxo-4H-[1,2,4]oxadiazol-3-yl.

12. The compound according to claim 1, wherein $R^6$ is a phenyl, pyridinyl or thiazolyl group, which group is optionally substituted by 1 to 2 substituents selected from the group consisting of halogen, carboxy-lower-alkyl and COOH.

13. The compound according to claim 1, wherein $R^6$ is 4-carboxy-phenyl, 3-fluoro-4-carboxy-phenyl, 3-chloro-4-carboxy-phenyl, 2-carboxy-pyridin-5-yl, 4-carboxy-methyl-phenyl, 4-carboxy-methyl-thiazol-2-yl or 2-carboxy-methyl-thiazol-4-yl.

14. The compound according to claim 1, wherein $R^7$ is hydrogen, halogen, lower-alkyl, lower-alkoxy or fluoro-lower-alkoxy.

15. The compound according to claim 1, wherein $R^7$ is hydrogen or halogen.

16. The compound according to claim 1, wherein $R^7$ is hydrogen or fluoro.

17. The compound according to claim 1, wherein $R^{10}$ is hydrogen.

18. The compound according to claim 1, wherein $R^{11}$, $R^{12}$, $R^{13}$, and $R^{14}$ independently from each other are hydrogen or phenyl.

19. The compound according to claim 1, wherein $R^{11}$, $R^{12}$, $R^{13}$, and $R^{14}$ are hydrogen.

20. The compound according to claim 1, wherein $R^{11}$, $R^{12}$, $R^{13}$, and $R^{14}$ independently of each other are hydrogen, COOH or C(O)O-lower-alkyl.

21. The compound according to claim 1, selected from the group consisting of
 4-{[4-(5-Chloro-2-methoxy-benzenesulfonyl)-1,2,3,4-tetrahydro-quinoxaline-6-carbonyl]-amino}-benzoic acid,
 5-{[4-(5-Chloro-2-methoxy-benzenesulfonyl)-1,2,3,4-tetrahydro-quinoxaline-6-carbonyl]-amino}-pyridine-2-carboxylic acid, and
 4-{[4-(5-Chloro-2-methoxy-benzenesulfonyl)-1,2,3,4-tetrahydro-quinoxaline-6-carbonyl]-amino}-2-fluoro-benzoic acid.

22. A process for the manufacture of compounds of formula (I) as defined in claim 1, comprising the step of:

a) reacting a compound of formula (XIV)

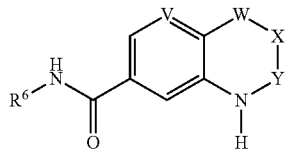
(XIV)

with a compound of formula (XV)

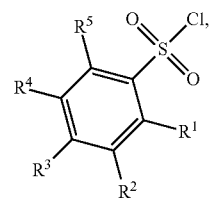
(XV)

or b) reacting a compound of formula (XVI)

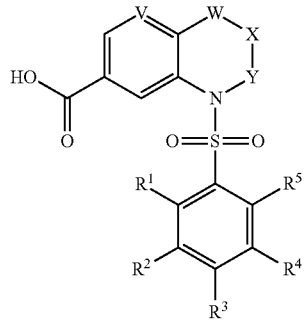
(XVI)

with a compound $R^6$—$NH_2$, wherein $R^1$, $R^2$, $R^3$, $R^4$, $R^5$, $R^6$, V, W, X and Y are as defined claim 1.

23. A pharmaceutical composition, comprising a therapeutically effective amount of a compound according to claim 1 and a pharmaceutically acceptable carrier and/or adjuvant.

24. A method for the treatment of type II diabetes, comprising the step of administering a therapeutically effective amount of a compound according to claim 1 to a human being or animal in need thereof.

\* \* \* \* \*